US009440988B2

(12) United States Patent
Beachy et al.

(10) Patent No.: US 9,440,988 B2
(45) Date of Patent: *Sep. 13, 2016

(54) REGULATORS OF THE HEDGEHOG PATHWAY, COMPOSITIONS AND USES RELATED THERETO

(75) Inventors: Philip A. Beachy, Ruxton, MD (US); James K. Chen, Mountain View, CA (US); Anssi Jussi Nikolai Taipale, Espoo (FI)

(73) Assignee: John Hopkins University School of Medicine, Baltimore, MD (US)

( * ) Notice: Subject to any disclaimer, the term of this patent is extended or adjusted under 35 U.S.C. 154(b) by 1368 days.

This patent is subject to a terminal disclaimer.

(21) Appl. No.: 13/363,934

(22) Filed: Feb. 1, 2012

(65) Prior Publication Data

US 2012/0135066 A1    May 31, 2012

Related U.S. Application Data

(60) Continuation of application No. 13/176,297, filed on Jul. 5, 2011, now Pat. No. 8,163,719, which is a continuation of application No. 12/079,776, filed on Mar. 28, 2008, now Pat. No. 7,998,946, which is a continuation of application No. 11/338,503, filed on Jan. 23, 2006, now Pat. No. 7,476,661, which is a continuation of application No. 09/688,076, filed on Oct. 13, 2000, now Pat. No. 7,098,196, application No. 13/363,934, which is a continuation-in-part of application No. 13/364,121, filed on Feb. 1, 2012, which is a continuation of application No. 12/652,134, filed on Jan. 5, 2010, now abandoned, which is a continuation of application No. 11/270,984, filed on Nov. 11, 2005, now abandoned, which is a division of application No. 09/708,964, filed on Nov. 8, 2000, now Pat. No. 7,291,626, which is a division of application No. 09/685,244, filed on Oct. 10, 2000, now abandoned, which is a continuation-in-part of application No. PCT/US99/07811, filed on Apr. 9, 1999, and a continuation-in-part of application No. 09/090,622, filed on Jun. 4, 1998, now Pat. No. 6,432,970.

(60) Provisional application No. 60/159,215, filed on Oct. 13, 1999, provisional application No. 60/229,273, filed on Aug. 30, 2000, provisional application No. 60/081,186, filed on Apr. 9, 1998, provisional application No. 60/081,263, filed on Apr. 9, 1008.

(51) Int. Cl.

| C07D 491/048 | (2006.01) |
| A61K 31/4355 | (2006.01) |
| A61K 31/58 | (2006.01) |
| C07D 491/10 | (2006.01) |
| C07D 519/00 | (2006.01) |
| C07J 69/00 | (2006.01) |

(52) U.S. Cl.
CPC ......... *C07D 491/10* (2013.01); *A61K 31/4355* (2013.01); *A61K 31/58* (2013.01); *C07D 491/048* (2013.01); *C07D 519/00* (2013.01); *C07J 69/00* (2013.01)

(58) Field of Classification Search
None
See application file for complete search history.

(56) References Cited

U.S. PATENT DOCUMENTS

| 3,673,175 A | 6/1972 | Schramm et al. |
| 5,028,422 A | 7/1991 | Tanner et al. |
| 5,466,687 A | 11/1995 | Maier et al. |
| 5,486,511 A | 1/1996 | Weintraubet et al. |
| 5,595,743 A | 1/1997 | Wu |
| 5,639,738 A | 6/1997 | Falk et al. |
| 5,736,154 A | 4/1998 | Fuisz et al. |
| 5,756,528 A | 5/1998 | Anthony et al. |
| 5,817,678 A | 10/1998 | Kim et al. |
| 5,891,465 A | 4/1999 | Keller et al. |
| 5,892,038 A | 4/1999 | Dolle, III et al. |
| 5,958,770 A | 9/1999 | Cham et al. |
| 5,972,986 A | 10/1999 | Seibert et al. |
| 5,985,930 A | 11/1999 | Pasinetti et al. |
| 6,057,091 A | 5/2000 | Beachy et al. |
| 6,127,366 A | 10/2000 | Kim et al. |
| 6,147,100 A | 11/2000 | Seno et al. |
| 6,238,876 B1 | 5/2001 | Altaba |
| 6,242,196 B1 | 6/2001 | Spiegelman et al. |
| 6,288,048 B1 | 9/2001 | Beachy et al. |
| 6,291,516 B1 | 9/2001 | Dudek et al. |
| 6,432,970 B2 | 8/2002 | Beachy et al. |
| 6,495,532 B1 | 12/2002 | Bathurst et al. |

(Continued)

FOREIGN PATENT DOCUMENTS

| EP | 0 020 029 | 12/1980 |
| EP | 0 375 349 | 6/1990 |

(Continued)

OTHER PUBLICATIONS

U.S. Appl. No. 13/364,121, filed Feb. 2012, Beachy, Philip A.*

(Continued)

*Primary Examiner* — Eric Olson
(74) *Attorney, Agent, or Firm* — Millen, White, Zelano, Branigan, P.C.

(57) ABSTRACT

The present invention makes available, inter alia, methods and reagents for modulating smoothened-dependent pathway activation. In certain embodiments, the subject methods can be used to counteract the phenotypic effects of unwanted activation of a hedgehog pathway, such as resulting from hedgehog gain-of-function, ptc loss-of-function or smoothened gain-of-function mutations.

26 Claims, 12 Drawing Sheets

(56) References Cited

U.S. PATENT DOCUMENTS

| | | | |
|---|---|---|---|
| 6,552,016 | B1 | 4/2003 | Baxter et al. |
| 6,686,388 | B2 | 2/2004 | Dudek et al. |
| 6,867,216 | B1 | 3/2005 | Beachy et al. |
| 7,098,196 | B1 | 8/2006 | Beachy et al. |
| 7,291,626 | B1 | 11/2007 | Beachy et al. |
| 7,390,688 | B2 | 6/2008 | Wakabayashi et al. |
| 7,476,661 | B2 | 1/2009 | Beachy et al. |
| 7,893,078 | B2 | 2/2011 | Tas et al. |
| 7,998,946 | B2 | 8/2011 | Beachy et al. |
| 8,097,632 | B2 | 1/2012 | Beachy et al. |
| 2002/0165221 | A1 | 11/2002 | Baxter et al. |
| 2003/0022819 | A1 | 1/2003 | Ling et al. |
| 2003/0139457 | A1 | 7/2003 | Baxter et al. |
| 2004/0023949 | A1 | 2/2004 | Baxter et al. |
| 2004/0060568 | A1 | 4/2004 | Dudek et al. |
| 2004/0072913 | A1 | 4/2004 | Tas et al. |
| 2004/0072914 | A1 | 4/2004 | Tas et al. |
| 2004/0110663 | A1 | 6/2004 | Dudek et al. |
| 2004/0127474 | A1 | 7/2004 | Dudek et al. |
| 2005/0011207 | A1 | 1/2005 | Porter et al. |
| 2005/0014796 | A1 | 1/2005 | Baxter et al. |
| 2005/0054568 | A1 | 3/2005 | Ling et al. |
| 2005/0080138 | A1 | 4/2005 | Guicherit et al. |
| 2005/0130922 | A1 | 6/2005 | Altaba et al. |
| 2006/0142245 | A1 | 6/2006 | Beachy et al. |
| 2008/0058298 | A1 | 3/2008 | Beachy et al. |
| 2008/0255059 | A1 | 10/2008 | Beachy et al. |
| 2010/0080855 | A1* | 4/2010 | Beachy et al. ............ 424/623 |
| 2010/0273818 | A1 | 10/2010 | Beachy et al. |

FOREIGN PATENT DOCUMENTS

| | | |
|---|---|---|
| EP | 0 495 684 | 7/1992 |
| GB | 1 227 728 | 4/1971 |
| JP | 04230696 | 8/1992 |
| JP | 08-034742 | 2/1996 |
| KR | 2005 037103 | 4/2005 |
| WO | WO-91 10743 | 7/1991 |
| WO | WO-98 30576 | 7/1998 |
| WO | WO-96 35412 | 8/1998 |
| WO | WO-98 33797 | 8/1998 |
| WO | WO-98 35020 | 8/1998 |
| WO | WO-98 57933 | 12/1998 |
| WO | WO-98 58650 | 12/1998 |
| WO | WO-99 52534 | 10/1999 |
| WO | WO-00 41545 | 7/2000 |
| WO | WO-00 74706 | 12/2000 |
| WO | WO 01 26644 | 4/2001 |
| WO | WO-01 27135 | 4/2001 |
| WO | WO-01 40438 | 6/2001 |
| WO | WO-01 98344 | 12/2001 |
| WO | WO-02 07702 | 1/2002 |
| WO | WO-02 30462 | 4/2002 |
| WO | WO-02 080952 | 10/2002 |

OTHER PUBLICATIONS

Gaffield et al., "Activating Smoothened mutations in sporadic basal-cell carcinoma" Nature (Jan. 1998) vol. 391 pp. 90-92.*
Adams et al., Evaluation of Arylmethylaminopropanediols by a Novel in Vitro Pharmacodynamic Assay: Correlation with Antitumor Activity in Vivo, Cancer Res, 1990, vol. 50, pp. 3663-3669.
Allen, M. et al., "Hedgehog signaling regulates sebaceous gland development," American Journal of Pathology, Dec. 2003, vol. 163, No. 6, pp. 2173-2178.
Ananthaswamy et al., "Detection and identification of activated oncogenes in human skin cancers occurring on sun-exposed body sites," Cancer Research, Jun. 15, 1988, vol. 48, pp. 3341-3346.
Athar, M. et al., "Inhibition of smoothened signaling prevents ultraviolet b-induced basal cell carcinomas through regulation of fas expression and apoptosis," Cancer Res, 2004, vol. 64, pp. 7545-7552.
Atta-Ur-Rahman et al., Alkaloids from *Veratrum album.* Phytochemistry, 1991, vol. 30, pp. 368-370.
Auerbach et al., "Regional differences in the incidence and growth of mouse tumors following intradermal or subcutaneous inoculation," Cancer Research, Jun. 1978, vol. 38, pp. 1739-1744.
Badria, F. A. et al., Time course and inhibition of stavaroside K, veratramin and corvine-induced hemolysis by other pregnane glycosides and Veratrum alkaloids, Pharmazie, 1995, vol. 50, pp. 421-423.
Baggiolini, E. et al., Photochemical Reactions: Photofragmentation of O-acetyljervine. Helvetica Chimica Acta, 1971, vol. 54, pp. 429-449—Abstract Only.
Bai Eta L., "All mouse ventral spinal cord patterning by hedgehog is Gli dependent and involves an activator function of GLI3," Development Cell, Jan. 2004, vol. 6, pp. 103-115.
Baker et al., "Lesions of potato sprout and extracted potato sprout alkaloid toxicity in Syrian hamsters," Clinical Toxicology, 1987, vol. 25, No. 3, pp. 199-208.
Barnes et al., "Patched1 interacts with cyclin B1 to regulate cell cycle pregression," The EMBO Journal, 2001, vol. 20, No. 9, pp. 2214-2223.
Basler, K. et al., "Compartment boundaries and the control of drosophila limb pattern by hedgehog protein," Nature, 1994, vol. 368, pp. 208-214.
Bavik, C. et. al., "Development abnormalities in cultured mouse embryos deprived of retinoic acid by inhibition of yolk sac retinol binding protein synthesis," Proceedings of the National Academy of the Sciences of USA 1996; 93: pp. 3110-3114.
Bellusci, S. et.al., "Involvement of Sonic hedgehog (Shh) in mouse embryonic lung growth and morphogenesis," Development 1997; 134: pp. 53-63.
Berman, D. M. et al., "Inhibition of prostate morphogensis by the sonic hedgehog pathway inhibitor cyclopamine," The Journal of Urology, Apr. 2000, vol. 163, No. 4.
Berman, D. M. et al., "Medulloblastoma growth inhibition by hedgehog pathway blockade," Science, Aug. 30, 2002, vol. 297, pp. 1559-1561.
Berman, D. M. et al., "Widespread requirement for hedgehog ligand stimulation in growth of digestive tract tumours," Nature, Oct. 23, 2003, vol. 425, pp. 846-851.
Bhattacharya, R. et al., "Role of hedgehog signaling in ovarian cancer," Clinical Cancer Research, 2008, vol. 14, pp. 7659-7666.
Bijlsma, M. F. et al., "Repression of smoothened by patched-dependent (Pro-)Vitamin D3 Secretion," Plos Biology, Aug. 2006, vol. 4, No. 8.
Birkeland, K. I. et al., Diabetic Medicine, 1998, vol. 15, S13-S19.
Braybrooke, J.P. et al., "A phase II study of razoxane, an antiangiogenic topoisomerase II inhibitor, in renal cell cancer with assessment of potential surrogate markers of angiogenesis," Clinical Cancer Research 2000; 6: pp. 4697-4704.
Brown, D. et al., "Structure-Activity Relation of Steroid Teratogens. II. N-substituted jervines," J. Agric. Food Chem., 1978, vol. 26, No. 3, pp. 564-566.
Brown, L.A. et al., "Insights into early vasculogenesis revealed by expression of the ETS-domain transcription factor Fli-1 in wild type and mutant zebrafish embryos," Mechanisms of Development 2000; 90: pp. 237-252.
Bucana et al., "Different patterns of macrophage infiltration into allogeneic-murine and xenogeneic-human neoplasms growing in nude mice," American Journal of Pathology, Nov. 1992, vol. 141, No. 5.
Campbell et al., "Inhibition of Limb Chondrogenesis by a Veratrum Alkaloid: Temporal Specificity in Vivo and in Vitro," Dev. Biol., 1985, vol. 111, pp. 464-470.
Cannavo, S. et al., Journal of Endocrinological Investigation, 1999, vol. 22, pp. 354-359.
Cao, Y. et al., "Neuropilin-1 upholds dedifferentiation and propagation phenotypes of renal cell carcinoma cells by activating akt and sonic hedgehog axes," Cancer Research, 2008, vol. 68, pp. 8667-8672.
Celso et al., "Transient activation of B-catenin signaling in adult mouse epidermis is sufficient to induce new hair follicles but continues activation is required to maintain hair follicle tumors," Development, 2004, vol. 131, pp. 1787-1799.

(56) References Cited

OTHER PUBLICATIONS

Chen et al., "Analysis of the zebrafish smoothened mutant reveals conserved and divergent functions of hedgehog activity," Development, 2001, vol. 128, pp. 2385-2396.

Chen, J. K. et al., "Inhibition of hedgehog signaling by direct binding of cyclopamine to smoothened," Genes & Development, 2002, vol. 16, pp. 2743-2748.

Chiang, C. et al., "Cyclopia and defective axial patterning in mice lacking sonic hedgehog gene function," Nature, 1996, vol. 383, pp. 407-413.

Chidambaram et al., Cancer Research, 1996, vol. 56, pp. 4599-4601.

Chiang, C. et al., Essential Role for Sonic hedgehog during Hair Follicle Morphogenesis. Developmental Biology, 1999, vol. 205, pp. 1-9.

Cooper, M. et al., Tetratogen-Mediated Inhibition of Target Tissue Response to Shh Signalling. Science, Jun. 1998, vol. 280, pp. 1603-1607.

Coventry et al., "Cyclopamine-induced holoprosencephaly and associated craniofacial malformations in the golden hamster: Anatomic and Molecular Events," Padiatric and Development Pathology, 1998, vol. 1, pp. 29-41.

Crawford, L. et al., A Preliminary Assessment of the Toxic and Mutagenic Potential of Steroidal Alkaloids in Transgenic Mice, 1995, Fd. Chem. Toxic, vol. 33, pp. 191-194.

D'Angelo, G. et al., "Camp-dependent protein kinase inhibits the mitogenic action of vascular endothelial growth factor and fibroblast growth factor in capillary endothelial cells by blocking Raf activation," Journal of Cell Biochemistry 1997; 6767: pp. 353-366.

Dahmane, N. et al., "Activation of the transcription factot Gil 1 and the Sonic hedgehog signaling pathway in skin tumours," Nature, Oct. 23, 1997, vol. 389, pp. 876-881.

Das Gupta et al., "A case study of the reproducibility of transcriptional reporter cell-based RNAi screens in Drosphila," Genome Biology, 2007, vol. 8, No. 9, Article R203.

De Boer et al., "Expression of Ep-CAM in Normal, Regenerating, Metaplastic and Neoplastic Liver," Journal of pathology, 1999, vol. 188, pp. 201-206.

De Jong et al., "No of apoptotic cells as a prognostic marker in invasive breast cancer," British Journal of Cancer, 2000, vol. 82, No. 2, pp. 368-373.

Decelis, J.F. et al., "Ventral veinless, the gene encoding the Cfla transcription factor, links positional information and cell differentiation during embryonic and imaginal development in Drosophila melanogaster," Development 1995; 121: pp. 3405-3416.

Declaration of Dr. Sinan Tas executed on Jul. 17, 2009.

Detmer, K. et al., "Erythroid differentiation in vitro is blocked by cyclopamine, an inhibitor of hedgehog signaling," Blood Cells, Molecules, and Disease, 2000, vol. 26, No. 4, pp. 360-372.

Dickson, M.G. Et. Al., "Defective haematopoiesis and vasculogenesis in transforming growth factor-beta 1 knock out mice," Development 1995; 121: pp. 1845-1854.

Diehl et al., "Glycogen synthase kinase-3b regulates cyclin D1 proteolysis and subcellular localization," Genes & Development, 1998, vol. 12, pp. 3499-3511.

Dunn, M.K. et al., "Cyclopamine, A Steroidal Alkaloid Disrupts Development of Neural Crest Cells in Xenopus," Developmental Dynamics 1995: 202: pp. 255-270.

Dyer, M. et al. "Indian hedgehog activities hematopoiesis and vasculogenesis and can respecify prospective neuroectodermal cell fate in the mouse embryo," Development 2001; 128: pp. 1717-1730.

Eichenmuller, M. et al., "Blocking the hedgehog pathway inhibits hepatoblastoma growth," Hepatology, 2009, vol. 49, pp. 482-490.

Ericson et al., "Two critical periods of sonic hedgehog signaling required for the specification of motor neuron identity," Cell, Nov. 15, 1996, vol. 87, pp. 661-673.

Espacenet—English Abstract of GB 1227728A—Apr. 7, 1971.

Essawi, et al., "Synthesis and Evaluation of 1- and 2-Substituted Fentanyl Analogues for Opioid Activity," J. Med. Chem. 26(3): pp. 348-352 (1983).

Fan, H. et al., "Sonic hedgehog opposes epithelial cell cycle arrest," the Journal of Cell Biology, Oct. 4, 1999, vol. 147, No. 1, pp. 71-76.

Farrington, S.M. et. al., "Hedgehog and Bmp genes are differentially expressed in distinct cell layers of the murine yolk sac," Mechanisms of Development 1997; 62: pp. 197-211.

Feng, Y. et al., "Overexpression of hedgehog signaling molecules and its involvement in the proliferation of endometrial carcinoma cells," Clinical Cancer Research, 2007, vol. 13, pp. 1389-1398.

Fleschar, M. H. et al., "Glossary of biotechnology terms," 1993, pp. 76-77.

Freestone, S. H. et al., "Sonic hedgehog regulates prostatic growth and epithelial differentiation," Developmental Biology, 2003, vol. 264, pp. 352-362.

Fujita, E. et al., "Involvement of sonic hedgehog in the cell growth of LK-2 cells, human lung squamous carcinoma cells," Biochem Biophys Res Commun, 1997, vol. 238, pp. 658-664.

Furumichi, T. et al., "3':5'-cyclic monophosphate inhibits in vitro angiogenesis induced by endothelial cell growth factor," Japanese Heart Journal 1992; 33: pp. 373-382.

Gaffield et al., "Craniofacial Malformation Induced in Hamsters by Steriodal Alkaloids," Journal of Natural Toxins, 1996, vol. 5, No. 1, pp. 25-38.

Gaffield, W. et al., Induction of Terata in Hamsters by Solanidane Alkaloids derived from Solanum tuberosum, Chem. Res. Toxicol., 1996, vol. 9, pp. 426-433.

Gaffield, W. et al., A looking glass perspective: Thalidomide and cyclopamine. Cell. And Mol. Biol., 1999, vol. 45, pp. 579-588.

Gailani et al., Development Genes and Cancer: Role of Patched in Basal Cell Carcinoma, J. Natl. Cancer Inst., 1997, vol. 89, No. 15, pp. 1103-1109.

Gerashchenko et al., "Antiinflammatory Activity of Jervine," Aktual Vop. Farm., 1970, pp. 169-171.

Gerashchenko, G. I. et al., Gluycocorticosteroidal Properties of Several Jervine Derivatives, Aktual. Vopr. Far., 1974, vol. 2, pp. 342-343—Abstract Only.

Goodrich et al., "Hedgehog and patched in neural development and disease," Neuron, Dec. 1998, vol. 21, pp. 1243-1257.

Grabel, L et al., "Using EC and ES cell culture to study early development: recent observations on Indian hedgehog and Bmps," International Journal of Development Biology 1998; 42: pp. 917-925.

Grachtchouk, M. et al., "Basal cell carcinomas in mice overexpressing Gli2 in skin," Nature Genetics, 2000, vol. 24, pp. 216-217.

Grachtchouk, V. et al., "The magnitude of hedgehog signaling activity defines skin tumor phenotype," The EMBO Journal, 2003, vol. 22, No. 11, pp. 2741-2751.

Guenthner, S. T. et al., "Cutaneous squamous cell carcinomas consistently show histologic evidence of in situ changes: A clinicopathologic correlation," J. Am. Acad. Dermatol., Sep. 1999, vol. 41, No. 3, pp. 443-448.

Hahn et al., Cell, 1996, vol. 85, pp. 841-851.

Hahn, H. et al., "The patched signaling pathway in tumorigenesis and development: lessons from animal models," J. Mol. Med., 1999, vol. 77, pp. 459-468.

Van Anna Maria De Schepop, H. et al., "Counting of apoptotic cells: a methodological study in invasive breast cancer," J. Clin. Pathol: Mol. Pathol., 1996, vol. 49, pp. M214-M217.

Heberlein, U. et al., "Growth and differentiation in the drosophila eye coordinated by hedgehog," Nature, 1995, vol. 373, pp. 709-711.

Hutchin, M. E. et al., "Sustained hedgehog signaling is required for basal cell carcinoma proliferation and survival: conditional skin tumorigenesis recapitulates the hair growth cycle," Genes & Development, 2005, vol. 19, pp. 214-223.

Incardona, J. P. et al., "The teratogenic veratrum alkaloid cyclopamine inhibits sonic hedgehog signal transduction," Development, 1998, vol. 125, pp. 3553-3562.

Ishizuya-Oka, A. et al., "Thyroid hormone-induced expression of sonic hedgehog correlates with adult epithelial development during remodeling of the Xenopus stomach and intestine," Differentiation, 2001, vol. 69, pp. 27-37.

Jackson, R. et al., "Elderly and sun-affected skins," Can Fam Physician, 2001, vol. 47, pp. 1236-1243.

(56) References Cited

OTHER PUBLICATIONS

Jarov, A. et al., "A dual role for sonic hedgehog in regulating adhesion and differentiation of neuroepithelial cell," Developmental Biology, 2003, vol. 261, pp. 520-536.

Jaye et al., "Expression of acidic fibroblast growth factor Cdna confers growth advantage and tumorigenesis to swiss 3T3 cells," The EMBO Journal, 1988, vol. 7, No. 4, pp. 963-969.

Jimenez et al., "Ber-EP4 Immunoreactivity in Normal skin and cutaneous neoplasms," Modern Pathology, 1995, vol. 8, No. 8, pp. 854-858.

Johnson et al., Science, 1996, vol. 272, pp. 1668-1671.

Johnson, R.L. et al., "Patched overexpression alters wing disc size and pattern: transcriptional and post-transcriptional effects on hedgehog targets," Development 1995; 121: pp. 4161-4170.

Jorns et al., "Comparative toxicity of alloxan, N-alkylalloxans and ninhydrin to isolated pancreatic islets in vitro," Journal of Endocrinology, 1997, vol. 155, pp. 283-293.

Kahane, N. et al., "The third wave of myotome colonization by mitolitcally competent progenitors: regulating the balance between differentiation and proliferation during muscle development," Development 2001, vol. 128, pp. 2187-2198.

Kaleagasioglu et al., "In Vitro evaluation of 1-(2-chloroethyl)-1-nitroso 3 (2-hydroxyethyl)urea linked to 4-acetoxy-bisdesmethyltamoxifen, estradiol and dihydrotestosterone," Arzneimittel-Forschung, 1990, vol. 40, No. 5, pp. 603-606.

Kampschmidt et al., "Acid hydrolase activity during the growth, necrosis, and regression of the Jensen Sarcoma," Cancer Research, Oct. 1968, vol. 28, pp. 1938-1943.

Katsuura, M. et al., "The NH2-terminal region of the active domain of sonic hedgehog is necessary for its signal transduction," FEBS Letters, 1999, vol. 447, pp. 325-328.

Keeler et al., Teratogenic compounds of Veratrum californicum (Durand). VII. The Structure of the glycosidic alkaloid cycloposine, Steroids, 1969, vol. 13, No. 5, pp. 579-588.

Kim. S. et al., "Pancreas development is promoted by cyclopamine, a hedgehog signaling inhibitor," Proc. Natl. Acad. Sci., USA, Oct. 1998, vol. 95, pp. 13036-13041.

Kojima, T. et al., "Induction of a mirror-image duplication of anterior wing structures by localized hedgehog expression in the anterior compartment of drosophila melanogaster wing imaginal discs," Gene, 1994, vol. 148, pp. 211-217.

Kooy, A. J. et al., Expression of E-Cadherin, .alpha.- & .beta.-catenin, and CD44V.sub.6 and the subcellular localization of E-cadherin and CD44V.sub.6 in normal epidermis and basal cell carcinoma, Human Pathology, Nov. 1999, vol. 30, No. 11, pp. 1328-1335.

Krauss, S. et al., "A functionally conserved homolg of the drosophila segment polarity gene hh is expressed in tissues with polarizing activity in zebra embryos," Cell, 1993, vol. 75, pp. 1431-1444.

Kubuschok et al., "Disseminated tumor cells in lymph nodes as a determinant for survival in surgically resected non-small-cell lung cancer," Journal of Clinical Oncology, 1999, vol. 17, No. 1, pp. 19-24.

Kutney et al., Synthetic Studies in the Veratrum Alkaloid Series II: The Total Synthesis of Verarine, Veratramine, Jervine, and Veratrobasine, Can. J. Chem., 1975, vol. 53, pp. 1976-1817.

Lepage, T. et al., "Signal transduction by Camp-dependent protein kinase A in drosophila limb patterning," Nature, 1995, vol. 373, pp. 711-715.

Levine, E. M. et al., "Sonic Hedgehog promotes rod photoreceptor differentiation in mammalian retinal cells in vitro," The Journal of Neuroscience, Aug. 15, 1997, vol. 17, No. 16, pp. 6277-6288.

Lewis et al., "Tumor induction by the c-Myc target genes rcl and Lactate dehydrogenase A," Cancer Research, Nov. 1, 2000, vol. 60, pp. 6178-6183.

Litingtung, Y. et al., "Sonic hedgehog is essential to foregut development," Nature Genetics 1998; 20: pp. 58-61.

Maye, P et al., "Indian hedgehog signaling in extraembryonic endoderm and ectoderm differentiation in ES embryoid bodies," Mechanisms of Development 2000; 94: pp. 117-132.

Methot et al., "An absolute requirement for Cubitus interruptus in Hedgehog signaling," Development, 2001, vol. 128, pp. 733-742.

Michimukai, E. et al., "Mutations in the human homologue of the drosophila segment polarity gene patched in oral squamous cell carcinoma cell lines," In Vitro Cellular & Developmental Biology, Jul./Aug. 2001, vol. 37, No. 7, pp. 459-464.

Mistretta, C. et al., Cyclopamine and jervine in embryonic rat tongue cultures demonstrate a role for Shh Signaling in taste papilla development and patterning fungiform papillai double in number and form in novel locations in dorsal lingual epithelium, Developmental Biology, 2003, vol. 254, pp. 1-18.

Mukherjee, S. et al., "Hedgehog signaling and response to cyclopamine differ in epithelial and stromal cells in benign breast and breast cancer," Cancer Biology & Therapy, Jun. 2006, vol. 5-6, pp. 674-683.

Perron, M. et al., "A novel function for hedgehog signaling in retinal pigment epithelium diffentiation," Development, 2003, vol. 130, pp. 1565-1577.

Nasevicius, A. et al., "Effective targeted gene 'knockdown' in zebrafish," Nature Genetics, 2000, vol. 26, vol. 26, pp. 216-220.

Niemann, C. et al., "Indian hedgehog and .beta.-catenin signaling: Role in the sebaceous lineage of normal and neoplastic mammalian epidermis," PNAS, Sep. 30, 2003, vol. 100, pp. 11873-11880.

Nilsson, M. et al., "Induction of basal cell carcinomas and trichoepitheliomas in mice overexpressing GLI-I," PNAS, Mar. 28, 2000, vol. 97, No. 7, pp. 3438-3443.

Omnell, M. L. et al., "Expression of veratrum alkaloid teratogenicity in the mouse," Teratology, 1990, pp. 105-119.

Orentas, D.M. et al., "Sonic hedgehog signaling is required during the appearance of spinal cord oligodendrocyte precursors," Development 1999; 126: pp. 2419-2429.

Oro, A. E. et al., "Basal cell carcinomas in mice overexpressing sonic hedgehog," Science, 1997, vol. 276, pp. 817-821.

Outram, S. V. et al., "Hedgehog signaling regulates differentiation from double-negative to double-postive thymocyte," Immunity, Aug. 2000, vol. 13, pp. 187-197.

Parker, S. P., McGraw-Hill Dictionary of Chemical Terms, 1985, pp. 218-219.

Pepicelli, C.V. et al., "Sonic hedgehog regulates branching morphogenesis in the mammalian lung," Current Biology 1998; 8: pp. 1083-1086.

Qualtrough, D. et al., "Hedgehog signaling in colorectal tumor cells: Induction of apoptosis with cyclopamine treatment," Int. J. Cancer, 2004, vol. 110, pp. 831-837.

Ramalho-Santos, M. et al., "Hedgehog signals regulate multiple aspects of gastrointestinal development," Development, vol. 127, pp. 2763-2772, (2000).

Riddle, R. D. et al., "Sonic hedgehog mediates polarizing activity of the ZPA," Cell, vol. 75, pp. 1401-1416, (1993).

Roberts, D.R. et al., "Sonic hedgehog is an endodermal signal inducing Bmp-4 and Hox genes during induction and regionalization of the chick hindgut," Development 1995; 121: 3163-3174.

Roessler, E. et al., "Mutations in the human sonic hedgehog gene cause holoprosencephaly," Nature Genentics, Nov. 1996, vol. 14, pp. 357-383.

Romer, J. T. et al., "Suppression of the Shh pathway using a small molecule inhibitor eliminates medulloblastoma in Ptc1p53−/− mice," Cancer Cell, Sep. 2004, vol. 6, pp. 229-240.

Sanchez, P. et al., "In vivo inhibition of endogenous brain tumors through systemic interference of hedgehog signaling in mice," Mechanisms of Development, 2005, vol. 122, pp. 223-230.

Sanwa Shiyouyaku KK, "New steroidal compound and carcinostatic agent," Patent Abstracts of Japan, Publication Date: Aug. 19, 1992; English Abstract of JP-04 230696.

Sauder, et al., "Neovastat (AE-941), an inhibitor of angiogenesis: Randomized phase I/II clinical trial results in patients with plaque psoriasis," J Am Acad Dermatol; vol. 47, No. 4, 2002; pp. 535-541.

Scales, S. J. et al., "Mechanisms of hedgehog pathway activation in cancer and implications for therapy," Trends in Pharmacological Sciences, vol. 30, No. 6, pp. 303-312, (2009).

(56) References Cited

OTHER PUBLICATIONS

Seno Kaoru et al., Espacenet—English Abstract of WO 98/33797A1—Aug. 6, 1998.
Smith, C. M. et al., 5x-Reductase Expression by Prostate Cancer Cell Lines and Benign Prostatic Hyperplasia in Vitro, J. Clin. Endo. and Metab., 1996, vol. 81, pp. 1361-1366.
Soignet, S. L. et al., New England Journal of Medicine, 1998, vol. 339, pp. 1341-1348.
St Amand, T.R. et al., "Cloning and expression pattern of chicken Pitx2: A new component in the Shh signaling pathway controlling embryonic heart looping," Biochemical and Biophysical Research Communications 1998; 247: pp. 100-105.
St Jacques, B et al., "Indian hedgehog signaling regulates proliferation and differentiation of chondrocytes and is essential for bone formation," Genes & Development 1999; 13: pp. 2072-2086.
Stamataki et al., "A gradient of gli activity mediates graded sonic hedgehog signaling in the neural tube," Genes & Development, 2005, vol. 19, pp. 626-641.
Stenkamp, D. L. et al., "Extraretinal and retinal hedgehog signaling sequentially regulate retinal differentiation in zebrafish," Departmental Biology, 2003, vol. 258, pp. 349-363.
Stenkamp, D. L. et al., "Function for hedgehog genes in zebrafish retinal development," Developmental Biology, 2000, vol. 220, pp. 238-252.
Sukegawa, A. et al., "The concentric structure of the developing gut is regulated by Sonic hedgehog derived from endodermal epithelium," Development, 2000, vol. 127, pp. 1971-1980.
Symmans, W. F. et al., "Paclitaxel-induced apoptosis and mitotic arrest assessed by serial fine-needle aspiration: Implications for early prediction of breast cancer response to neoadjuvant treatment," Clinical Cancer Research, Dec. 2000, vol. 6, pp. 4610-4617.
Taghian et al., "Quantitative comparison between the transplatability of human and murine tumors into the subcutaneous tissue of NCr/Sed-nu/nu nude and severe combined immunodeficient mice," Cancer Research, Oct. 1993, vol. 53, pp. 5012-5017.
Taipale et al., "Effects of oncogenic mutations in smoothened and patched can be reversed by cyclopamine," Nature, Aug. 31, 2000, vol. 406, No. 6799, pp. 1005-1009.
Takechi et al., "Structure-activity relationships of synthetic saponins," Phytochemistry, 1996, vol. 41, No. 1, pp. 121-123.
Tas, S. et al., "Induction of the differentiation and apoptosis of tumor cells in vivo with efficiency and selectivity," European Journal of Dermatology, 2004, vol. 14, pp. 96-102.
Tas, S. et al., "Rapid clearance of psoriatic skin lesions induced by topical cyclopamine," Dermatology 2004; 209; pp. 126-131.
Teglund, S. et al., "Hedgehog beyond medulloblastoma and basal cell carcinoma," Biochimica et Biophysica Acta, 2010, vol. 1805, pp. 181-208.
Tezuka et al., Two new steroidal alkaloids, 20-Isovertramine and Verapatuline, from the roots and Rhizomes of Veratrum patulum, J. Nat. Prod., 1998, vol. 61, pp. 1078-1081.
Thayer, S. P. et al., "Hedgehog is an early and late mediator of pancreatic cancer tumorigenesis," Nature, Oct. 23, 2003, vol. 425, pp. 851-856.
Tiet, T. D. et al., "Constitutive hedgehog signaling in chondrosarcoma up-regulates tumor cell proliferation," American Journal of Pathology, Jan. 1, 2006, vol. 168, No. 1, pp. 321-330.
Treier, M. et al., "Hedgehog signaling is required for pituitary gland development," Development, 2001, vol. 128, pp. 377-386.
Tsopanoglou, N.E. et al., "Opposing effects on modulation of angiogenesis by protein kinase C and Camp-mediated pathways," Journal of Vascular Research 1994; 31: 195-204.
Uhle et al., JACS, 1960, vol. 82, pp. 489-492.
Van Den Brink, G. R. et al., "Sonic hedgehog expression correlates with fundic gland differentiation in the adult gastrointestinal tract," Gut, 2002, vol. 51, pp. 628-633.
Van Den Brink, G. R. et al., "Sonic hedgehog regulates gastic gland morphogenesis in man and mouse," Gastroenterology, 2001, vol. 121, pp. 317-328.

Vila, G. et al., "Expression and function of sonic hedgehog pathway components in pituitary adenomas: Evidence for a direct role in hormone secretion," Journal of Clinical Endorcrinolgy & Metabolism, 2005, vol. 90, No. 12, pp. 6687-6694.
Vorechovshy, L. et al., "Trichoepitheliomas contain somatic mutations in the overexpressed PTCH Gene: Support for a gatekeeper Mechanism in skin tumorigenesis," Cancer Research, Nov. 1, 1997, vol. 57, pp. 4677-4681.
Wang et al., "Nuclear import of Cubitus interruptus is regulated by hedgehog via a mechanism distinct from Ci stabilization and Ci activation," Development, 2000, vol. 127, pp. 3131-3139.
Wang, B. et al., "Inhibition of epithelial ductal branching in the prostate by sonic hedgehog id indirectly mediated by stromal cells," The Journal of Biological Chemistry, May 16, 2003, vol. 278, No. 20, pp. 18506-18513.
Watkins, D. N. et al., "Hedgehog signaling within airway epithelial progenitors and in small-cell lung cancer," Nature, Mar. 20, 2003, vol. 422, pp. 131-317.
Wicking, C. et al., "The hedgehog signaling pathway in tumorigenesis and development," 1999, pp. 7844-7851.
Willingham, M. C. et al., "Cytochemical methods for the detection of apoptosis," the Journal of histochemistry and cytochemistry, 1999, vol. 47, pp. 1101-1109.
Wilson et al., "Malignant transformation of human fibroblasts by a transfected N-ras oncogene," Cancer Research, Sep. 1, 1990, vol. 50, pp. 5587-5593.
Winnier, G. et al., "Bone morphogenetic protein-4 is required for mesoderm formation and patterning in the mouse," Genes & Development 1995; 9: pp. 2105-2116.
Xiomara, Perez Gutierrez et al., Espacenet—English Abstract of WO 02/07702A2—Jan. 31, 2002.
Xu et al., "Genomewide expression profiling in the zebrafish embryo identifies target genes regulated by hedgehog signaling during vertebrate development," Genetics, Oct. 2006, vol. 174, pp. 735-752.
Hunnun, Y. A. et al., "Apoptosis and the dilemma of cancer chemotherapy," Blood, 1997, vol. 89, pp. 1845-1853.
Yao, H. et al., "Desert hedgehog/ patched 1 signaling specifies fetal leydig cell fate in testis organogenesis," Genes & Development, 2002, vol. 16, pp. 1433-1440.
Yashiro, K. et al., "Actinic keratoses arising only on sun-exposed vitiligo skin," Clinical and Experimental Dermatology, 1999, vol. 24, pp. 199-201.
Yoshimura, K. et al., "Usefulness of a narrow-band reflectance spectrophotometer in evaluating effects of depigmenting treatment," Aesth. Plast. Surg., 2001, vol. 25, pp. 125-133.
Zhang et al., "Effects of six steroidal saponins isolated from anemarrhenae rhizome on platelet aggregation and hemolysis in human blood," Clinica Chimica Acta, 1999, vol. 289, pp. 79-88.
Zhang, J. et al., "Downregulation of hedgehog signaling is required for organogenesis of the small intestine in Xenopus," Development Biology, 2001, vol. 229, pp. 188-202.
Zhang, Y. et al., "Hedgehog acts as a somatic stem cell factor in the drosophila ovary," Nature, Mar. 29, 2001, vol. 410, pp. 599-604.
Zietman et al., "Quantitative studies on the transplatability of murine and human tumors into the brain and subcutaneous tissue of NCr/Sed Nude Mice," Cancer Research, Nov. 15, 1988, vol. 48, pp. 6510-6516.
Thomson Innovation, "Skin whitening cosmetic containing jervine as active ingredient," Thomson Innovation Record View, Publication Date: Apr. 21, 2005; English Abstract of KR-2005 037103.
Keeler, R.F., "Teratogenic Compounds of Veratrum Californiucm (Durand)—VI. The Structure of Cyclopamine" Phytochemistry, 8:223-225 (1969).
Patent Abstracts of Japan, Publication No. 08-034742; Publication Date: Feb. 2, 1996; Application No: 06-318879; Filing Date: Dec. 21, 1994. Applicant: Wu Wencai.
Office Action with a notification date of Apr. 19, 2012 issued by the United States Patent and Trademark Office in U.S. Appl. No. 13/364,121 filed Feb. 1, 2012; Inventor: Philip A. Beachy.

* cited by examiner

REGULATORS OF THE HEDGEHOG PATHWAY, COMPOSITIONS AND USES RELATED THERETO

This application is a continuation U.S. application Ser. No. 12/079,776, filed Mar. 28, 2008, which is a continuation of U.S. application Ser. No. 11/338,503, filed Jan. 23, 2006, now U.S. Pat. No. 7,476,661, which is a continuation of U.S. application Ser. No. 09/688,076, filed Oct. 13, 2000, now U.S. Pat. No. 7,098,196, which claims the benefit of U.S. Provisional Application No. 60/159,215, filed Oct. 13, 1999, and No. 60/229,273, filed Aug. 30, 2000, the specifications of each of which are hereby incorporated by reference in their entirety; and this application also claims the benefit of U.S. application Ser. No. 13/364,161, filed Feb. 1, 2012, which is a continuation of U.S. application Ser. No. 12/652,134, filed on Jan. 5, 2010, which is a continuation of U.S. application Ser. No. 11/270,984, filed on Nov. 11, 2005, now abandoned, which is a divisional of U.S. application Ser. No. 09/708,964, filed on Nov. 8, 2000, now U.S. Pat. No. 7,291,626, which is a continuation of U.S. application Ser. No. 09/685,244, filed on Oct. 10, 2000, now abandoned, which is a continuation-in-part of PCT Application No. US 99/07811, filed on Apr. 9, 1999, which claims the benefit of U.S. Provisional Application Nos. 60/081,186, filed on Apr. 9, 1998, and 60/081,263, filed on Apr. 9, 1998, and which is a continuation-in-part of U.S. application Ser. No. 09/090,622, filed on Jun. 4, 1998, now U.S. Pat. No. 6,432,970, which also claims the benefit of U.S. Provisional Application No. 60/081,186, filed on Apr. 9, 1998; and is related to U.S. Ser. No. 11/894,712, filed on Aug. 20, 2007, now U.S. Pat. No. 8,097,632, and U.S. Ser. No. 09/708,974, filed on Nov. 8, 2000, now U.S. Pat. No. 6,867,216.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation (Davidson, E., (1990) *Development* 108: 365-389; Gurdon, J. B., (1992) *Cell* 68: 185-199; Jessell, T. M. et al., (1992) *Cell* 68: 257-270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68:185-199).

Members of the Hedgehog family of signaling molecules mediate many important short- and long-range patterning processes during invertebrate and vertebrate development. In the fly, a single hedgehog gene regulates segmental and imaginal disc patterning. In contrast, in vertebrates, a hedgehog gene family is involved in the control of left-right asymmetry, polarity in the CNS, somites and limb, organogenesis, chondrogenesis and spermatogenesis.

The first hedgehog gene was identified by a genetic screen in the fruitfly *Drosophila melanogaster* (Niisslein-Volhard, C. and Wieschaus, E. (1980) *Nature* 287, 795-801). This screen identified a number of mutations affecting embryonic and larval development. In 1992 and 1993, the molecular nature of the *Drosophila* hedgehog (hh) gene was reported (C. F., Lee et al. (1992) *Cell* 71, 33-50), and since then, several hedgehog homologues have been isolated from various vertebrate species. While only one hedgehog gene has been found in *Drosophila* and other invertebrates, multiple Hedgehog genes are present in vertebrates.

The vertebrate family of hedgehog genes includes at least four members, e.g., paralogs of the single *drosophila* hedgehog gene. Exemplary hedgehog genes and proteins are described in PCT publications WO 95/18856 and WO 96/17924. Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggy-winkle hedgehog (Twhh), appears specific to fish. Desert hedgehog (Dhh) is expressed principally in the testes, both in mouse embryonic development and in the adult rodent and human; Indian hedgehog (Ihh) is involved in bone development during embryogenesis and in bone formation in the adult; and, Shh, which as described above, is primarily involved in morphogenic and neuroinductive activities. Given the critical inductive roles of hedgehog polypeptides in the development and maintenance of vertebrate organs, the identification of hedgehog interacting proteins is of paramount significance in both clinical and research contexts.

The various Hedgehog proteins consist of a signal peptide, a highly conserved N-terminal region, and a more divergent C-terminal domain. In addition to signal sequence cleavage in the secretory pathway (Lee, J. J. et al. (1992) *Cell* 71:33-50; Tabata, T. et al. (1992) *Genes Dev.* 2635-2645; Chang, D. E. et al. (1994) *Development* 120:3339-3353), Hedgehog precursor proteins undergo an internal autoproteolytic cleavage which depends on conserved sequences in the C-terminal portion (Lee et al. (1994) *Science* 266:1528-1537; Porter et al. (1995) *Nature* 374: 363-366). This autocleavage leads to a 19 kD N-terminal peptide and a C-terminal peptide of 26-28 kD (Lee et al. (1992) supra; Chang et al. (1994) supra; Lee et al. (1994) supra; Bumcrot, D. A., et al. (1995) *Mol. Cell. Biol.* 15:2294-2303; Porter et al. (1995) supra; Ekker, S. C. et al. (1995) *Curr. Biol.* 5:944-955; Lai, C. J. et al. (1995) *Development* 121:2349-2360). The N-terminal peptide stays tightly associated with the surface of cells in which it was synthesized, while the C-terminal peptide is freely diffusible both in vitro and in vivo (Porter et al. (1995) *Nature* 374:363; Lee et al. (1994) supra; Bumcrot et al. (1995) supra; Marti, E. et al. (1995) *Development* 121:2537-2547; Roelink, H. et al. (1995) *Cell* 81:445-455). Interestingly, cell surface retention of the N-terminal peptide is dependent on autocleavage, as a truncated form of HH encoded by an RNA which terminates precisely at the normal position of internal cleavage is diffusible in vitro (Porter et al. (1995) supra) and in vivo (Porter, J. A. et al. (1996) *Cell* 86, 21-34). Biochemical studies have shown that the autoproteolytic cleavage of the HH precursor protein proceeds through an internal thioester intermediate which subsequently is cleaved in a nucleophilic substitution. It is likely that the nucleophile is a small lipophilic molecule which becomes covalently bound to the C-terminal end of the N-peptide (Porter et al. (1996) supra), tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short- and long-range Hedgehog signaling activities in *Drosophila* and vertebrates (Porter et al. (1995) supra; Ekker et al. (1995) supra; Lai et al. (1995) supra; Roelink, H. et al. (1995) *Cell* 81:445-455; Porter et al. (1996) supra; Fietz, M. J. et al. (1995) *Curr. Biol.* 5:643-651; Fan, C.-M. et al. (1995) *Cell* 81:457-465; Marti, E., et al. (1995) *Nature* 375:322-325; Lopez-Martinez et al. (1995) *Curr. Biol* 5:791-795; Ekker, S. C. et al. (1995) *Development* 121:2337-2347; Forbes, A. J. et al. (1996) *Development* 122:1125-1135).

HH has been implicated in short- and long-range patterning processes at various sites during *Drosophila* development. In the establishment of segment polarity in early embryos, it has short-range effects which appear to be directly mediated, while in the patterning of the imaginal discs, it induces long range effects via the induction of secondary signals.

In vertebrates, several hedgehog genes have been cloned in the past few years. Of these genes, Shh has received most of the experimental attention, as it is expressed in different organizing centers which are the sources of signals that pattern neighboring tissues. Recent evidence indicates that Shh is involved in these interactions.

The expression of Shh starts shortly after the onset of gastrulation in the presumptive midline mesoderm, the node in the mouse (Chang et al. (1994) supra; Echelard, Y. et al. (1993) *Cell* 75:1417-1430), the rat (Roelink, H. et al. (1994) *Cell* 76:761-775) and the chick (Riddle, R. D. et al. (1993) *Cell* 75:1401-1416), and the shield in the zebrafish (Ekker et al. (1995) supra; Krauss, S. et al. (1993) *Cell* 75:1431-1444). In chick embryos, the Shh expression pattern in the node develops a left-right asymmetry, which appears to be responsible for the left-right situs of the heart (Levin, M. et al. (1995) *Cell* 82:803-814).

In the CNS, Shh from the notochord and the floorplate appears to induce ventral cell fates. When ectopically expressed, Shh leads to a ventralization of large regions of the mid- and hindbrain in mouse (Echelard et al. (1993) supra; Goodrich, L. V. et al. (1996) *Genes Dev.* 10:301-312), *Xenopus* (Roelink, H. et al. (1994) supra; Ruiz i Altaba, A. et al. (1995) *Mol. Cell. Neurosci.* 6:106-121), and zebrafish (Ekker et al. (1995) supra; Krauss et al. (1993) supra; Hammerschmidt, M., et al. (1996) *Genes Dev.* 10:647-658). In explants of intermediate neuroectoderm at spinal cord levels, Shh protein induces floorplate and motor neuron development with distinct concentration thresholds, floor plate at high and motor neurons at lower concentrations (Roelink et al. (1995) supra; Marti et al. (1995) supra; Tanabe, Y. et al. (1995) *Curr. Biol.* 5:651-658). Moreover, antibody blocking suggests that Shh produced by the notochord is required for notochord-mediated induction of motor neuron fates (Marti et al. (1995) supra). Thus, high concentration of Shh on the surface of Shh-producing midline cells appears to account for the contact-mediated induction of floorplate observed in vitro (Placzek, M. et al. (1993) *Development* 117:205-218), and the midline positioning of the floorplate immediately above the notochord in vivo. Lower concentrations of Shh released from the notochord and the floorplate presumably induce motor neurons at more distant ventrolateral regions in a process that has been shown to be contact-independent in vitro (Yamada, T. et al. (1993) *Cell* 73:673-686). In explants taken at midbrain and forebrain levels, Shh also induces the appropriate ventrolateral neuronal cell types, dopaminergic (Heynes, M. et al. (1995) *Neuron* 15:35-44; Wang, M. Z. et al. (1995) *Nature Med.* 1:1184-1188) and cholinergic (Ericson, J. et al. (1995) *Cell* 81:747-756) precursors, respectively, indicating that Shh is a common inducer of ventral specification over the entire length of the CNS. These observations raise a question as to how the differential response to Shh is regulated at particular anteroposterior positions.

Shh from the midline also patterns the paraxial regions of the vertebrate embryo, the somites in the trunk (Fan et al. (1995) supra) and the head mesenchyme rostral of the somites (Hammerschmidt al. (1996) supra). In chick and mouse paraxial mesoderm explants, Shh promotes the expression of sclerotome specific markers like Pax1 and Twist, at the expense of the dermamyotomal marker Pax3. Moreover, filter barrier experiments suggest that Shh mediates the induction of the sclerotome directly rather than by activation of a secondary signaling mechanism (Fan, C.-M. and Tessier-Lavigne, M. (1994) *Cell* 79, 1175-1186).

Shh also induces myotomal gene expression (Hammerschmidt et al. (1996) supra; Johnson, R. L. et al. (1994) *Cell* 79:1165-1173; Miinsterberg, A. E. et al. (1995) *Genes Dev.* 9:2911-2922; Weinberg, E. S. et al. (1996) *Development* 122:271-280), although recent experiments indicate that members of the WNT family, vertebrate homologues of *Drosophila* wingless, are required in concert (Munsterberg et al. (1995) supra). Puzzlingly, myotomal induction in chicks requires higher Shh concentrations than the induction of sclerotomal markers (Munsterberg et al. (1995) supra), although the sclerotome originates from somitic cells positioned much closer to the notochord. Similar results were obtained in the zebrafish, where high concentrations of Hedgehog induce myotomal and repress sclerotomal marker gene expression (Hammerschmidt et al. (1996) supra). In contrast to amniotes, however, these observations are consistent with the architecture of the fish embryo, as here, the myotome is the predominant and more axial component of the somites. Thus, modulation of Shh signaling and the acquisition of new signaling factors may have modified the somite structure during vertebrate evolution.

In the vertebrate limb buds, a subset of posterior mesenchymal cells, the "Zone of polarizing activity" (ZPA), regulates anteroposterior digit identity (reviewed in Honig, L. S. (1981) *Nature* 291:72-73). Ectopic expression of Shh or application of beads soaked in Shh peptide mimics the effect of anterior ZPA grafts, generating a mirror image duplication of digits (Chang et al. (1994) supra; Lopez-Martinez et al. (1995) supra; Riddle et al. (1993) supra) (FIG. 2g). Thus, digit identity appears to depend primarily on Shh concentration, although it is possible that other signals may relay this information over the substantial distances that appear to be required for AP patterning (100-150 μm). Similar to the interaction of HH and DPP in the *Drosophila* imaginal discs, Shh in the vertebrate limb bud activates the expression of Bmp2 (Francis, P. H. et al. (1994) *Development* 120:209-218), a dpp homologue. However, unlike DPP in *Drosophila*, Bmp2 fails to mimic the polarizing effect of Shh upon ectopic application in the chick limb bud (Francis et al. (1994) supra). In addition to anteroposterior patterning, Shh also appears to be involved in the regulation of the proximodistal outgrowth of the limbs by inducing the synthesis of the fibroblast growth factor FGF4 in the posterior apical ectodermal ridge (Laufer, E. et al. (1994) *Cell* 79:993-1003; Niswander, L. et al. (1994) *Nature* 371:609-612).

The close relationship between Hedgehog proteins and BMPs is likely to have been conserved at many, but probably not all sites of vertebrate Hedgehog expression. For example, in the chick hindgut, Shh has been shown to induce the expression of Bmp4, another vertebrate dpp homologue (Roberts, D. J. et al. (1995) *Development* 121:3163-3174). Furthermore, Shh and Bmp2, 4, or 6 show a striking correlation in their expression in epithelial and mesenchymal cells of the stomach, the urogentital system, the lung, the tooth buds and the hair follicles (Bitgood, M. J. and McMahon, A. P. (1995) *Dev. Biol.* 172:126-138). Further, Ihh, one of the two other mouse Hedgehog genes, is expressed adjacent to Bmp expressing cells in the gut and developing cartilage (Bitgood and McMahon (1995) supra).

A major function of hedgehog in the *Drosophila* embryo is the maintenance of wg transcription at the boundary of each segmental unit (Hidalgo and Ingham, (1990) *Development* 110:291-302); from here, Wg protein diffuses across the segment to specify the character of the ectodermal cells that secrete the larval cuticle (Lawrence et al., (1996) *Development* 122:4095-4103). Like hh, mutations in three other segment polarity genes smoothened (smo), fused (fu) and cubitus interruptus (ci) eliminate wg transcription at parasegmental borders (Forbes et al., (1993) *Development Suppl.* 115-124; Ingham, (1993) *Nature* 366:560-562; Préat et al., (1993) *Genetics* 135:1047-1062; and van den Heuvel et al. (1996) *Nature* 382:547-551); by contrast, mutation of a fourth gene, patched (ptc), leads to the derepression of wg (Ingham et al., (1991) *Nature* 353:184-187; and Martinez Arias et al., (1988) *Development* 103:157-170). By making double mutant combinations between ptc and the other genes, it was established that smo, fu and ci all act downstream of ptc to activate wg transcription (Forbes et al., (1993) supra; Hooper (1994) *Nature* 372:461-464) whilst, on the other hand, transcription of wg becomes independent of hh in the absence of ptc (Ingham and Hidalgo (1993) *Development* 117:283-291). These findings suggest a simple pathway whereby hh acts to antagonize the activity of ptc which in turn antagonizes the activity of smo, fu and ci. The universality of this pathway subsequently has been established both in *Drosophila*, where ptc, smo, fu and ci mediate the activity of Hh in all processes studied to date (Ma et al., (1993) *Cell* 75:927-938); Chen et al. (1996) *Cell* 87:553-563; Forbes et al., (1996) *Development* 122:3283-3294; Sanchez-Herrero et al. (1996) *Mech. Dev.* 55:159-170; Strutt et al. (1997) *Development* 124:3233-3240), and in vertebrates, where homologues of ptc, smo and ci have been identified and implicated in processes mediated by one or other of the Hh family proteins (Concordet et al., (1996) *Development* 122:2835-2846; Goodrich et al., supra; Marigo et al., (1996) *Dev. Biol.* 180:273-283; Stone et al. (1996) *Nature* 384:129-134; Hynes et al. (1997) *Neuron* 19:15-26; and Quirk et al. (1997) *Cold Spring Harbor Symp. Quant. Biol.* 62:217-226).

Patched was originally identified in *Drosophila* as a segment polarity gene, one of a group of developmental genes that affect cell differentiation within the individual segments that occur in a homologous series along the anterior-posterior axis of the embryo. See Hooper, J. E. et al. (1989) *Cell* 59:751; and Nakano, Y. et al. (1989) *Nature* 341:508. Patterns of expression of the vertebrate homologue of patched suggest its involvement in the development of neural tube, skeleton, limbs, craniofacial structure, and skin. Another protein involved in hedgehog signaling emerged with the discovery that smoothened also encodes a transmembrane protein that is a member of the 7 transmembrane receptor (7™) family (Alcedo et al. (1996) *Cell* 86:221-232; van den Heuvel et al. supra). Human homologs of smo have been identified. See, for example, Stone et al. (1996) *Nature* 384:129-134, and GenBank accession U84401. In vitro binding assays have failed to detect any physical interaction between vertebrate Smo and Hh proteins (Stone et al., supra) whereas, under the same conditions, vertebrate Ptc binds the Sonic hedgehog (Shh) protein with relatively high affinity (Marigo et al. (1996) *Nature* 384:176-179; Stone et al., supra). Recently, it has been reported that activating smoothened mutations occur in sporadic basal cell carcinoma, Xie et al. (1998) *Nature* 391: 90-2, and primitive neuroectodermal tumors of the central nervous system, Reifenberger et al. (1998) *Cancer Res* 58: 1798-803.

The findings in the art suggest that Hh acts by binding to Ptc, thereby releasing an inhibitory effect of Ptc on Smo. Since Ptc and Smo are both transmembrane proteins, a proposed scenario is that they physically associate to form a receptor complex, though indirect mechanisms of action are also plausible. The derepression of Smo from Ptc inhibition most likely involves a conformational change in Smo. It is, however, important to remember that Ptc is not essential for Smo's activity, since Smo becomes constitutively activated in the complete absence of Ptc protein (Alcedo et al., supra; Quirk et al., supra).

It follows from the model that at least some loss-of-function mutations in ptc should act by disrupting binding to Smo. The discovery that mutations in the human ptc homolog are widespread in basal cell carcinomas (BCCs) (Hahn et al. (1996) *Cell* 85:841-851; Johnson et al. (1996) *Science* 272:1668-1671) has provided a major stimulation for the analysis of Ptc/Smo function as well as an abundant source of loss-of-function mutations. Many tumour-derived alleles of human ptc have now been sequenced, with the majority of the mutations characterized being due to premature termination of the coding region (Chidambaram et al. (1996) *Cancer Res.* 56:4599-4601; Wicking et al., (1997) *Am. J. Hum. Genet.* 60:21-26).

Disruption of Smo-Ptc binding could also be caused by mutations in smo; in contrast to ptc mutations, these should be dominantly acting (since they would lead to constitutive activity of the mutant protein). Recent studies of human BCCs have identified activating mutation(s) in Smo and appear to be responsible for the transformation of basal keratinocytes (Xie et al. (1998) *Nature* 391:90-92).

While not wishing to be bound by any particular theory, the emerging mechanism by which the smo-ptc pathway mediates signal transduction is as follows. In the absence of Hh induction, the activity of Smo is inhibited by Ptc probably through their physical association. Full-length Ci forms a complex with Fu, Cos-2 and suppressor-of-fused [Su(fu)], via which it associates with microtubules. This association leads to targeting of Ci to the proteasome where it is cleaved to release the transcriptional repressing form Ci75. The phosphorylation of Ci155 promotes its cleavage, either by promoting association with the Cos-2-Fu or by promoting ubiquitination (or both). When Hh binds to Ptc, the inhibitory effect on Smo is suppressed. The resulting activation of Smo leads to the dissociation of the Fu-Cos-2-Ci complex from microtubules. Cleavage of Ci155 is blocked; this or a related form of Ci then presumably enters the nucleus to activate transcription of ptc, gli and other target genes in association with CREB binding protein (CBP).

SUMMARY OF THE INVENTION

One aspect of the present invention makes available methods and reagents for inhibiting smoothened-dependent pathway activation. In certain embodiments, the subject methods can be used to counteract the phenotypic effects of unwanted activation of a hedgehog pathway, such as resulting from hedgehog gain-of-function, ptc loss-of-function or smoothened gain-of-function mutations. For instance, the subject method can involve contacting a cell (in vitro or in vivo) with a smoothened antagonist (defined infra), such as a steroidal alkaloid or other small molecule in an amount sufficient to antagonize a smoothened-dependent pathway activation.

Another aspect of the present invention makes available methods and reagents for activating smoothened-dependent pathway activation, e.g., to mimic all or certain of the effects that treatment with a hedgehog protein might cause. The subject method can involve contacting a cell (in vitro or in vivo) with a smoothened agonist (defined infra) in an amount sufficient to activate a smoothened-dependent pathway.

The subject methods and compounds may be used to regulate proliferation and/or differentiation of cells in vitro and/or in vivo, e.g., in the formation of tissue from stem cells, or to prevent the growth of hyperproliferative cells to illustrate but a few uses.

The subject compounds may be formulated as a pharmaceutical preparation comprising a pharmaceutically acceptable excipient. Smoothened antagonists of the invention and/or preparations comprising them may be administered to a patient to treat conditions involving unwanted cell proliferation, e.g., cancer and/or tumors (such as medulloblastoma, basal cell carcinoma, etc.), non-malignant hyperproliferative disorders, etc. Smoothened agonists can also be used to regulate the growth and differentiation of normal tissues. In certain embodiments, such compounds or preparations are administered systemically and/or locally, e.g., topically.

DETAILED DESCRIPTION OF THE INVENTION

I. Overview

Figure 1:
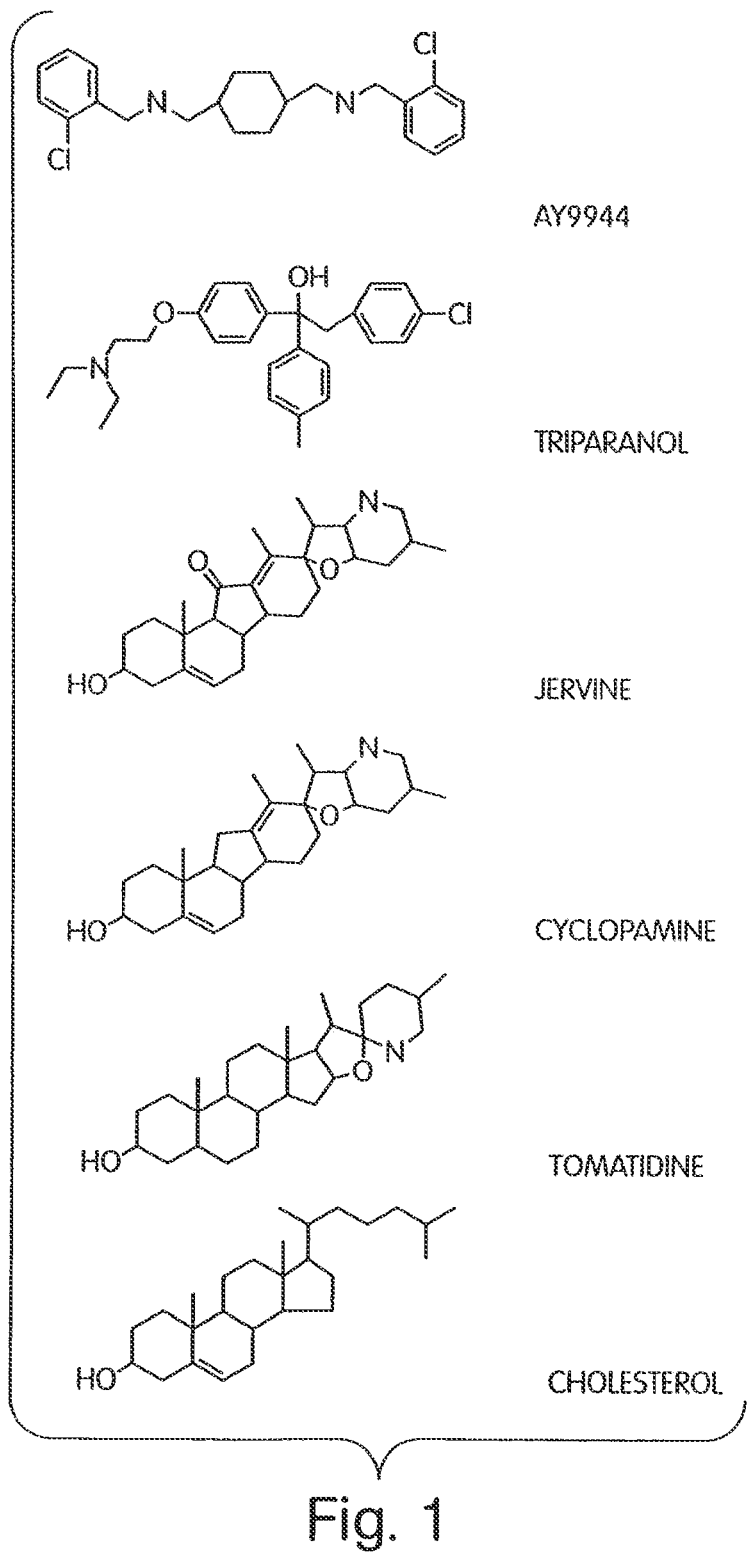
FIG. 1 presents structures of the synthetic compounds AY 9944 and triparanol, of the plant steriodal alkaloids jervine, cyclopamine, and tomatidine, and of cholesterol.

The present invention relates to the discovery that signal transduction pathways regulated by patched (ptc) and/or smoothened can be inhibited, at least in part, by steroidal alkaloids and analogs thereof. As set out in more detail below, we have observed that derivatives of cyclopamine can inhibit smoothened-dependent activity of the hedgehog pathway. While not wishing to be bound by any particular theory, our data indicates that cyclopamine acts at the level of smoothened, directly or indirectly shifting the steady-state ratio of active and inactive forms of smoothened towards the inactive form (e.g., relative to the absence of the steroidal alkaloid).

It is, therefore, specifically contemplated that other small molecules, steroidal and non-steroidal in structure, may similarly interfere with aspects of smoothened-mediated signal transduction. For instance, such compounds may be useful for inhibiting proliferation and/or inducing differentiation of normal tissues (e.g., tissues which express smo or are otherwise hedgehog-responsive). The subject smoothened antagonists may also be used to inhibit proliferation (or other biological consequences) in cells or tissues characterized as having a patched loss-of-function phenotype, a smoothened gain-of-function phenotype or a hedgehog gain-of-function phenotype.

It is also specifically contemplated that, in light of cyclopamine and other small molecules being able to inhibit smoothened-mediated signal transduction, that activators of smoothened-mediated signal transduction can be identified, e.g., compounds which directly or indirectly shift the steady-state ratio of active and inactive forms of smoothened towards the active form. Such compounds may be useful for, to illustrate, inducing proliferation and/or preventing differentiation of normal tissues (e.g., tissues which express smo or are otherwise hedgehog-responsive).

In preferred embodiments, the subject inhibitors and activators are organic molecules having a molecular weight less than 2500 amu, more preferably less than 1500 amu, and even more preferably less than 750 amu, and are capable of inhibiting at least some of the activity of a smoothened signal transduction pathway.

Thus, the methods of the present invention include the use of agents, such as small molecules, which antagonize or activate (as appropriate) smoothened-dependent activity of the hedgehog pathway, resulting in the regulation of repair and/or functional performance of a wide range of cells, tissues, and organs. For instance, the subject methods have therapeutic and cosmetic applications ranging from regulation of neural tissues, bone and cartilage formation and repair, regulation of spermatogenesis, regulation of smooth muscle, regulation of lung, liver, pancreas, and other organs arising from the primitive gut, regulation of hematopoietic function, regulation of skin and hair growth, etc. Moreover, the subject methods can be performed on cells which are provided in culture (in vitro), or on cells in a whole animal (in vivo). See, for example, PCT publications WO 95/18856 and WO 96/17924 (the specifications of which are expressly incorporated by reference herein).

In a certain preferred embodiment, the subject smoothened antagonists can be to treat epithelial cells having a phenotype of ptc loss-of-function, hedgehog gain-of-function, or smoothened gain-of-function employing an agent which antagonizes hedgehog function. For instance, the subject method can be used in treating or preventing basal cell carcinoma or other hedgehog pathway-related disorders.

In another preferred embodiment, the subject smoothened antagonists and activators can, as appropriate, be used to modulate proliferation or differentiation of pancreatic cells (e.g., ranging from pancreatic progenitor cells and mature endocrine or exocrine cells), or to regulate the growth or development of pancreatic tissue, e.g., in vivo or in vitro.

In yet another preferred embodiment, the subject method can be used as part of a treatment regimen for malignant medulloblastoma and other primary CNS malignant neuroectodermal tumors.

In another aspect, the present invention provides pharmaceutical preparations comprising, as an active ingredient, a smoothened antagonist or activator such as described herein, formulated in an amount sufficient to regulate, in vivo, a smoothened-dependent pathway, e.g., proliferation, differentiation or other biological consequences of normal or abnormal function of, for example, ptc, hedgehog or smoothened.

The subject treatments using the subject compounds can be effective for both human and animal subjects. Animal subjects to which the invention is applicable extend to both domestic animals and livestock, raised either as pets or for commercial purposes. Examples are dogs, cats, cattle, horses, sheep, hogs, and goats.

II. Definitions

For convenience, certain terms employed in the specification, examples, and appended claims are collected here.

The phrase "aberrant modification or mutation" of a gene refers to such genetic lesions as, for example, deletions, substitution or addition of nucleotides to a gene, as well as gross chromosomal rearrangements of the gene and/or abnormal methylation of the gene. Likewise, mis-expression of a gene refers to aberrant levels of transcription of the gene relative to those levels in a normal cell under similar conditions, as well as non-wild-type splicing of mRNA transcribed from the gene.

"Basal cell carcinomas" exist in a variety of clinical and histological forms such as nodular-ulcerative, superficial, pigmented, morphealike, fibroepithelioma and nevoid syndrome. Basal cell carcinomas are the most common cutaneous neoplasms found in humans. The majority of new cases of nonmelanoma skin cancers fall into this category.

"Burn wounds" refer to cases where large surface areas of skin have been removed or lost from an individual due to heat and/or chemical agents.

The term "cAMP regulator" refers to an agent which alters the level or activity of cAMP in a cell, including agents which act upon adenylate cyclase, cAMP phosphodiesterase, or other molecules which, in turn, regulate cAMP levels or activity. Additionally, cAMP regulators, as the term is used herein, refer to downstream effectors of cAMP activity, such as protein kinase A. "cAMP agonists" refers to that subset of cAMP regulators which increases the level or activity of cAMP in a cell, while "cAMP antagonists" refers to the subset which decreases the level or activity of cAMP in a cell.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Other carcinomatous epithelial growths are "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

The "corium" or "dermis" refers to the layer of the skin deep to the epidermis, consisting of a dense bed of vascular connective tissue, and containing the nerves and terminal organs of sensation. The hair roots, and sebaceous and sweat glands are structures of the epidermis which are deeply embedded in the dermis.

"Dental tissue" refers to tissue in the mouth which is similar to epithelial tissue, for example gum tissue. The method of the present invention is useful for treating periodontal disease.

"Dermal skin ulcers" refer to lesions on the skin caused by superficial loss of tissue, usually with inflammation. Dermal skin ulcers which can be treated by the method of the present invention include decubitus ulcers, diabetic ulcers, venous stasis ulcers and arterial ulcers. Decubitus wounds refer to chronic ulcers that result from pressure applied to areas of the skin for extended periods of time. Wounds of this type are often called bedsores or pressure sores. Venous stasis ulcers result from the stagnation of blood or other fluids from defective veins. Arterial ulcers refer to necrotic skin in the area around arteries having poor blood flow.

The term "$ED_{50}$" means the dose of a drug which produces 50% of its maximum response or effect.

An "effective amount" of a subject compound, with respect to the subject method of treatment, refers to an amount of the antagonist in a preparation which, when applied as part of a desired dosage regimen brings about, e.g., a change in the rate of cell proliferation and/or the state of differentiation of a cell and/or rate of survival of a cell according to clinically acceptable standards for the disorder to be treated or the cosmetic purpose.

The terms "epithelia", "epithelial" and "epithelium" refer to the cellular covering of internal and external body surfaces (cutaneous, mucous and serous), including the glands and other structures derived therefrom, e.g., corneal, esophogeal, epidermal, and hair follicle epithelial cells. Other exemplary epithelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, like that which is characteristically found lining hollow organs that are subject to great mechanical change due to contraction and distention, e.g., tissue which represents a transition between stratified squamous and columnar epithelium.

The term "epithelialization" refers to healing by the growth of epithelial tissue over a denuded surface.

The term "epidermal gland" refers to an aggregation of cells associated with the epidermis and specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface.

The term "epidermis" refers to the outermost and non-vascular layer of the skin, derived from the embryonic ectoderm, varying in thickness from 0.07-1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent.

"Excisional wounds" include tears, abrasions, cuts, punctures or lacerations in the epithelial layer of the skin and may extend into the dermal layer and even into subcutaneous fat and beyond. Excisional wounds can result from surgical procedures or from accidental penetration of the skin.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "hair" refers to a threadlike structure, especially the specialized epidermal structure composed of keratin and developing from a papilla sunk in the corium, produced only by mammals and characteristic of that group of animals. Also, "hair" may refer to the aggregate of such hairs. A "hair follicle" refers to one of the tubular-invaginations of the epidermis enclosing the hairs, and from which the hairs grow. "Hair follicle epithelial cells" refers to epithelial cells which surround the dermal papilla in the hair follicle, e.g., stem cells, outer root sheath cells, matrix cells, and inner root sheath cells. Such cells may be normal non-malignant cells, or transformed/immortalized cells.

The term "smoothened antagonist" refers to an agent which represses or induces transcription of target genes, e.g., gli1 and ptc genes, which in normal cells are induced or repressed by contact of the cell with hedgehog. In addition to altering a smoothened-dependent pathway, preferred smoothened antagonists can be used to overcome a ptc loss-of-function and/or a smoothened gain-of-function. The term "smoothened antagonist" as used herein also refers to any agent that may act by regulating a downstream effector of the smoothened pathway such as fused, suppressor of fused, cubitus interruptus, costal-2, etc., thereby inhibiting smoothened-dependent pathway activation.

The terms "loss-of-function" and "gain-of-function", as appropriate, refer to an aberrant modification or mutation of, e.g., a ptc gene, hedgehog gene, or smoothened gene, or a decrease or increase in the level of expression of such a gene, which results in a phenotype, e.g., which resembles contacting a cell with a hedgehog protein, such as aberrant activation of a hedgehog pathway or resemble loss of smo function. The mutation may include a loss of the ability of the ptc or smo gene product(s) to regulate the level of activity of Ci proteins, e.g., Gli1, Gli2, and Gli3.

As used herein, "immortalized cells" refers to cells which have been altered via chemical and/or recombinant means such that the cells have the ability to grow through an indefinite number of divisions in culture.

"Internal epithelial tissue" refers to tissue inside the body which has characteristics similar to the epidermal layer in the skin. Examples include the lining of the intestine. The method of the present invention is useful for promoting the healing of certain internal wounds, for example wounds resulting from surgery.

The term "keratosis" refers to proliferative skin disorder characterized by hyperplasia of the horny layer of the epidermis. Exemplary keratotic disorders include keratosis follicularis, keratosis palmaris et plantaris, keratosis pharyngea, keratosis pilaris, and actinic keratosis.

The term "$LD_{50}$" means the dose of a drug which is lethal in 50% of test subjects.

The term "nail" refers to the horny cutaneous plate on the dorsal surface of the distal end of a finger or toe.

A "patient" or "subject" to be treated by the subject method can mean either a human or non-human animal.

The term "prodrug" is intended to encompass compounds which, under physiological conditions, are converted into the therapeutically active agents of the present invention. A common method for making a prodrug is to include selected moieties which are hydrolyzed under physiological conditions to reveal the desired molecule. In other embodiments, the prodrug is converted by an enzymatic activity of the host animal.

As used herein, "proliferating" and "proliferation" refer to cells undergoing mitosis.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis. Another example is "epidermolysis", which refers to a loosened state of the epidermis with formation of blebs and bullae either spontaneously or at the site of trauma.

As used herein, the term "psoriasis" refers to a hyperproliferative skin disorder which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The term "therapeutic index" refers to the therapeutic index of a drug defined as $LD_{50}/ED_{50}$.

As used herein, "transformed cells" refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

The term "acylamino" is art-recognized and refers to a moiety that can be represented by the general formula:

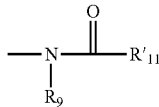

wherein $R_9$ is as defined above, and $R'_{11}$ represents a hydrogen, an alkyl, an alkenyl or $-(CH_2)_m-R_8$, wherein $R_8$ represents an aryl, a cycloalkyl, a cycloalkenyl, a heterocycle or a polycycle; and m is zero or an integer in the range of 1 to 8.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), $-CF_3$, $-CN$ and the like. Exemplary substituted alkyls are described below. Cycloalkyls can be further substituted with alkyls, alkenyls, alkoxys, alkylthios, aminoalkyls, carbonyl-substituted alkyls, $-CF_3$, $-CN$, and the like.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethylthio, and the like.

The terms "amine" and "amino" are art-recognized and refer to both unsubstituted and substituted amines, e.g., a moiety that can be represented by the general formula:

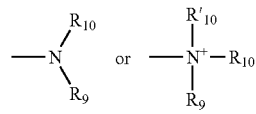

wherein $R_9$, $R_{10}$ and $R'_{10}$ each independently represent a hydrogen, an alkyl, an alkenyl, $-(CH_2)_m-R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or $-(CH_2)_m-R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

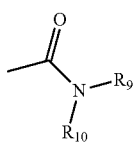

wherein $R_9$, $R_{10}$ are as defined above. Preferred embodiments of the amide will not include imides which may be unstable.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from heteroatoms (preferably 1 to 4), for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

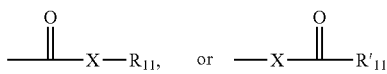

wherein X is a bond or represents an oxygen or a sulfur, and $R_{11}$ represents a hydrogen, an alkyl, an alkenyl, —(CH$_2$)$_m$—R$_8$ or a pharmaceutically acceptable salt, R'$_{11}$ represents a hydrogen, an alkyl, an alkenyl or —(CH$_2$)$_m$—R$_8$, where m and R$_8$ are as defined above. Where X is an oxygen and $R_{11}$ or R'$_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiocarbonyl" group. Where X is a sulfur and $R_{11}$ or R'$_{11}$ is not hydrogen, the formula represents a "thioester." Where X is a sulfur and $R_{11}$ is hydrogen, the formula represents a "thiocarboxylic acid." Where X is a sulfur and $R_{11}$' is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur and selenium.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

A "phosphonamidite" can be represented in the general formula:

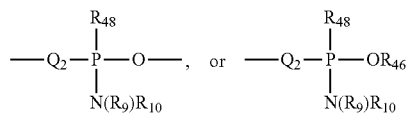

wherein $R_9$ and $R_{10}$ are as defined above, $Q_2$ represents O, S or N, and $R_{48}$ represents a lower alkyl or an aryl, $Q_2$ represents O, S or N.

A "phosphoramidite" can be represented in the general formula:

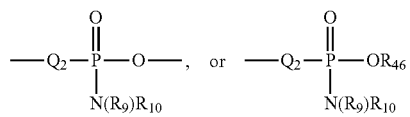

wherein $R_9$ and $R_{10}$ are as defined above, and $Q_2$ represents O, S or N.

A "phosphoryl" can in general be represented by the formula:

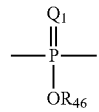

wherein $Q_1$ represented S or O, and $R_{46}$ represents hydrogen, a lower alkyl or an aryl. When used to substitute, for example, an alkyl, the phosphoryl group of the phosphorylalkyl can be represented by the general formula:

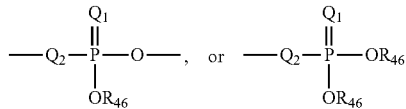

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

A "selenoalkyl" refers to an alkyl group having a substituted seleno group attached thereto. Exemplary "selenoethers" which may be substituted on the alkyl are selected from one of –Se-alkyl, –Se-alkenyl, –Se-alkynyl, and –Se—$(CH_2)_m$—$R_8$, m and $R_8$ being defined above.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

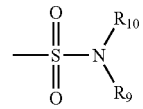

in which $R_9$ and $R_{10}$ are as defined above.

The term "sulfate" is art recognized and includes a moiety that can be represented by the general formula:

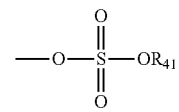

in which $R_{41}$ is as defined above.

The term "sulfonamido" is art recognized and includes a moiety that can be represented by the general formula:

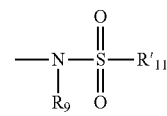

in which $R_9$ and $R'_{11}$ are as defined above.

The term "sulfonate" is art-recognized and includes a moiety that can be represented by the general formula:

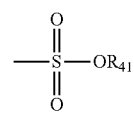

in which $R_{41}$ is an electron pair, hydrogen, alkyl, cycloalkyl, or aryl.

The terms "sulfoxido" or "sulfinyl", as used herein, refers to a moiety that can be represented by the general formula:

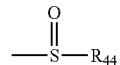

in which $R_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., the ability to inhibit hedgehog signaling), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

III. Exemplary Compounds of the Invention

As described in further detail below, it is contemplated that the subject methods can be carried out using any of a variety of different steroidal alkaloids which can be readily identified, e.g., by such drug screening assays as described herein. Steroidal alkaloids have a fairly complex nitrogen-containing nucleus. Two exemplary classes of steroidal alkaloids for use in the subject methods are the *Solanum* type and the *Veratrum* type. The above notwithstanding, in a preferred embodiment, the methods and compositions of the present invention make use of compounds having a steroidal alkaloid ring system of cyclopamine.

There are more than 50 naturally occurring *veratrum* alkaloids including veratramine, cyclopamine, cycloposine, jervine, and muldamine occurring in plants of the *Veratrum* spp. The *Zigadenus* spp., death camas, also produces several *veratrum*-type of steroidal alkaloids including zygacine. In general, many of the *veratrum* alkaloids (e.g., jervine, cyclopamine and cycloposine) consist of a modified steroid skeleton attached spiro to a furanopiperidine. A typical *veratrum*-type alkaloid may be represented by:

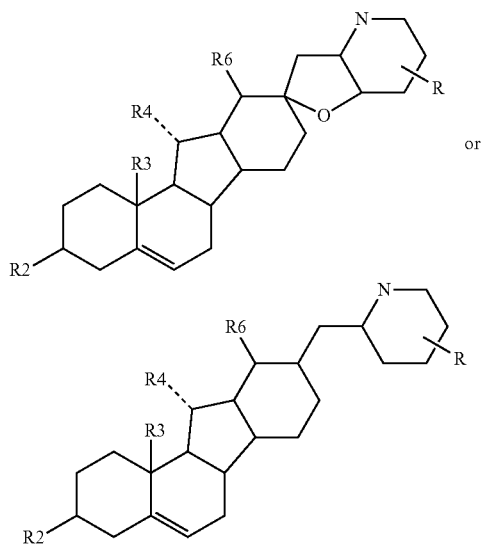

An example of the *Solanum* type is solanidine. This steroidal alkaloid is the nucleus (i.e., aglycone) for two important glycoalkaloids, solanine and chaconine, found in potatoes. Other plants in the *Solanum* family including various nightshades, Jerusalem cherries, and tomatoes also contain *solanum*-type glycoalkaloids. Glycoalkaloids are glycosides of alkaloids. A typical *solanum*-type alkaloid may be represented by:

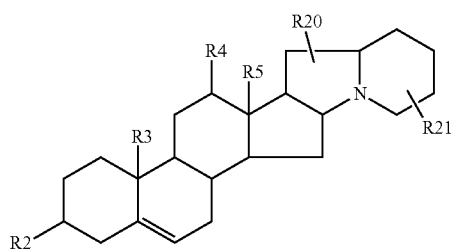

Based on these structures, and the possibility that certain unwanted side effects can be reduced by some manipulation of the structure, a wide range of steroidal alkaloids are contemplated as potential smoothened antagonists for use in the subject method. For example, compounds useful in the subject methods include steroidal alkaloids represented in the general formulas (I), or unsaturated forms thereof and/or seco-, nor- or homo-derivatives thereof:

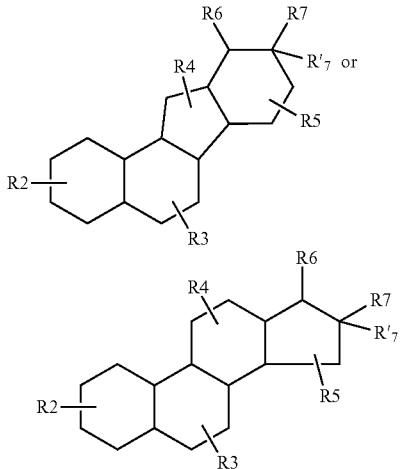

Formula I wherein, as valence and stability permit, $R_2$ and $R_3$ represent one or more substitutions to the ring to which each is attached, for each occurrence, independently represent hydrogen, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, sugar (e.g., monosaccharide, disaccharide, polysaccharide, etc.), carbamate (e.g., attached to the steroid at oxygen), carbonate, or —$(CH_2)_m$—$R_8$;

$R_4$ and $R_5$, independently for each occurrence, are absent or represent one or more substitutions to the ring to which each is attached, selected from hydrogen, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, sugar, carbamate, carbonate, or —$(CH_2)_m$—$R_8$;$R_6$, $R_7$, and $R'_7$, are absent or represent, independently, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$, or $R_6$ and $R_7$, or $R_7$ and $R'_7$, taken together form a ring or polycyclic ring, e.g., which is substituted or unsubstituted, with the proviso that at least one of $R_6$, $R_7$, or $R'_7$ is present and includes an amine, e.g., as one of the atoms which makes up the ring;

$R_8$ represents an aryl, a cycloalkyl, a cycloalkenyl, a heterocycle, or a polycycle; and m is an integer in the range 0 to 8 inclusive.

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain embodiments, the amine of $R_6$, $R_7$, or $R'_7$ is a tertiary amine.

In particular embodiments, $R_3$, for each occurrence, is an —OH, alkyl, —O-alkyl, —C(O)-alkyl, or —C(O)—$R_8$.

In particular embodiments, $R_4$, for each occurrence, is an absent, or represents —OH, =O, alkyl, —O-alkyl, —C(O)-alkyl, or —C(O)—$R_8$.

In particular embodiments, two of $R_6$, $R_7$, and $R'_7$ taken together form a nitrogen-containing ring, such as a furanopiperidine, such as perhydrofuro[3,2-b]pyridine, a pyranopiperidine, a quinoline, an indole, a pyranopyrrole, a naphthyridine, a thiofuranopiperidine, or a thiopyranopiperidine.

In certain embodiments, the nitrogen-containing ring comprises a tertiary amine, e.g., by having an extraannular substituent on the nitrogen atom, e.g., an alkyl substituted with, for example, aryl, aralkyl, heteroaryl, heteroaralkyl, amide, acylamino, carbonyl, ester, carbamate, urea, ketone, sulfonamide, etc. In certain embodiments, the extraannular substituent of the tertiary amine is a hydrophobic substituent. In certain embodiments, the hydrophobic extraannular substituent includes an aryl, heteroaryl, carbocyclyl, heterocyclyl, or polycyclyl group, such as biotin, a zwitterionic complex of boron, a steroidal polycycle, etc. In certain embodiments, the hydrophobic substituent may consist essentially of a combination of alkyl, amido, acylamino, ketone, ester, ether, halogen, alkenyl, alkynyl, aryl, aralkyl, urea, or similar functional groups, including between 5 and 40 non-hydrogen atoms, more preferably between 5 and 20 non-hydrogen atoms.

In particular embodiments, $R_8$ represents an aryl, a cycloalkyl, a cycloalkenyl, a heterocycle, or a polycycle, and preferably $R_8$ is a piperidine, pyrrolidine, pyridine, pyrimidine, morpholine, thiomorpholine, pyridazine, etc.

In certain embodiments, $R_2$ represents =O, sugar, carbamate, ester, carbonate, or alkoxy; $R_3$, for each occurrence, is an —OH, alkyl, —O-alkyl, —C(O)-alkyl, or —C(O)—$R_8$; $R_4$, for each occurrence, is absent, or represents —OH, =O, alkyl, —O-alkyl, —C(O)-alkyl, or —C(O)—$R_8$; and $R_5$, for each occurrence, is absent, or represents —OH, =O, or alkyl.

In certain preferred embodiments, the definitions outlined above apply, and the subject compounds are represented by general formula Ia or unsaturated forms thereof and/or seco-, nor- or homo-derivatives thereof:

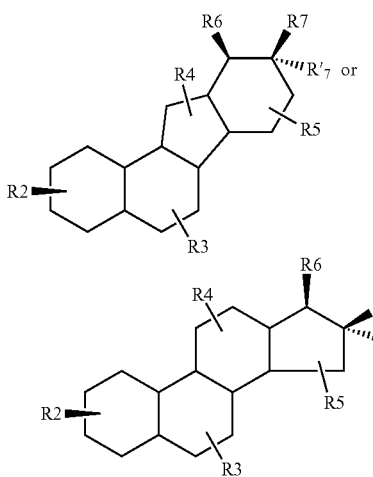

Formula Ia

In certain embodiments, the steroidal alkaloid is represented in the general formula (II), or unsaturated forms thereof and/or seco-, nor- or homo-derivatives thereof:

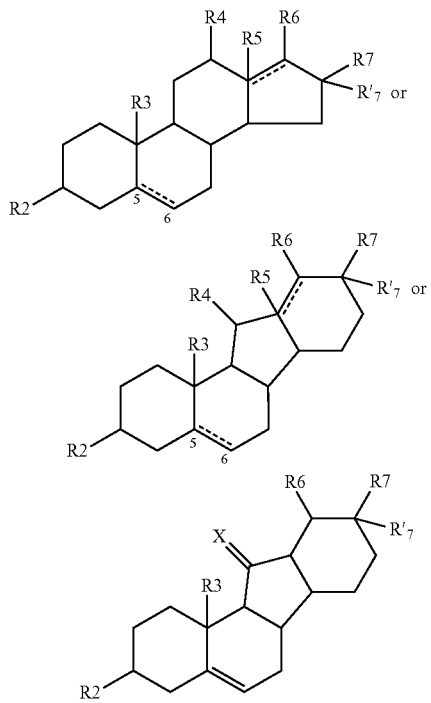

Formula II wherein $R_2$, $R_3$, $R_4$, $R_5$, $R_6$, $R_7$, and $R'_7$ are as defined above, and X represents O or S, though preferably O.

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain embodiments, the amine of $R_6$, $R_7$, or $R'_7$ is a tertiary amine, e.g., substituted with a substituted or unsubstituted alkyl. In certain embodiments, the amine is part of a bicyclic ring system formed from $R_7$ and $R'_7$, e.g., a furanopiperidine system, and the third substituent is an alkyl substituted with, for example, aryl, aralkyl, heteroaryl, heteroaralkyl, amide, acylamino, carbonyl, ester, carbamate, urea, ketone, sulfonamide, etc. In certain embodiments, the extraannular substituent of the tertiary amine is a hydrophobic substituent. In certain embodiments, the hydrophobic extraannular substituent includes an aryl, heteroaryl, carbocyclyl, heterocyclyl, or polycyclyl group, such as biotin, a zwitterionic complex of boron, a steroidal polycycle, etc. In certain embodiments, the hydrophobic substituent may consist essentially of a combination of alkyl, amido, acylamino, ketone, ester, ether, halogen, alkenyl, alkynyl, aryl, aralkyl, urea, or similar functional groups, including between 5 and 40 non-hydrogen atoms, more preferably between 5 and 20 non-hydrogen atoms.

In certain embodiments, $R_2$ represents =O, sugar, carbamate, ester, carbonate, or alkoxy; $R_3$, for each occurrence, is an —OH, alkyl, —O-alkyl, —C(O)-alkyl, or —C(O)—$R_8$; $R_4$, for each occurrence, is absent, or represents —OH, =O, alkyl, —O-alkyl, —C(O)-alkyl, or —C(O)—$R_8$; and $R_5$, for each occurrence, is absent, or represents —OH, =O, or alkyl.

In certain preferred embodiments, the definitions outlined above apply, and the subject compounds are represented by general formula IIa or unsaturated forms thereof and/or seco-, nor- or homo-derivatives thereof:

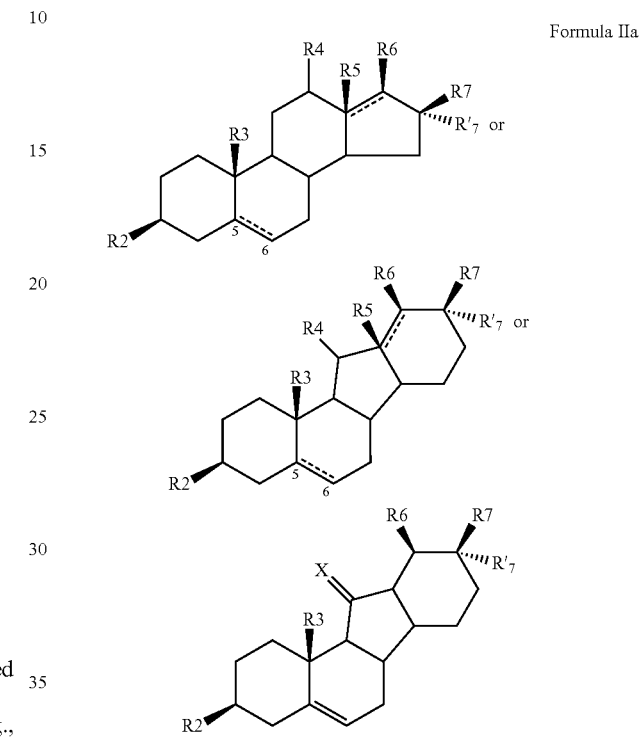

Formula IIa

In certain embodiments, the steroidal alkaloid is represented in the general formula (III), or unsaturated forms thereof and/or seco-, nor- or homo-derivatives thereof:

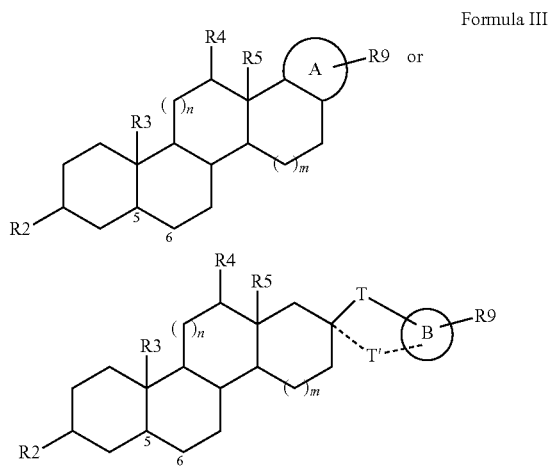

Formula III wherein
$R_2$, $R_3$, $R_4$, $R_5$ and $R_8$ are as defined above;
A and B represent monocyclic or polycyclic groups;
T represents an alkyl, an aminoalkyl, a carboxyl, an ester, an amide, ether or amine linkage of 1-10 bond lengths;

T' is absent, or represents an alkyl, an aminoalkyl, a carboxyl, an ester, an amide, ether or amine linkage of 1-3 bond lengths, wherein if T and T' are present together, than T and T' taken together with the ring A or B form a covalently closed ring of 5-8 ring atoms;

$R_9$ represents one or more substitutions to the ring A or B, which for each occurrence, independently represent halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$; and n and m are, independently, zero, 1 or 2;

with the proviso that A, or T, T', and B, taken together, include at least one amine.

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain embodiments, the amine of A, or T, T', and B, is a tertiary amine, e.g., substituted with a substituted or unsubstituted alkyl, e.g., substituted with aryl, aralkyl, heteroaryl, heteroaralkyl, amide, acylamino, carbonyl, ester, carbamate, urea, ketone, sulfonamide, etc. In certain embodiments, the extraannular substituent of the tertiary amine is a hydrophobic substituent. In certain embodiments, the hydrophobic extraannular substituent includes an aryl, heteroaryl, carbocyclyl, heterocyclyl, or polycyclyl group, such as biotin, a zwitterionic complex of boron, a steroidal polycycle, etc. In certain embodiments, the hydrophobic substituent may consist essentially of a combination of alkyl, amido, acylamino, ketone, ester, ether, halogen, alkenyl, alkynyl, aryl, aralkyl, urea, or similar functional groups, including between 5 and 40 non-hydrogen atoms, more preferably between 5 and 20 non-hydrogen atoms.

In certain embodiments, $R_2$ represents =O, sugar, carbamate, ester, carbonate, or alkoxy; $R_3$, for each occurrence, is an —OH, alkyl, —O-alkyl, —C(O)-alkyl, or —C(O)—$R_8$; $R_4$, for each occurrence, is absent, or represents —OH, =O, alkyl, —O-alkyl, —C(O)-alkyl, or —C(O)—$R_8$; and $R_5$, for each occurrence, is absent, or represents —OH, =O, or alkyl.

In certain preferred embodiments, the definitions outlined above apply, and the subject compounds are represented by general formula IIIa or unsaturated forms thereof and/or seco-, nor- or homo-derivatives thereof:

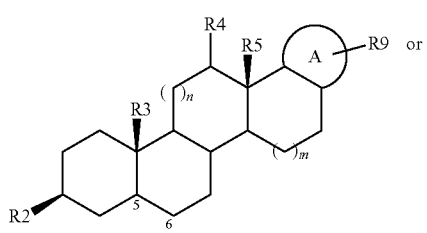

Formula IIIa

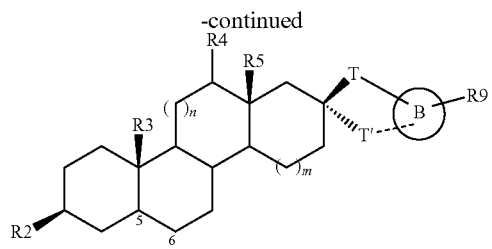

For example, the subject methods can utilize smoothened antagonists based on the *veratrum*-type steroidal alkaloids jervine, cyclopamine, cycloposine, mukiamine or veratramine, e.g., which may be represented in the general formula (IV), or unsaturated forms thereof and/or seco-, nor- or homo-derivatives thereof:

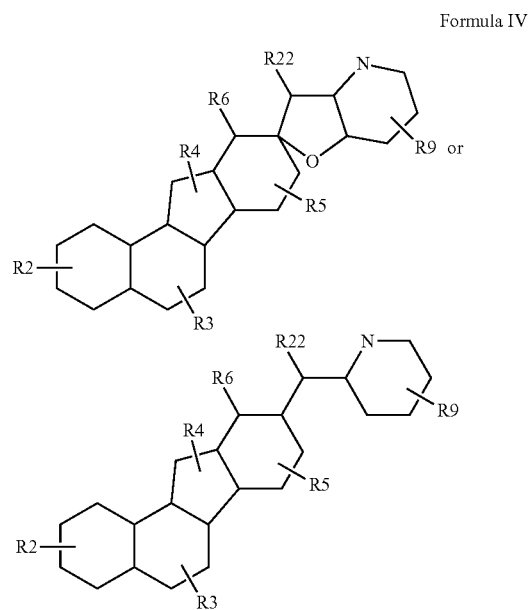

Formula IV wherein $R_2$, $R_3$, $R_4$, $R_5$, $R_6$ and $R_9$ are as defined above;

$R_{22}$ is absent or represents an alkyl, an alkoxyl or —OH.

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain embodiments, $R_9$ includes a substituent on nitrogen, e.g., a substituted or unsubstituted alkyl, e.g., substituted with, for example, aryl, aralkyl, heteroaryl, heteroaralkyl, amide, acylamino, carbonyl, ester, carbamate, urea, ketone, sulfonamide, etc. In certain embodiments, the extraannular substituent (e.g., $R_9$) of the tertiary amine is a hydrophobic substituent. In certain embodiments, the hydrophobic extraannular substituent includes an aryl, heteroaryl, carbocyclyl, heterocyclyl, or polycyclyl group, such as biotin, a zwitterionic complex of boron, a steroidal polycycle, etc. In certain embodiments, the hydrophobic substituent may consist essentially of a combination of alkyl, amido, acylamino, ketone, ester, ether, halogen, alkenyl, alkynyl, aryl, aralkyl, urea, or similar functional groups, including between 5 and 40 non-hydrogen atoms, more preferably between 5 and 20 non-hydrogen atoms.

In certain embodiments, $R_2$ represents =O, sugar, carbamate, ester, carbonate, or alkoxy; $R_3$, for each occurrence, is an —OH, alkyl, —O-alkyl, —C(O)-alkyl, or —C(O)—$R_8$; $R_4$, for each occurrence, is absent, or represents —OH, =O, alkyl, —O-alkyl, —C(O)-alkyl, or —C(O)—$R_8$; and $R_5$, for each occurrence, is absent, or represents —OH, =O, or alkyl.

In certain preferred embodiments, the definitions outlined above apply, and the subject compounds are represented by general formula IVa or unsaturated forms thereof and/or seco-, nor- or homo-derivatives thereof:

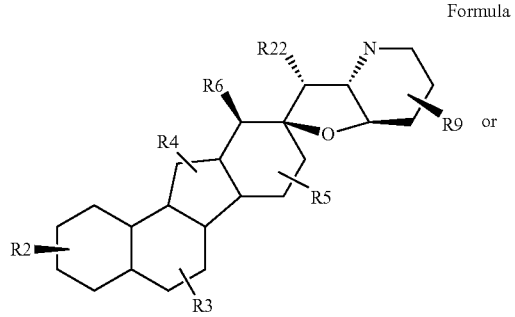

Formula IVa

In certain embodiments, the steroidal alkaloid is represented in the general formula (V) or unsaturated forms thereof and/or seco-, nor- or homo-derivatives thereof:

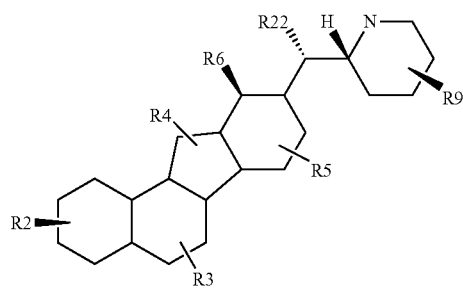

Formula V

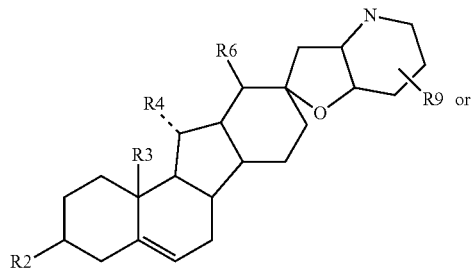

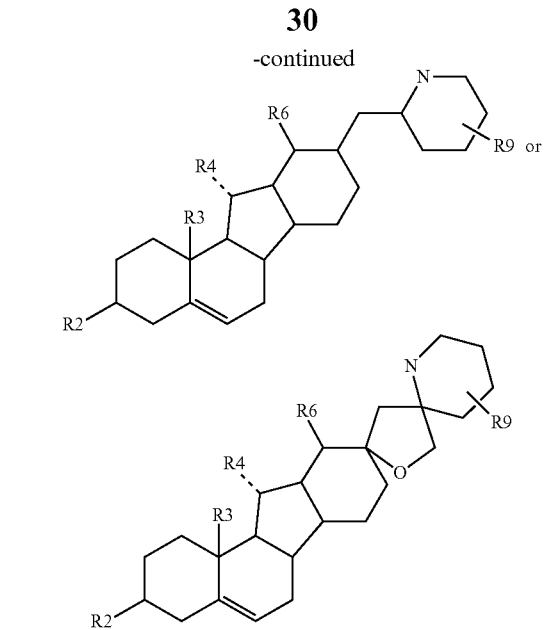

wherein $R_2$, $R_3$, $R_4$, $R_6$ and $R_9$ are as defined above;

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain embodiments, $R_9$ includes a substituent on nitrogen, e.g., a substituted or unsubstituted alkyl, e.g., substituted with, for example, aryl, aralkyl, heteroaryl, heteroaralkyl, amide, acylamino, carbonyl, ester, carbamate, urea, ketone, sulfonamide, etc.

In certain embodiments, the extraannular substituent of the tertiary amine (e.g., $R_9$) is a hydrophobic substituent. In certain embodiments, the hydrophobic extraannular substituent includes an aryl, heteroaryl, carbocyclyl, heterocyclyl, or polycyclyl group, such as biotin, a zwitterionic complex of boron, a steroidal polycycle, etc. In certain embodiments, the hydrophobic substituent may consist essentially of a combination of alkyl, amido, acylamino, ketone, ester, ether, halogen, alkenyl, alkynyl, aryl, aralkyl, urea, or similar functional groups, including between 5 and 40 non-hydrogen atoms, more preferably between 5 and 20 non-hydrogen atoms.

In certain preferred embodiments, the definitions outlined above apply, and the subject compounds are represented by general formula Va or unsaturated forms thereof and/or seco-, nor- or homo-derivatives thereof:

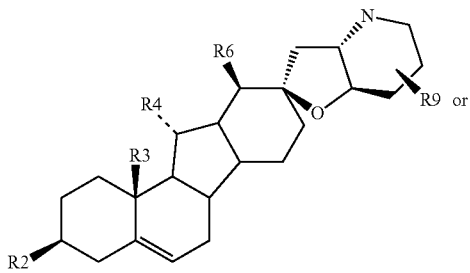

Formula Va

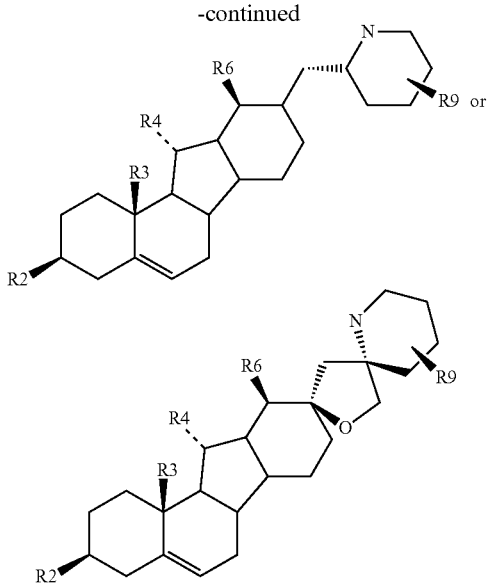

Another class of smoothened antagonists can be based on the *veratrum*-type steroidal alkaloids resmebling verticine and zygacine, e.g., general formula (VI), or unsaturated forms thereof and/or seco-, nor- or homo-derivatives thereof:

Formula VI

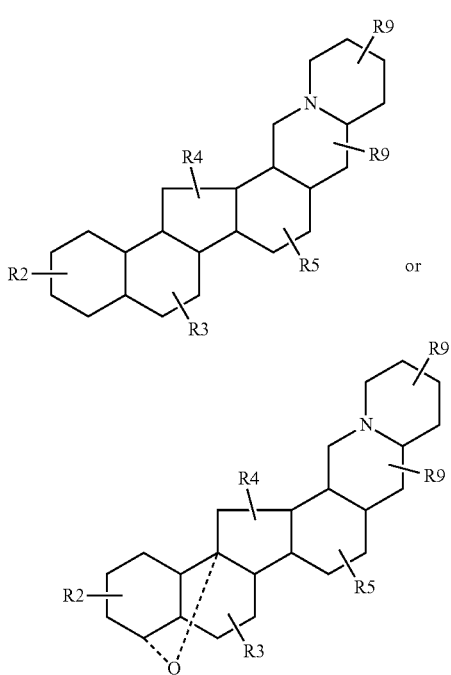

wherein $R_2$, $R_3$, $R_4$, $R_5$ and $R_9$ are as defined above;

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain preferred embodiments, the definitions outlined above apply, and the subject compounds are represented by general formula VIa or unsaturated forms thereof and/or seco-, nor- or homo-derivatives thereof:

Formula VIa

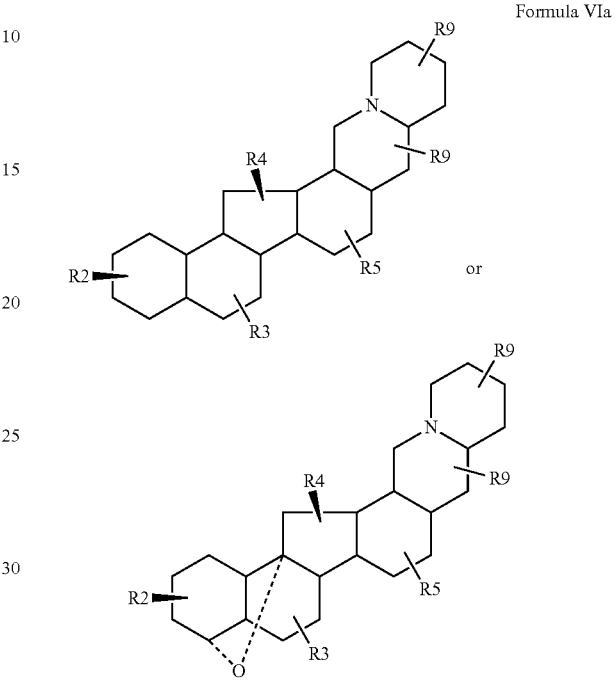

In certain embodiments, the steroidal alkaloid is represented in the general formula (VII) or unsaturated forms thereof and/or seco-, nor- or homo-derivatives thereof:

Formula VII

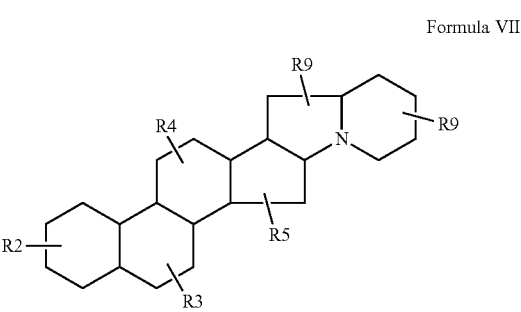

wherein $R_2$, $R_3$, $R_4$, $R_5$ and $R_9$ are as defined above.

In certain embodiments, $R_2$ represents =O, sugar (e.g., monosaccharide, disaccharide, polysaccharide, etc.), carbamate (e.g., attached to the steroid at oxygen), ester (e.g., attached to the steroid at oxygen), carbonate, or alkoxy. Substituents such as carbamate, ester, carbonate, and alkoxy may be substituted or unsubstituted, e.g., may include additional functional groups such as aryl, aralkyl, heteroaryl, heteroaralkyl, amide, acylamino, carbonyl, ester, carbamate, urea, ketone, sulfonamide, etc.

In certain preferred embodiments, the definitions outlined above apply, and the subject compounds are represented by general formula VIIa or unsaturated forms thereof and/or seco-, nor- or homo-derivatives thereof:

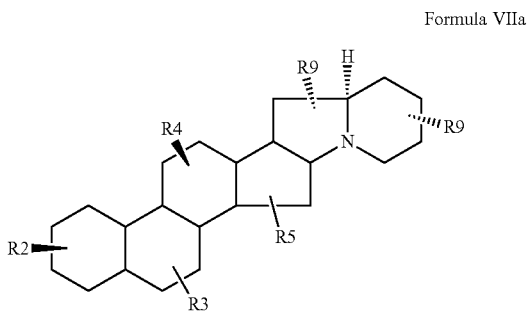

Formula VIIa

In certain embodiments, the subject antagonists and activators can be chosen on the basis of their selectively for the smoothened pathway. This selectivity can be for the smoothened pathway versus other steroid-mediated pathways (such as testosterone or estrogen mediated activities), as well as selectivity for particular hedgehog/ptc/smoothened pathways, e.g., which isotype specific for ptc (e.g., ptc-1, ptc-2) or hedgehog (e.g., Shh, Ihh, Dhh, etc). For instance, the subject method may employ steroidal alkaloids which do not substantially interfere with the biological activity of such steroids as aldosterone, androstane, androstene, androstenedione, androsterone, cholecalciferol, cholestane, cholic acid, corticosterone, cortisol, cortisol acetate, cortisone, cortisone acetate, deoxycorticosterone, digitoxigenin, ergocalciferol, ergosterol, estradiol-17-α, estradiol-17-β, estriol, estrane, estrone, hydrocortisone, lanosterol, lithocholic acid, mestranol, β-methasone, prednisone, pregnane, pregnenolone, progesterone, spironolactone, testosterone, triamcinolone and their derivatives, at least so far as those activities are unrelated to ptc related signaling.

In one embodiment, the subject steroidal alkaloid for use in the present method has a $k_d$ for members of the nuclear hormone receptor superfamily of greater than 1 μM, and more preferably greater than 1 mM, e.g., it does not bind estrogen, testosterone receptors or the like. Preferably, the subject smoothened antagonist has no estrogenic activity at physiological concentrations (e.g., in the range of 1 ng-1 mg/kg).

In this manner, untoward side effects which may be associated certain members of the steroidal alkaloid class can be reduced. For example, using the drug screening assays described herein, the application of combinatorial and medicinal chemistry techniques to the steroidal alkaloids provides a means for reducing such unwanted negative side effects including personality changes, shortened life spans, cardiovascular diseases and vascular occlusion, organ toxicity, hyperglycemia and diabetes, Cushnoid features, "wasting" syndrome, steroidal glaucoma, hypertension, peptic ulcers, and increased susceptibility to infections. For certain embodiments, it will be benefical to reduce the teratogenic activity relative to jervine, as for example, in the use of the subject method to selectively inhibit spermatogenesis.

In a preferred embodiment, the subject antagonists are steroidal alkaloids other than spirosolane, tomatidine, jervine, etc.

In particular embodiments, the steroidal alkaloid is chosen for use because it is more selective for one patched isoform over the next, e.g., 10-fold, and more preferably at least 100- or even 1000-fold more selective for one patched pathway (ptc-1, ptc-2) over another. Likewise, the steroidal alkaloid may be chosen for use because it is more selective for one smoothened isoform over the next, e.g., 10-fold, and more preferably at least 100- or even 1000-fold more selective for one wild-type smoothened protein (should various isoforms exist) or for activated smoothened mutants relative to wild-type smoothened. In certain embodiments, the subject method can be carried out conjointly with the administration of growth and/or trophic factors, or compositions which also act on other parts of the hedgehog/smoothened pathway. For instance, it is contemplated that the subject methods can include treatment with an agent that modulates cAMP levels, e.g., increasing or decreasing intracellular levels of cAMP.

In one embodiment, the subject method utilizes a smoothened antagonist, and the conjoint agent elevates cAMP levels in order to enhance the efficacy of the smoothened antagonist.

For example, compounds which may activate adenylate cyclase include forskolin (FK), cholera toxin (CT), pertussis toxin (PT), prostaglandins (e.g., PGE-1 and PGE-2), colforsin and β-adrenergic receptor agonists. β-Adrenergic receptor agonists (sometimes referred to herein as "β-adrenergic agonists") include albuterol, bambuterol, bitolterol, carbuterol, clenbuterol, clorprenaline, denopamine, dioxethedrine, dopexamine, ephedrine, epinephrine, etafedrine, ethylnorepinephrine, fenoterol, formoterol, hexoprenaline, ibopamine, isoetharine, isoproterenol, mabuterol, metaproterenol, methoxyphenamine, norepinephrine, oxyfedrine, pirbuterol, prenalterol, procaterol, propranolol, protokylol, quinterenol, reproterol, rimiterol, ritodrine, salmefamol, soterenol, salmeterol, terbutaline, tretoquinol, tulobuterol, and xamoterol.

Compounds which may inhibit a cAMP phosphodiesterase include aminone, milrinone, xanthine, methylxanthine, anagrelide, cilostamide, medorinone, indolidan, rolipram, 3-isobutyl-1-methylxanthine (IBMX), chelerythrine, cilostazol, glucocorticoids, griseolic acid, etazolate, caffeine, indomethacin, papverine, MDL 12330A, SQ 22536, GDPssS, clonidine, type III and type IV phosphodiesterase inhibitors, methylxanthines such as pentoxifylline, theophylline, theobromine, pyrrolidinones and phenyl cycloalkane and cycloalkene derivatives (described in PCT publications Nos. WO 92/19594 and WO 92/10190), lisophylline, and fenoxamine.

Analogs of cAMP which may be useful in the present method include dibutyryl-cAMP (db-cAMP), (8-(4)-chlorophenylthio)-cAMP (cpt-cAMP), 8-[(4-bromo-2,3-dioxobutyl)thio]-cAMP, 2-[(4-bromo-2,3-dioxobutyl)thio]-cAMP, 8-bromo-cAMP, dioctanoyl-cAMP, Sp-adenosine 3':5'-cyclic phosphorothioate, 8-piperidino-cAMP, $N^6$-phenyl-cAMP, 8-methylamino-cAMP, 8-(6-aminohexyl)amino-cAMP, 2'-deoxy-cAMP, $N^6$,2'-O-dibutryl-cAMP, $N^6$,2'-O-disuccinyl-cAMP, $N^6$-monobutyryl-cAMP, 2'-β-monobutyryl-cAMP, 2'-O-monobutryl-8-bromo-cAMP, $N^6$-monobutryl-2'-deoxy-cAMP, and 2'-O-monosuccinyl-cAMP.

Compounds which may reduce the levels or activity of cAMP include prostaglandylinositol cyclic phosphate (cyclic PIP), endothelins (ET)-1 and -3, norepinepurine, K252a, dideoxyadenosine, dynorphins, melatonin, pertussis toxin, staurosporine, $G_i$ agonists, MDL 12330A, SQ 22536, GDPssS and clonidine, beta-blockers, and ligands of G-protein coupled receptors. Additional compounds are disclosed in U.S. Pat. Nos. 5,891,875, 5,260,210, and 5,795,756.

Above-listed compounds useful in the subject methods may be modified to increase the bioavailability, activity, or other pharmacologically relevant property of the compound. For example, forskolin has the formula:

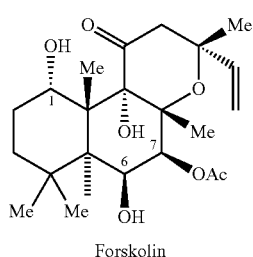

Forskolin

Modifications of forskolin which have been found to increase the hydrophilic character of forskolin without severely attenuating the desired biological activity include acylation of the hydroxyls at C6 and/or C7 (after removal of the acetyl group) with hydrophilic acyl groups. In compounds wherein C6 is acylated with a hydrophilic acyl group, C7 may optionally be deacetylated. Suitable hydrophilic acyl groups include groups having the structure —(CO)(CH$_2$)$_n$X, wherein X is OH or NR$_2$; R is hydrogen, a C$_1$-C$_4$ alkyl group, or two Rs taken together form a ring comprising 3-8 atoms, preferably 5-7 atoms, which may include heteroatoms (e.g., piperazine or morpholine rings); and n is an integer from 1-6, preferably from 1-4, even more preferably from 1-2. Other suitable hydrophilic acyl groups include hydrophilic amino acids or derivatives thereof, such as aspartic acid, glutamic acid, asparagine, glutamine, serine, threonine, tyrosine, etc., including amino acids having a heterocyclic side chain. Forskolin, or other compounds listed above, modified by other possible hydrophilic acyl side chains known to those of skill in the art may be readily synthesized and tested for activity in the present method.

Similarly, variants or derivatives of any of the above-listed compounds may be effective as cAMP antagonists in the subject method, e.g., in order to decrease cAMP levels and potentiate the activity of a smoothened activator. Those skilled in the art will readily be able to synthesize and test such derivatives for suitable activity.

IV. Exemplary Applications of Method and Compositions

One aspect of the present invention relates to a method of modulating a differentiated state, survival, and/or proliferation of a cell, such as a normal cell or a cell having a ptc loss-of-function, hedgehog gain-of-function, or smoothened gain-of-function, by contacting the cells with a compound as set forth above according to the subject method and as the circumstances may warrant.

For instance, it is contemplated by the invention that, in light of the findings of an apparently broad involvement of hedgehog, ptc, and smoothened in the formation of ordered spatial arrangements of differentiated tissues in vertebrates, the subject method could be used as part of a process for generating and/or maintaining an array of different vertebrate tissue both in vitro and in vivo. The compound, whether inductive or anti-inductive with respect to proliferation or differentiation of a given tissue, can be, as appropriate, any of the preparations described above.

For example, the present method of using subject compounds is applicable to cell culture techniques wherein it is desirable to control the proliferation or differentiation of the cell. A subject compound may be employed in a method directed towards cells which have a ptc loss-of-function, hedgehog gain-of-function, or smoothened gain-of-function phenotype. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). One use of the present method may be in cultures of neuronal stem cells, such as in the use of such cultures for the generation of new neurons and glia. In such embodiments of the subject method, the cultured cells can be contacted with a compound of the present invention in order to alter the rate of proliferation of neuronal stem cells in the culture and/or alter the rate of differentiation, or to maintain the integrity of a culture of certain terminally differentiated neuronal cells. In an exemplary embodiment, the subject method can be used to culture, for example, sensory neurons or, alternatively, motorneurons. Such neuronal cultures can be used as convenient assay systems as well as sources of implantable cells for therapeutic treatments.

According to the present invention, large numbers of non-tumorigenic neural progenitor cells can be perpetuated in vitro and their rate of proliferation and/or differentiation can be affected by contact with compounds of the present invention. Generally, a method is provided comprising the steps of isolating neural progenitor cells from an animal, perpetuating these cells in vitro or in vivo, preferably in the presence of growth factors, and regulating the differentiation of these cells into particular neural phenotypes, e.g., neurons and glia, by contacting the cells with a subject compound.

Progenitor cells are thought to be under a tonic inhibitory influence which maintains the progenitors in a suppressed state until their differentiation is required. However, recent techniques have been provided which permit these cells to be proliferated, and unlike neurons which are terminally differentiated and therefore non-dividing, they can be produced in unlimited number and are highly suitable for transplantation into heterologous and autologous hosts with neurodegenerative diseases.

By "progenitor" it is meant an oligopotent or multipotent stem cell which is able to divide without limit and, under specific conditions, can produce daughter cells which terminally differentiate such as into neurons and glia. These cells can be used for transplantation into a heterologous or autologous host. By heterologous is meant a host other than the animal from which the progenitor cells were originally derived. By autologous is meant the identical host from which the cells were originally derived.

Cells can be obtained from embryonic, post-natal, juvenile or adult neural tissue from any animal. By any animal is meant any multicellular animal which contains nervous tissue. More particularly, is meant any fish, reptile, bird, amphibian or mammal and the like. The most preferable donors are mammals, especially mice and humans.

In the case of a heterologous donor animal, the animal may be euthanized, and the brain and specific area of interest removed using a sterile procedure. Brain areas of particular interest include any area from which progenitor cells can be obtained which will serve to restore function to a degenerated area of the host's brain. These regions include areas of the central nervous system (CNS) including the cerebral cortex, cerebellum, midbrain, brainstem, spinal cord and ventricular tissue, and areas of the peripheral nervous system (PNS) including the carotid body and the adrenal medulla. More particularly, these areas include regions in the basal ganglia, preferably the striatum which consists of the caudate and putamen, or various cell groups such as the globus pallidus, the subthalamic nucleus, the nucleus basalis which is found to be degenerated in Alzheimer's Disease patients, or the substantia nigra pars compacta which is found to be degenerated in Parkinson's Disease patients.

Human heterologous neural progenitor cells may be derived from fetal tissue obtained from elective abortion, or from a post-natal, juvenile or adult organ donor. Autologous neural tissue can be obtained by biopsy, or from patients undergoing neurosurgery in which neural tissue is removed, in particular during epilepsy surgery, and more particularly during temporal lobectomies and hippocampalectomies.

Cells can be obtained from donor tissue by dissociation of individual cells from the connecting extracellular matrix of the tissue. Dissociation can be obtained using any known procedure, including treatment with enzymes such as trypsin, collagenase and the like, or by using physical methods of dissociation such as with a blunt instrument or by mincing with a scalpel to a allow outgrowth of specific cell types from a tissue. Dissociation of fetal cells can be carried out in tissue culture medium, while a preferable medium for dissociation of juvenile and adult cells is artificial cerebral spinal fluid (aCSF). Regular aCSF contains 124 mM NaCl, 5 mM KCl, 1.3 mM $MgCl_2$, 2 mM $CaCl_2$, 26 mM $NaHCO_3$, and 10 mM D-glucose. Low $Ca^{2+}$ aCSF contains the same ingredients except for $MgCl_2$ at a concentration of 3.2 mM and $CaCl_2$ at a concentration of 0.1 mM.

Dissociated cells can be placed into any known culture medium capable of supporting cell growth, including MEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. A particularly preferable medium for cells is a mixture of DMEM and F-12.

Conditions for culturing should be close to physiological conditions. The pH of the culture media should be close to physiological pH, preferably between pH 6-8, more preferably close to pH 7, even more particularly about pH 7.4. Cells should be cultured at a temperature close to physiological temperature, preferably between 30° C.-40° C., more preferably between 32° C.-38° C., and most preferably between 35° C.-37° C.

Cells can be grown in suspension or on a fixed substrate, but proliferation of the progenitors is preferably done in suspension to generate large numbers of cells by formation of "neurospheres" (see, for example, Reynolds et al. (1992) Science 255:1070-1709; and PCT Publications WO93/01275, WO94/09119, WO94/10292, and WO94/16718). In the case of propagating (or splitting) suspension cells, flasks are shaken well and the neurospheres allowed to settle on the bottom corner of the flask. The spheres are then transferred to a 50 ml centrifuge tube and centrifuged at low speed. The medium is aspirated, the cells resuspended in a small amount of medium with growth factor, and the cells mechanically dissociated and resuspended in separate aliquots of media.

Cell suspensions in culture medium are supplemented with any growth factor which allows for the proliferation of progenitor cells and seeded in any receptacle capable of sustaining cells, though as set out above, preferably in culture flasks or roller bottles. Cells typically proliferate within 3-4 days in a 37° C. incubator, and proliferation can be reinitiated at any time after that by dissociation of the cells and resuspension in fresh medium containing growth factors.

In the absence of substrate, cells lift off the floor of the flask and continue to proliferate in suspension forming a hollow sphere of undifferentiated cells. After approximately 3-10 days in vitro, the proliferating clusters (neurospheres) are fed every 2-7 days, and more particularly every 2-4 days by gentle centrifugation and resuspension in medium containing growth factor.

After 6-7 days in vitro, individual cells in the neurospheres can be separated by physical dissociation of the neurospheres with a blunt instrument, more particularly by triturating the neurospheres with a pipette. Single cells from the dissociated neurospheres are suspended in culture medium containing growth factors, and differentiation of the cells can be control in culture by plating (or resuspending) the cells in the presence of a subject compound.

To further illustrate other uses of the subject compounds, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) *J Exp Biol* 123:265-289; and Freund et al. (1985) *J Neurosci* 5:603-616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The subject method can be used to regulate the growth state in the culture, or where fetal tissue is used, especially neuronal stem cells, can be used to regulate the rate of differentiation of the stem cells.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of compounds employed in the present method to culture such stem cells can be to regulate differentiation of the uncommitted progenitor, or to regulate further restriction of the developmental fate of a committed progenitor cell towards becoming a terminally differentiated neuronal cell. For example, the present method can be used in vitro to regulate the differentiation of neural crest cells into glial cells, schwann cells, chromaffin cells, cholinergic sympathetic or parasympathetic neurons, as well as peptidergic and serotonergic neurons. The subject compounds can be used alone, or can be used in combination with other neurotrophic factors which act to more particularly enhance a particular differentiation fate of the neuronal progenitor cell.

In addition to the implantation of cells cultured in the presence of the subject compounds, yet another aspect of the present invention concerns the therapeutic application of a subject compound to regulate the growth state of neurons and other neuronal cells in both the central nervous system and the peripheral nervous system. The ability of ptc, hedgehog, and smoothened to regulate neuronal differentiation during development of the nervous system and also presumably in the adult state indicates that, in certain instances, the subject compounds can be expected to facilitate control of adult neurons with regard to maintenance, functional performance, and aging of normal cells; repair and regeneration processes in chemically or mechanically lesioned cells; and treatment of degeneration in certain pathological conditions. In light of this understanding, the present invention specifically contemplates applications of the subject method to the treatment protocol of (prevention and/or reduction of the severity of) neurological conditions deriving from: (i) acute, subacute, or chronic injury to the nervous system, including traumatic injury, chemical injury, vascular injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis, diabetic neuropathy, and the like, as well as spinocerebellar degenerations; and (iv) chronic immunological diseases of the nervous system or affecting the nervous system, including multiple sclerosis.

As appropriate, the subject method can also be used in generating nerve prostheses for the repair of central and peripheral nerve damage. In particular, where a crushed or severed axon is intubated by use of a prosthetic device, subject compounds can be added to the prosthetic device to regulate the rate of growth and regeneration of the dendritic processes. Exemplary nerve guidance channels are described in U.S. Pat. Nos. 5,092,871 and 4,955,892.

In another embodiment, the subject method can be used in the treatment of neoplastic or hyperplastic transformations such as may occur in the central nervous system. For instance, the subject compounds can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas.

In a preferred embodiment, the subject method can be used as part of a treatment regimen for malignant medulloblastoma and other primary CNS malignant neuroectodermal tumors.

In certain embodiments, the subject method is used as part of treatment program for medulloblastoma. Medulloblastoma, a primary brain tumor, is the most common brain tumor in children. A medulloblastoma is a primitive neuroectodermal tumor arising in the posterior fossa. They account for approximately 25% of all pediatric brain tumors (Miller). Histologically, they are small round cell tumors commonly arranged in true rosettes, but may display some differentiation to astrocytes, ependymal cells or neurons (Rorke; Kleihues). PNET's may arise in other areas of the brain including the pineal gland (pineoblastoma) and cerebrum. Patients with tumors arising in the supratentorial region generally fare worse than their PF counterparts.

Medulloblastoma/PNET's are known to recur anywhere in the CNS after resection, and can even metastasize to bone. Pretreatment evaluation should therefore include an examination of the spinal cord to exclude the possibility of "dropped metastases". Gadolinium-enhanced MRI has largely replaced myelography for this purpose, and CSF cytology is obtained postoperatively as a routine procedure.

In other embodiments, the subject method is used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes. In the CHOP series of 51 children reported with ependymomas, ¾ were histologically benign. Approximately ⅔ arose from the region of the 4th ventricle. One third presented in the supratentorial region. Age at presentation peaks between birth and 4 years, as demonstrated by SEER data as well as data from CHOP. The median age is about 5 years. Because so many children with this disease are babies, they often require multimodal therapy.

Yet another aspect of the present invention concerns the observation in the art that ptc, hedgehog, and/or smoothened are involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising one or more of the subject compounds can also be utilized for both cell culture and therapeutic methods involving generation and maintenance of non-neuronal tissue.

In one embodiment, the present invention makes use of the discovery that ptc, hedgehog, and smoothened are apparently involved in controlling the development of stem cells responsible for formation of the digestive tract, liver, lungs, and other organs which derive from the primitive gut. Shh serves as an inductive signal from the endoderm to the mesoderm, which is critical to gut morphogenesis. Therefore, for example, compounds of the instant method can be employed for regulating the development and maintenance of an artificial liver which can have multiple metabolic functions of a normal liver. In an exemplary embodiment, the subject method can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of subject compounds can be utilized in conjunction with transplantation of such artificial livers, as well as embryonic liver structures, to regulate uptake of intraperitoneal implantation, vascularization, and in vivo differentiation and maintenance of the engrafted liver tissue.

In yet another embodiment, the subject method can be employed therapeutically to regulate such organs after physical, chemical or pathological insult. For instance, therapeutic compositions comprising subject compounds can be utilized in liver repair subsequent to a partial hepatectomy.

The generation of the pancreas and small intestine from the embryonic gut depends on intercellular signalling between the endodermal and mesodermal cells of the gut. In particular, the differentiation of intestinal mesoderm into smooth muscle has been suggested to depend on signals from adjacent endodermal cells. One candidate mediator of endodermally derived signals in the embryonic hindgut is Sonic hedgehog. See, for example, Apelqvist et al. (1997) *Curr Biol* 7:801-4. The Shh gene is expressed throughout the embryonic gut endoderm with the exception of the pancreatic bud endoderm, which instead expresses high levels of the homeodomain protein Ipf1/Pdx1 (insulin promoter factor 1/pancreatic and duodenal homeobox 1), an essential regulator of early pancreatic development. Apelqvist et al., supra, have examined whether the differential expression of Shh in the embryonic gut tube controls the differentiation of the surrounding mesoderm into specialised mesoderm derivatives of the small intestine and pancreas. To test this, they used the promoter of the Ipf1/Pdx1 gene to selectively express Shh in the developing pancreatic epithelium. In Ipf1/Pdx1– Shh transgenic mice, the pancreatic mesoderm developed into smooth muscle and interstitial cells of Cajal, characteristic of the intestine, rather than into pancreatic mesenchyme and spleen. Also, pancreatic explants exposed to Shh underwent a similar program of intestinal differentiation. These results provide evidence that the differential expression of endodermally derived Shh controls the fate of adjacent mesoderm at different regions of the gut tube.

In the context of the present invention, it is contemplated therefore that the subject compounds can be used to control or regulate the proliferation and/or differentiation of pancreatic tissue both in vivo and in vitro.

There are a wide variety of pathological cell proliferative and differentiative conditions for which the inhibitors of the present invention may provide therapeutic benefits, with the general strategy being, for example, the correction of aberrant insulin expression, or modulation of differentiation. More generally, however, the present invention relates to a method of inducing and/or maintaining a differentiated state, enhancing survival and/or affecting proliferation of pancreatic cells, by contacting the cells with the subject inhibitors. For instance, it is contemplated by the invention that, in light of the apparent involvement of ptc, hedgehog, and smoothened in the formation of ordered spatial arrangements of pancreatic tissues, the subject method could be used as part of a technique to generate and/or maintain such tissue both in vitro and in vivo. For instance, modulation of the function of hedgehog can be employed in both cell culture and therapeutic methods involving generation and maintenance β-cells and possibly also for non-pancreatic tissue, such as in controlling the development and maintenance of tissue from the digestive tract, spleen, lungs, urogenital organs (e.g., bladder), and other organs which derive from the primitive gut.

In an exemplary embodiment, the present method can be used in the treatment of hyperplastic and neoplastic disorders affecting pancreatic tissue, particularly those characterized by aberrant proliferation of pancreatic cells. For instance, pancreatic cancers are marked by abnormal proliferation of pancreatic cells which can result in alterations of insulin secretory capacity of the pancreas. For instance, certain pancreatic hyperplasias, such as pancreatic carcinomas, can result in hypoinsulinemia due to dysfunction of β-cells or decreased islet cell mass. To the extent that aberrant ptc, hedgehog, and smoothened signaling may be indicated in disease progression, the subject regulators can be used to enhance regeneration of the tissue after anti-tumor therapy.

Moreover, manipulation of hedgehog signaling properties at different points may be useful as part of a strategy for reshaping/repairing pancreatic tissue both in vivo and in vitro. In one embodiment, the present invention makes use of the apparent involvement of ptc, hedgehog, and smoothened in regulating the development of pancreatic tissue. In general, the subject method can be employed therapeutically to regulate the pancreas after physical, chemical or pathological insult. In yet another embodiment, the subject method can be applied to cell culture techniques, and in particular, may be employed to enhance the initial generation of prosthetic pancreatic tissue devices. Manipulation of proliferation and differentiation of pancreatic tissue, for example, by altering hedgehog activity, can provide a means for more carefully controlling the characteristics of a cultured tissue. In an exemplary embodiment, the subject method can be used to augment production of prosthetic devices which require β-islet cells, such as may be used in the encapsulation devices described in, for example, the Aebischer et al. U.S. Pat. No. 4,892,538, the Aebischer et al. U.S. Pat. No. 5,106,627, the Lim U.S. Pat. No. 4,391,909, and the Sefton U.S. Pat. No. 4,353,888. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearance of embryonal traits in mature β-cells can be observed. By utilizing the subject compounds, the differentiation path or proliferative index of the cells can be regulated.

Furthermore, manipulation of the differentiative state of pancreatic tissue can be utilized in conjunction with transplantation of artificial pancreas so as to promote implantation, vascularization, and in vivo differentiation and maintenance of the engrafted tissue. For instance, manipulation of hedgehog function to affect tissue differentiation can be utilized as a means of maintaining graft viability.

Bellusci et al. (1997) *Development* 124:53 report that Sonic hedgehog regulates lung mesenchymal cell proliferation in vivo. Accordingly, the present method can be used to regulate regeneration of lung tissue, e.g., in the treatment of emphysema.

Fujita et al. (1997) *Biochem Biophys Res Commun* 238: 658 reported that Sonic hedgehog is expressed in human lung squamous carcinoma and adenocarcinoma cells. The expression of Sonic hedgehog was also detected in the human lung squamous carcinoma tissues, but not in the normal lung tissue of the same patient. They also observed that Sonic hedgehog stimulates the incorporation of BrdU into the carcinoma cells and stimulates their cell growth, while anti-Shh-N inhibited their cell growth. These results suggest that a ptc, hedgehog, and/or smoothened is involved in the cell growth of such transformed lung tissue and therefore indicates that the subject method can be used as part of a treatment of lung carcinoma and adenocarcinomas, and other proliferative disorders involving the lung epithelia.

Many other tumors may, based on evidence such as involvement of the hedgehog pathway in these tumors, or detected expression of hedgehog or its receptor in these tissues during development, be affected by treatment with the subject compounds. Such tumors include, but are by no means limited to, tumors related to Gorlin's syndrome (e.g., basal cell carcinoma, medulloblastoma, meningioma, etc.), tumors evidenced in pct knock-out mice (e.g., hemangioma, rhabdomyosarcoma, etc.), tumors resulting from gli-1 amplification (e.g., glioblastoma, sarcoma, etc.), tumors connected with TRC8, a ptc homolog (e.g., renal carcinoma, thyroid carcinoma, etc.), Ext-1-related tumors (e.g., bone cancer, etc.), Shh-induced tumors (e.g., lung cancer, chondrosarcomas, etc.), and other tumors (e.g., breast cancer, urogenital cancer (e.g., kidney, bladder, ureter, prostate, etc.), adrenal cancer, gastrointestinal cancer (e.g., stomach, intestine, etc.), etc.).

In still another embodiment of the present invention, compositions comprising one or more of the subject compounds can be used in the in vitro generation of skeletal tissue, such as from skeletogenic stem cells, as well as the in vivo treatment of skeletal tissue deficiencies. The present invention particularly contemplates the use of subject compounds to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

For instance, the method of the present invention can be used as part of a regimen for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a laxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a subject compound to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent.

In an illustrative embodiment, the subject method can be used as part of a therapeutic intervention in the treatment of cartilage of a diarthroidal joint, such as a knee, an ankle, an elbow, a hip, a wrist, a knuckle of either a finger or toe, or a tempomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. The subject regulators may be administered as an injection into the joint with, for instance, an arthroscopic needle. In some instances, the injected agent can be in the form of a hydrogel or other slow release vehicle in order to permit a more extended and regular contact of the agent with the treated tissue.

The present invention further contemplates the use of the subject method in the field of cartilage transplantation and prosthetic device therapies. However, problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By regulating the rate of chondrogenesis, the subject method can be used to particularly address this problem, by helping to adaptively control the implanted cells in the new environment and effectively resemble hypertrophic chondrocytes of an earlier developmental stage of the tissue.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed Mater Res* 25:329; Freed et al. (1993) *J Biomed Mater Res* 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a subject compound during certain stages of the culturing process in order to manage the rate of differentiation of chondrocytes and the formation of hypertrophic chrondrocytes in the culture.

In another embodiment, the implanted device is treated with a subject compound in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The ability to regulate the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis.

In still further embodiments, the subject method can be employed as part of a regimen for the generation of bone (osteogenesis) at a site in the animal where such skeletal tissue is deficient. Indian hedgehog is particularly associated with the hypertrophic chondrocytes that are ultimately replaced by osteoblasts. For instance, administration of a compound of the present invention can be employed as part of a method for regulating the rate of bone loss in a subject. For example, preparations comprising subject compounds can be employed, for example, to control endochondral ossification in the formation of a "model" for ossification.

In yet another embodiment of the present invention, a subject compound can be used to regulate spermatogenesis.

The hedgehog proteins, particularly Dhh, have been shown to be involved in the differentiation and/or proliferation and maintenance of testicular germ cells. Dhh expression is initiated in Sertoli cell precursors shortly after the activation of Sry (testicular determining gene) and persists in the testis into the adult. Males are viable but infertile, owing to a complete absence of mature sperm. Examination of the developing testis in different genetic backgrounds suggests that Dhh regulates both early and late stages of spermatogenesis. Bitgood et al. (1996) *Curr Biol* 6:298. In a preferred embodiment, the subject compound can be used as a contraceptive. In similar fashion, compounds of the subject method are potentially useful for modulating normal ovarian function.

The subject method also has wide applicability to the treatment or prophylaxis of disorders afflicting epithelial tissue, as well as in cosmetic uses. In general, the method can be characterized as including a step of administering to an animal an amount of a subject compound effective to alter the growth state of a treated epithelial tissue. The mode of administration and dosage regimens will vary depending on the epithelial tissue(s) which is to be treated. For example, topical formulations will be preferred where the treated tissue is epidermal tissue, such as dermal or mucosal tissues.

A method which "promotes the healing of a wound" results in the wound healing more quickly as a result of the treatment than a similar wound heals in the absence of the treatment. "Promotion of wound healing" can also mean that the method regulates the proliferation and/or growth of, inter alia, keratinocytes, or that the wound heals with less scarring, less wound contraction, less collagen deposition and more superficial surface area. In certain instances, "promotion of wound healing" can also mean that certain methods of wound healing have improved success rates, (e.g., the take rates of skin grafts) when used together with the method of the present invention.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the subject method, the rate of proliferation of epithelial cells in and proximal to the wound can be controlled in order to accelerate closure of the wound and/or minimize the formation of scar tissue.

The present treatment can also be effective as part of a therapeutic regimen for treating oral and paraoral ulcers, e.g., resulting from radiation and/or chemotherapy. Such ulcers commonly develop within days after chemotherapy or radiation therapy. These ulcers usually begin as small, painful irregularly shaped lesions usually covered by a delicate gray necrotic membrane and surrounded by inflammatory tissue. In many instances, lack of treatment results in proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, dispose the body to potential secondary infection. Routine ingestion of food and water becomes a very painful event and, if the ulcers proliferate throughout the alimentary canal, diarrhea usually is evident with all its complicating factors. According to the present invention, a treatment for such ulcers which includes application of a subject compound can reduce the abnormal proliferation and differentiation of the affected epithelium, helping to reduce the severity of subsequent inflammatory events.

The subject method and compositions can also be used to treat wounds resulting from dermatological diseases, such as lesions resulting from autoimmune disorders such as psoriasis. Atopic dermitits refers to skin trauma resulting from allergies associated with an immune response caused by allergens such as pollens, foods, dander, insect venoms and plant toxins.

In other embodiments, antiproliferative preparations of subject compounds can be used to inhibit lens epithelial cell proliferation to prevent post-operative complications of extracapsular cataract extraction. Cataract is an intractable eye disease and various studies on a treatment of cataract have been made. But at present, the treatment of cataract is attained by surgical operations. Cataract surgery has been applied for a long time and various operative methods have been examined. Extracapsular lens extraction has become the method of choice for removing cataracts. The major medical advantages of this technique over intracapsular extraction are lower incidence of aphakic cystoid macular edema and retinal detachment. Extracapsular extraction is also required for implantation of posterior chamber type intraocular lenses which are now considered to be the lenses of choice in most cases.

However, a disadvantage of extracapsular cataract extraction is the high incidence of posterior lens capsule opacification, often called after-cataract, which can occur in up to 50% of cases within three years after surgery. After-cataract is caused by proliferation of equatorial and anterior capsule lens epithelial cells which remain after extracapsular lens extraction. These cells proliferate to cause Sommerling rings, and along with fibroblasts which also deposit and occur on the posterior capsule, cause opacification of the posterior capsule, which interferes with vision. Prevention of after-cataract would be preferable to treatment. To inhibit secondary cataract formation, the subject method provides a means for inhibiting proliferation of the remaining lens epithelial cells. For example, such cells can be induced to remain quiescent by instilling a solution containing a preparation of a subject compound into the anterior chamber of the eye after lens removal. Furthermore, the solution can be osmotically balanced to provide minimal effective dosage when instilled into the anterior chamber of the eye, thereby inhibiting subcapsular epithelial growth with some specificity.

The subject method can also be used in the treatment of corneopathies marked by corneal epithelial cell proliferation, as for example in ocular epithelial disorders such as epithelial downgrowth or squamous cell carcinomas of the ocular surface.

Levine et al. (1997) *J Neurosci* 17:6277 show that hedgehog proteins can regulate mitogenesis and photoreceptor differentiation in the vertebrate retina, and Ihh is a candidate factor from the pigmented epithelium to promote retinal progenitor proliferation and photoreceptor differentiation. Likewise, Jensen et al. (1997) *Development* 124:363 demonstrated that treatment of cultures of perinatal mouse retinal cells with the amino-terminal fragment of Sonic hedgehog results in an increase in the proportion of cells that incorporate bromodeoxuridine, in total cell numbers, and in rod photoreceptors, amacrine cells and Muller glial cells, suggesting that Sonic hedgehog promotes the proliferation of retinal precursor cells. Thus, the subject method can be used in the treatment of proliferative diseases of retinal cells and regulate photoreceptor differentiation.

Yet another aspect of the present invention relates to the use of the subject method to control hair growth. Hair is basically composed of keratin, a tough and insoluble protein; its chief strength lies in its disulphide bond of cystine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth can be carried out by potentiating or inhibiting, respectively, the proliferation of these stem cells.

In certain embodiments, the subject method can be employed as a way of reducing the growth of human hair as opposed to its conventional removal by cutting, shaving, or depilation. For instance, the present method can be used in the treatment of trichosis characterized by abnormally rapid or dense growth of hair, e.g. hypertrichosis. In an exemplary embodiment, subject compounds can be used to manage hirsutism, a disorder marked by abnormal hairiness. The subject method can also provide a process for extending the duration of depilation.

Moreover, because a subject compound will often be cytostatic to epithelial cells, rather than cytotoxic, such agents can be used to protect hair follicle cells from cytotoxic agents which require progression into S-phase of the cell-cycle for efficacy, e.g. radiation-induced death. Treatment by the subject method can provide protection by causing the hair follicle cells to become quiescent, e.g., by inhibiting the cells from entering S phase, and thereby preventing the follicle cells from undergoing mitotic catastrophe or programmed cell death. For instance, subject compounds can be used for patients undergoing chemo- or radiation-therapies which ordinarily result in hair loss. By inhibiting cell-cycle progression during such therapies, the subject treatment can protect hair follicle cells from death which might otherwise result from activation of cell death programs. After the therapy has concluded, the instant method can also be removed with concomitant relief of the inhibition of follicle cell proliferation.

The subject method can also be used in the treatment of folliculitis, such as folliculitis decalvans, folliculitis ulery-thematosa reticulata or keloid folliculitis. For example, a cosmetic preparation of a subject compound can be applied topically in the treatment of pseudofolliculitis, a chronic disorder occurring most often in the submandibular region of the neck and associated with shaving, the characteristic lesions of which are erythematous papules and pustules containing buried hairs.

In another aspect of the invention, the subject method can be used to induce differentiation and/or inhibit proliferation of epithelially derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For instance, the pharmaceutical preparations of the invention are intended for the treatment of hyperplastic epidermal conditions, such as keratosis, as well as for the treatment of neoplastic epidermal conditions such as those characterized by a high proliferation rate for various skin cancers, as for example basal cell carcinoma or squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin, the keratinocytes are known to proliferate much more rapidly than normal and to differentiate less completely.

In one embodiment, the preparations of the present invention are suitable for the treatment of dermatological ailments linked to keratinization disorders causing abnormal proliferation of skin cells, which disorders may be marked by either inflammatory or non-inflammatory components. To illustrate, therapeutic preparations of a subject compound, e.g., which promotes quiescense or differentiation, can be used to treat varying forms of psoriasis, be they cutaneous, mucosal or ungual. Psoriasis, as described above, is typically characterized by epidermal keratinocytes which display marked proliferative activation and differentiation along a "regenerative" pathway. Treatment with an antiproliferative embodiment of the subject method can be used to reverse the pathological epidermal activation and can provide a basis for sustained remission of the disease.

A variety of other keratotic lesions are also candidates for treatment with the subject method. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of a subject compound composition in amounts sufficient to inhibit hyperproliferation of epidermal/epidermoid cells of the lesion.

Acne represents yet another dermatologic ailment which may be treated by the subject method. Acne vulgaris, for instance, is a multifactorial disease most commonly occurring in teenagers and young adults, and is characterized by the appearance of inflammatory and noninflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by *Propinobacterium acnes* and *Staphylococcus epidermidis* bacteria and *Pitrosporum ovale*, a yeast. Treatment with an antiproliferative subject compound, particularly topical preparations, may be useful for preventing the transitional features of the ducts, e.g. hypercornification, which lead to lesion formation. The subject treatment may further include, for example, antibiotics, retinoids and antiandrogens.

The present invention also provides a method for treating various forms of dermatitis. Dermatitis is a descriptive term referring to poorly demarcated lesions which are either pruritic, erythematous, scaly, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow crusted patches on various areas, especially the scalp, with exfoliation of an excessive amount of dry scales. The subject method can also be used in the treatment of stasis dermatitis, an often chronic, usually eczematous dermatitis. Actinic dermatitis is dermatitis that due to exposure to actinic radiation such as that from the sun, ultraviolet waves or x- or gamma-radiation. According to the present invention, the subject method can be used in the treatment and/or prevention of certain symptoms of dermatitis caused by unwanted proliferation of epithelial cells. Such therapies for these various forms of dermatitis can also include topical and systemic corticosteroids, antipuritics, and antibiotics.

Ailments which may be treated by the subject method are disorders specific to non-humans, such as mange.

In still another embodiment, the subject method can be used in the treatment of human cancers, particularly basal cell carcinomas and other tumors of epithelial tissues such as the skin. For example, subject compounds can be employed, in the subject method, as part of a treatment for basal cell nevus syndrome (BCNS), and other other human carcinomas, adenocarcinomas, sarcomas and the like.

In a preferred embodiment, the subject method is used as part of a treatment of prophylaxis regimen for treating (or preventing) basal cell carcinoma. The deregulation of the hedgehog signaling pathway may be a general feature of basal cell carcinomas caused by ptc mutations. Consistent overexpression of human ptc mRNA has been described in tumors of familial and sporadic BCCs, determined by in situ hybridization. Mutations that inactivate ptc may be expected to result in overexpression of mutant Ptc, because ptc displays negative autoregulation. Prior research demonstrates that overexpression of hedgehog proteins can also lead to tumorigenesis. That sonic hedgehog (Shh) has a role in tumorigenesis in the mouse has been suggested by research in which transgenic mice overexpressing Shh in the skin developed features of BCNS, including multiple BCC-like epidermal proliferations over the entire skin surface, after only a few days of skin development. A mutation in the Shh human gene from a BCC was also described; it was suggested that Shh or other Hh genes in humans could act as dominant oncogenes in humans. Sporadic ptc mutations have also been observed in BCCs from otherwise normal individuals, some of which are UV-signature mutations. In one recent study of sporadic BCCs, five UV-signature type mutations, either CT or CCTT changes, were found out of fifteen tumors determined to contain ptc mutations. Another recent analysis of sporadic ptc mutations in BCCs and neuroectodermal tumors revealed one CT change in one of three ptc mutations found in the BCCs. See, for example, Goodrich et al. (1997) *Science* 277:1109-13; Xie et al. (1997) *Cancer Res* 57:2369-72; Oro et al. (1997) *Science* 276:817-21; Xie et al. (1997) *Genes Chromosomes Cancer* 18:305-9; Stone et al. (1996) *Nature* 384:129-34; and Johnson et al. (1996) *Science* 272:1668-71.

The subject method can also be used to treat patients with BCNS, e.g., to prevent BCC or other effects of the disease which may be the result of ptc loss-of-function, hedgehog gain-of-function, or smoothened gain-of-function. Basal cell nevus syndrome is a rare autosomal dominant disorder characterized by multiple BCCs that appear at a young age. BCNS patients are very susceptible to the development of these tumors; in the second decade of life, large numbers appear, mainly on sun-exposed areas of the skin. This disease also causes a number of developmental abnormalities, including rib, head and face alterations, and sometimes polydactyl), syndactyl), and spina bifida. They also develop a number of tumor types in addition to BCCs: fibromas of the ovaries and heart, cysts of the skin and jaws, and in the central nervous system, medulloblastomas and meningiomas. The subject method can be used to prevent or treat such tumor types in BCNS and non-BCNS patients. Studies of BCNS patients show that they have both genomic and sporadic mutations in the ptc gene, suggesting that these mutations are the ultimate cause of this disease.

In another aspect, the present invention provides pharmaceutical preparations and methods for controlling the formation of megakaryocyte-derived cells and/or controlling the functional performance of megakaryocyte-derived cells. For instance, certain of the compositions disclosed herein may be applied to the treatment or prevention of a variety hyperplastic or neoplastic conditions affecting platelets.

In another aspect, the present invention provides pharmaceutical preparations comprising the subject compounds. The compounds for use in the subject method may be conveniently formulated for administration with a biologically acceptable and/or sterile medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the subject compounds, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations".

Pharmaceutical formulations of the present invention can also include veterinary compositions, e.g., pharmaceutical preparations of the subject compounds suitable for veterinary uses, e.g., for the treatment of live stock or domestic animals, e.g., dogs.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a subject compound at a particular target site.

The preparations of the present invention may be given orally, parenterally, topically, or rectally. They are of course given by forms suitable for each administration route. For example, they are administered in tablets or capsule form, by injection, inhalation, eye lotion, ointment, suppository, controlled release patch, etc. administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable and/or sterile carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

V. Pharmaceutical Compositions

While it is possible for a compound of the present invention to be administered alone, it is preferable to administer the compound as a pharmaceutical formulation (composition). The subject compounds according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water. In certain embodiments, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect, e.g., by overcoming a ptc loss-of-function, hedgehog gain-of-function, or smoothened gain-of-function, in at least a sub-population of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject regulators from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

It is known that sterols, such as cholesterol, will form complexes with cyclodextrins. Thus, in preferred embodiments, where the inhibitor is a steroidal alkaloid, it may be formulated with cyclodextrins, such as α-, β- and γ-cyclodextrin, dimethyl-β cyclodextrin and 2-hydroxypropyl-β-cyclodextrin.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the subject compounds in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" 0 and B books, Corvallis, Ore., U.S.A., 1977).

VI. Synthetic Schemes and Identification of Active Regulators

The subject compounds, and derivatives thereof, can be prepared readily by employing known synthetic methodology. As is well known in the art, these coupling reactions are carried out under relatively mild conditions and tolerate a wide range of "spectator" functionality. Additional compounds may be synthesized and tested in a combinatorial fashion, to facilitate the identification of additional compounds which may be employed in the subject method.

a. Combinatorial Libraries

The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g. a variegated library of compounds represented above, can be screened rapidly in high throughput assays in order to identify potential hedgehog regulator lead compounds, as well as to refine the specificity, toxicity, and/or cytotoxic-kinetic profile of a lead compound. For instance, ptc, hedgehog, or smoothened bioactivity assays, such as may be developed using cells with either a ptc loss-of-function, hedgehog gain-of-function, or smoothened gain-of-function, can be used to screen a library of the subject compounds for those having agonist activity toward ptc or antagonist activity towards hedgehog or smoothened. Alternatively, bioactivity assays using cells with either a ptc gain-of-function, hedgehog loss-of-function, or smoothened loss-of-function, can be used to screen a library of the subject compounds for those having antagonist activity toward ptc or agonist activity towards hedgehog or smoothened.

Simply for illustration, a combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate physical properties can be done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject compounds. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; the ArQule U.S. Pat. Nos. 5,736,412 and 5,712,171; Chen et al.

(1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the subject compounds can be synthesized and screened for particular activity or property.

In an exemplary embodiment, a library of candidate compound diversomers can be synthesized utilizing a scheme adapted to the techniques described in the Still et al. PCT publication WO 94/08051, e.g., being linked to a polymer bead by a hydrolyzable or photolyzable group, optionally located at one of the positions of the candidate regulators or a substituent of a synthetic intermediate. According to the Still et al. technique, the library is synthesized on a set of beads, each bead including a set of tags identifying the particular diversomer on that bead. The bead library can then be "plated" with, for example, ptc loss-of-function, hedgehog gain-of-function, or smoothened gain-of-function cells for which a smoothened antagonist is sought. The diversomers can be released from the bead, e.g. by hydrolysis.

Many variations on the above and related pathways permit the synthesis of widely diverse libraries of compounds which may be tested as regulators of hedgehog function.

b. Screening Assays

There are a variety of assays available for determining the ability of a compound such as a hedgehog regulator to regulate ptc, smoothened, or hedgehog function, many of which can be disposed in high-throughput formats. In many drug screening programs which test libraries of compounds and natural extracts, high throughput assays are desirable in order to maximize the number of compounds surveyed in a given period of time. Thus, libraries of synthetic and natural products can be sampled for other compounds which are hedgehog regulators.

In addition to cell-free assays, test compounds can also be tested in cell-based assays. In one embodiment, cells which have a ptc loss-of-function, hedgehog gain-of-function, or smoothened gain-of-function phenotype can be contacted with a test agent of interest, with the assay scoring for, e.g., inhibition of proliferation of the cell in the presence of the test agent.

A number of gene products have been implicated in patched-mediated signal transduction, including patched, transcription factors of the cubitus interruptus (ci) family, the serine/threonine kinase fused (fu) and the gene products of costal-2, smoothened and suppressor of fused.

The induction of cells by hedgehog proteins sets in motion a cascade involving the activation and inhibition of downstream effectors, the ultimate consequence of which is, in some instances, a detectable change in the transcription or translation of a gene. Potential transcriptional targets of hedgehog-mediated signaling are the patched gene (Hidalgo and Ingham, 1990 *Development* 110, 291-301; Marigo et al., 1996) and the vertebrate homologs of the *drosophila* cubitus interruptus gene, the GLI genes (Hui et al. (1994) *Dev Biol* 162:402-413). Patched gene expression has been shown to be induced in cells of the limb bud and the neural plate that are responsive to Shh. (Marigo et al. (1996) *PNAS* 93:9346-51; Marigo et al. (1996) *Development* 122:1225-1233). The Gli genes encode putative transcription factors having zinc finger DNA binding domains (Orenic et al. (1990) *Genes & Dev* 4:1053-1067; Kinzler et al. (1990) *Mol Cell Biol* 10:634-642). Transcription of the Gli gene has been reported to be upregulated in response to hedgehog in limb buds, while transcription of the Gli3 gene is downregulated in response to hedgehog induction (Marigo et al. (1996) *Development* 122:1225-1233). By selecting transcriptional regulatory sequences from such target genes, e.g., from patched or Gli genes, that are responsible for the up- or down-regulation of these genes in response to hedgehog signalling, and operatively linking such promoters to a reporter gene, one can derive a transcription based assay which is sensitive to the ability of a specific test compound to modify hedgehog-mediated signalling pathways. Expression of the reporter gene, thus, provides a valuable screening tool for the development of compounds that act as regulators of hedgehog.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on ptc loss-of-function, hedgehog gain-of-function, smoothened gain-of-function, or stimulation by Shh itself. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic biological activity. The amount of expression from the reporter gene is then compared to the amount of expression in either the same cell in the absence of the test compound or it may be compared with the amount of transcription in a substantially identical cell that lacks the target receptor protein. Any statistically or otherwise significant decrease in the amount of transcription indicates that the test compound has in some manner agonized the normal ptc signal (or antagonized the gain-of-function hedgehog or smoothened signal), e.g., the test compound is a potential smoothened antagonist.

EXEMPLIFICATION

The invention now being generally described, it will be more readily understood by reference to the following examples which are included merely for purposes of illustration of certain aspects and embodiments of the present invention, and are not intended to limit the invention.

Example 1

Steroidal Compounds

Hedgehog signaling pathways are required for normal embryonic development yet also are associated with carcinogenesis (L. V. Goodrich and M. P. Scott, *Neuron* 21, 1243 (1998)). Loss of Sonic hedgehog signaling (Shh), for example, can result in cyclopia and other developmental defects of the face, forebrain, and other organs and structures (C. Chiang et al., *Nature* 383, 407 (1996)), whereas inappropriate activation of the pathway is associated with basal cell carcinoma, medulloblastoma, and other neoplastic disorders (H. Hahn et al., *Cell* 85, 841 (1996); R. L. Johnson et al., *Science* 272, 1668 (1996); M. Gailani et al., *Nat Genet.* 14, 78 (1996); T. Pietsch et al., *Cancer Res* 57, 2085 (1997); J. Reifenberger et al., *Cancer Res.* 58, 1798 (1998); C. Raffel et al., *Cancer Res* 57, 842 (1997); J. Xie et al., *Nature* 391, 90 (1998)). Pharmacological manipulation of this pathway thus might help elucidate the mechanisms of signal transduction and also provide a practical means to prevent or remedy somatic and congenital abnormalities. Cyclopamine, a plant steroidal alkaloid, has long been known to induce cyclopia and other manifestations of severe HPE in vertebrate embryos (R. F. Keeler and W. Binns, *Teratology* 1, 5 (1968)) and more recently was shown to act by inhibiting the cellular response to the Shh signal (M. K. Cooper, J. A. Porter, K. E. Young, P. A. Beachy, *Science* 280, 1603 (1998); J. P. Incardona, W. Gaffield, R. P. Kapur, H. Roelink, *Development* 125, 3553 (1998)). To evaluate the therapeutic potential of cyclopamine, we investigated the mechanism by which it acts.

Figure 2A:
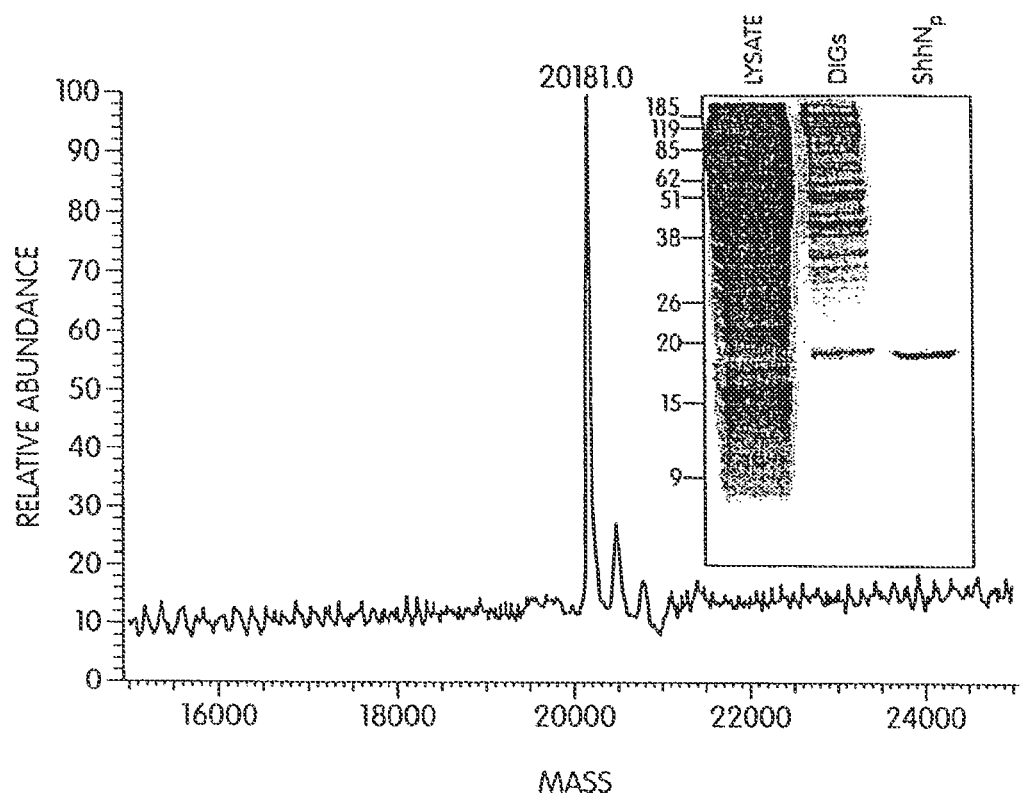
FIG. 2 relates to a sensitive assay for Shh signaling in NIH-3T3 cells. (A) Purification of cholesterol- and palmitate-modified mouse Sonic hedgehog signaling domain ShhN$_p$. Detergent-insoluble proteolipid complexes were isolated from 293 cells expressing full-length Shh (M. K. Cooper, J. A. Porter, K. E. Young, P. A. Beachy, Science 280, 1603 (1998)), and ShhN$_p$ was purified to apparent homogeneity by immunoaffinity chromatography. Although recombinant ShhN lacking cholesterol and palmitate modifications is fully active in neural plate explant culture assays, this form of ShhN was poorly active in the NIH-3T3 cells. We therefore used the detergent insolubility of cholesterol-modified ShhN and affinity chromatography to purify the processed ShhN protein (ShhN$_p$) from a human 293 cell line engineered to express the full length mouse Shh construct. Detergent-insoluble complexes (DIGs) were isolated as described by Brown and Rose (1992), with the following modifications. Cells from a 150 mm dish were lysed and collected in 2 mL of lysis solution (10 mM NaHPO$_4$, pH 6.5, 150 mM NaCl, 0.5 mM PMSF, 1% Triton X-100, 2 µg/ml Pepstatin A, 10 µg/ml leupeptin, 5 µg/ml aprotinin, 2 µg/ml E64) at 4° C. Eight sucrose density steps (35.625-5%, 4.375%/step; made in above solution, without detergent) were layered onto the 40% sucrose lysate and centrifugation proceeded for 2-12 hr. Low-density, flocculent material was collected (from original position of 18.125% step), diluted 5-fold in 10 mM NaHPO$_4$, pH 6.5, 150 mM NaCl and harvested by centrifugation at 20,000×g for 15 min (all at 4° C.). Complexes were solubilized at ambient temperature in 1% n-octyl-α-D-glucopyranoside, 50 mM HEPES, pH 7.5, 150 mM NaCl and the single ShhN$_p$ immunoaffinity purification step proceeded essentially as described in Pepinsky et al. (1998), except the anti-Shh-N monoclonal antibody 5E1 was coupled to Affi-Gel 10 (Bio-Rad) at 6.6 mg/ml gel. The mass of the purified species as determined by mass spectrometry corresponds to that of the ShhN polypeptide bearing covalent palmitoyl and cholesteryl adducts: murine ShhN polypeptide, 19,574.05 Da; esterified cholesterol, 368.65; palmitoyl mass (in ester or amide linkage), 238.42; sum, 20,181.1. The inset shows samples from lysate, detergent-insoluble glycolipid complexes (DIGs; 8 lysate sample equivalents), and purified ShhN$_p$ (0.75 µg) as separated in SDS-PAGE (14%) and stained with Coomassie blue. Mass standards migrated as indicated. (B) NIH-3T3 cells respond to ShhN$_p$. NIH-3T3 cells cotransfected with Gli-luc reporter and TK promoter-driven Renilla luciferase control were treated with the indicated concentrations of ShhN$_p$ for 2 days. Confluent cultures of NIH-3T3 cells were plated at 1:6 dilution to 24 or 96-well plates. On the following day, the cells were transfected with renilla luciferase (pRL-TK or pRL-SV40; Clontech) or β-galactosidase transfection control (10% w/w DNA), Gli-Luc reporter (40%) and the constructs indicated (50%) using Fugene 6 (Roche) transfection reagent (250 ng (24 well plate) or 100 ng (96 well plate) DNA/well, 3:1 ratio (v/w) of reagent to DNA). After the cells had reached saturation density (1-2 d), they were changed to low serum medium (0.5% bovine calf serum), and treated with the reagents indicated for 1-2 d. Firefly and Renilla luciferase and β-galactosidase activities were assayed from the cell lysates by luminometry using dual luciferase (Promega) and Galacto-Light (Tropix) kits, respectively. Luciferase activities are normalized relative to control; a representative experiment is shown. Note that in this and all subsequent reporter assays, TK-Renilla luciferase activity is used as a control for normalization. (C) Shh pathway activation is sensitive to cyclopamine in NIH-3T3 cells. NIH-3T3 cells transfected as above (in triplicate) were treated with ShhN$_p$ (4 nM) and/or cyclopamine (5 µM) for 2 d as indicated. Normalized luciferase activities are given as fold induction relative to control. Error bars indicate one standard deviation. (D) Low cell density inhibits Shh pathway activity downstream of Smo. Cultures of Shh-LIGHT (open boxes) or SmoA1-LIGHT (filled diamonds) cells were plated to 96-well plates in a series of twofold dilutions. The NIH-3T3 cell clone Shh-LIGHT and Shh-LIGHT2 stably incorporating the Gli-luc reporter and TK-renilla vectors were established by cotransfection with a vector encoding G418 resistance (pSV-Neo), followed by selection with G418 and cell cloning. Subsequently, a clonal subline of Shh-LIGHT expressing activated Smo (SmoA1-LIGHT) was established using an expression vector that allows hygromycin selection (pcDNA3.1+ hygro; Invitrogen). The expression of SmoA1 in the cell line was verified by immunoblotting. The Shh-LIGHT cells were treated with 4 nM ShhN$_p$, and Gli-luciferase reporter activity was assayed after 24 h. Fold induction of the reporter (% of maximum is relative to equally dense Shh-LIGHT control culture) and cell densities (% of maximum Renilla luciferase activity) were measured at the end of the experiment. Error bars indicate one standard deviation (quadruplicate wells).
Figure 2B:
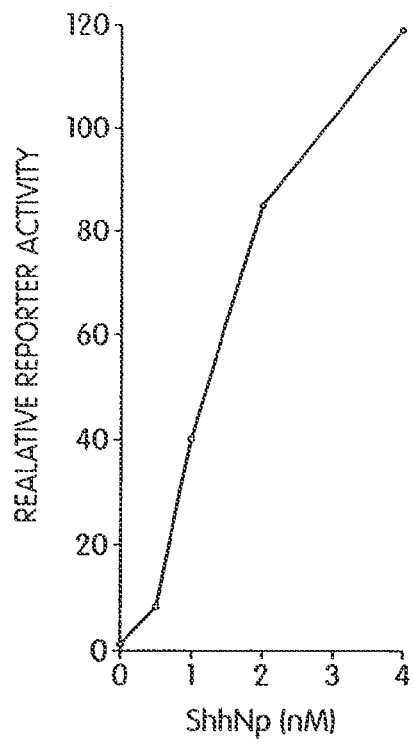
Figure 2C:
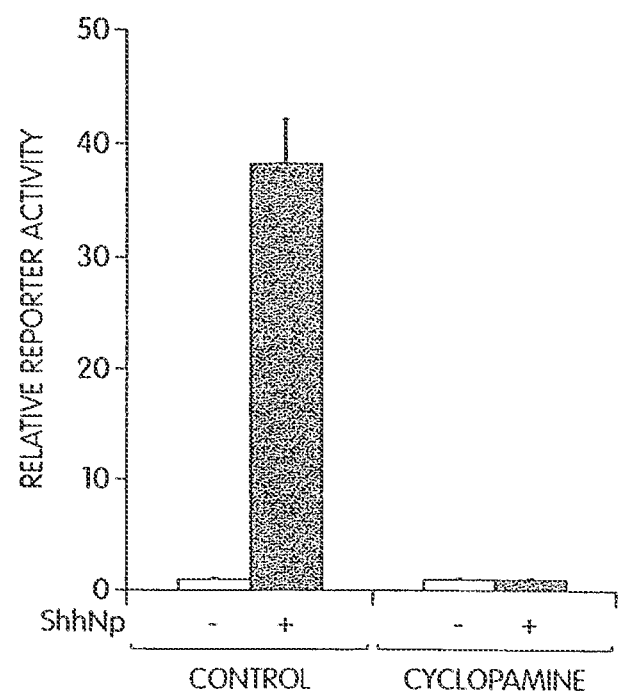

Cellular responses to the Hh signal are controlled by two multi-pass transmembrane proteins, Smo and Ptc1, predicted to have seven and twelve transmembrane spans, respectively. Smo is related to the Frizzled family of Wnt receptors and more distantly to the secretin family of G protein-coupled receptors (M. R. Barnes, D. M. Duckworth, L. J. Beeley, *Trends Pharmacol Sci* 19, 399 (1998)). Genetic and biochemical evidence suggests that Ptc suppresses the activity of Smo, and that Hh binding to Ptc relieves this suppression, allowing activation of downstream targets through the Ci/GLI family of transcriptional effectors (P. Aza-Blanc, F.-A. Remírez-Weber, M.-P. Laget, C. Schwartz, T. B. Kornberg, *Cell* 89, 1043 (1997); N. Methot and K. Basler, *Cell* 96, 819 (1999); C. H. Chen et al., *Cell* 98, 305 (1999); B. Wang, J. Fallon, P. Beachy, *Cell* 100, 423 (2000)). To establish a cultured cell based assay that is sensitive to cyclopamine (a previously established Hedgehog signaling assay in *Drosophila* c1-8 cells (Chen et al., 1999) is resistant to cyclopamine (not shown)), we screened several vertebrate cell lines for a transcriptional response to fully modified ShhN$_p$ (FIG. 2A) using a luciferase reporter driven by a promoter comprising eight synthetic Gli binding sites fused to the lens crystallin minimal promoter (H. Sasaki, C.-C. Hui, M. Nakafuku, H. Kondoh, *Development* 124, 1313 (1997)). Among several fibroblast cell lines that respond to ShhN$_p$, NIH-3T3 mouse embryonic fibroblasts, which respond with a 20-150 fold induction of luciferase activity (FIG. 2B), were selected for further studies. Importantly, when the cells were treated with cyclopamine, this induction by ShhN$_p$ was completely abolished (FIG. 2C).

Similar to the Hh signaling assay in *Drosophila* c1-8 cells, the response to induction by ShhN$_p$ required functional Gli binding sites in the reporter (not shown), and the response was augmented by overexpression of Smo and suppressed by overexpression of Ptc or of activated PKA (Table 1). Pharmacological activation of endogenous PKA by forskolin also prevented induction of reporter expression (Table 1). Using this assay, we confirmed the results of Xie et al. that the tumor mutation W539L (SmoA1) constitutively activates Smo, and found that another mutation from tumor tissue, S537N (SmoA2) also activates Smo. Expression of either of the activating mutants induced reporter expression to a level comparable to that observed in ShhN$_p$-treated cells. To further examine the validity of this signaling assay we transfected cells with constructs encoding known pathway components or treated cells with known inhibitors of the pathway and analyzed the effects of these treatments, alone and in combination, on reporter activation (Table 1). The major findings of *Drosophila* and mouse genetic analyses were confirmed, indicating that NIH-3T3 cells provide a faithful and physiologically meaningful model for analysis of the Shh signaling pathway.

TABLE 1

Luciferase activity from a Gli-dependent reporter as induced by combinations of Shh pathway inducing and suppressing treatments

| | Suppressor | | | | | |
|---|---|---|---|---|---|---|
| Inducer | None | Ptc | cyclopamine | forskolin | PKA | Gli3-N |
| None | − | − | − | − | − | − |
| ShhN$_p$ | +++ | + | − | − | − | − |
| Smo | + | − | − | − | − | ND |
| activated Smo | +++ | +* | +* | − | − | − |
| Gli2 | ++ | ++ | ++ | ++ | + | − |

Figure 2D:
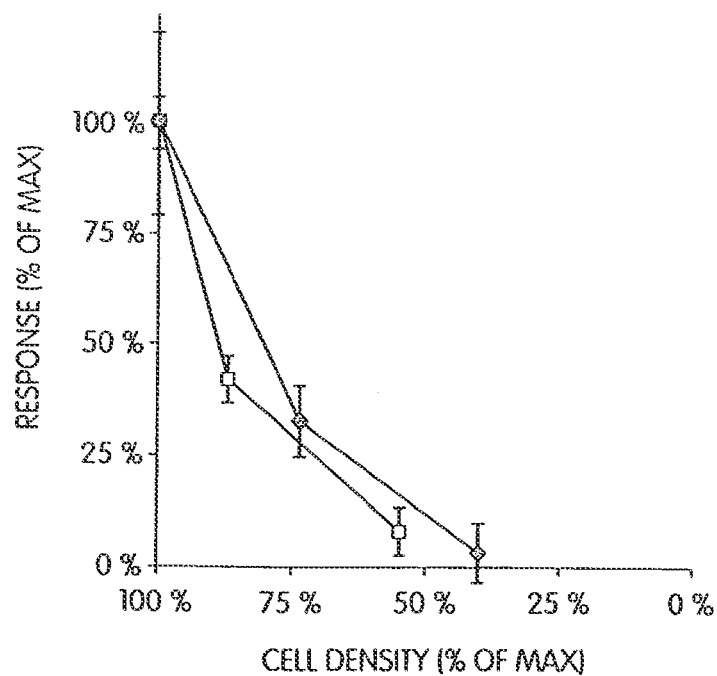

*Higher than normal dose required to completely suppress
Gli3-N = Gli3 truncated at residue 700, generating a repressor form
Expression constructs used: pRK5 for full length mouse Ptc1, C-terminally truncated Ptc1-CTD, Gli3 (1-700) repressor and active PKA cDNAs, and pGE (transient transfections) or pcDNA3.1 + hygro (stable lines; Invitrogen) for the various Smo cDNAs. The CMV promoter driven mammalian expression vector pGE was derived from pEGFP-C1 (Clontech) by removing the sequences encoding the EGFP. Renilla luciferase (pRL-TK) was fused to the C-terminus of the Smo open reading frame. The resulting fusion protein constructs had comparable activity to corresponding untagged constructs in the NIH-3T3 assay We then made several clonal NIH-3T3 cell lines that contain stably integrated reporter. In the best-responding cell lines, we observed 20-60 fold induction of luciferase activity by ShhN$_p$. Using these cell lines, we found that a full response to ShhN$_p$ required that cells have reached saturation density, with a reduction in response observed for less dense cultures (FIG. 2D). The requirement for saturation density also applied to Shh response in NIH-3T3 cells transiently transfected with luciferase reporter (not shown), and to reporter activation by expression of activated Smo (FIG. 2D), but not to induction by Gli1 overexpression (not shown).

Figure 3A:
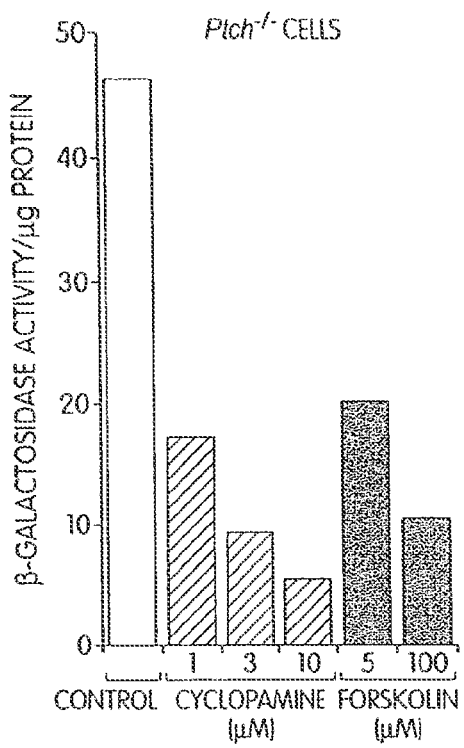
FIG. 3 demonstrates how cyclopamine acts by inhibiting the activity of Smo. (A) Ptc1−/− cells are sensitive to cyclopamine. Fibroblasts from Ptc1−/− embryos were treated with cyclopamine or forskolin as indicated. After 3 d, cells were lysed and β-galactosidase activity relative to protein concentration was measured. Since β-galactosidase is expressed from the Ptc1 locus, its expression reflects the activity of the Shh pathway. A representative experiment is shown. (B) Activated mutants of Smo are resistant to cyclopamine. Cultures of NIH-3T3 cells were transfected (in triplicate) with Gli-luciferase reporter, TK-*Renilla* luciferase control vector and Smo or SmoA1 expression vectors. Smo DNA was used at 50% w/w, and SmoA1 at 50%, 5%, and 0.5% w/w. Subsequently, the cultures were treated with 5 μM cyclopamine for 2 d. Error bars indicate one standard deviation. The leftmost four bars, shown for comparison, are as in FIG. 2C. (C) High level expression of Ptc1 restores cyclopamine resistant response of SmoA1 to ShhNp. NIH-3T3 cells were transfected with Gli-luc reporter, TK-*Renilla*, Ptc1CTD and SmoA1 expression vectors (Ptc to Smo DNA ratio=9). Subsequently, the cultures were treated with ShhNp (2 nM), cyclopamine (5 μM) and/or forskolin (100 μM) as indicated for 2 d. Note that SmoA1 activation of pathway is dramatically reduced by high levels of Ptc1 activity (compare to panel B), and that 2 nM ShhNp restores pathway activity even in the presence of 5 μM cyclopamine. A representative experiment is shown. Tumor-derived mutant Smo proteins are intrinsically more active than wild type Smo. NIH-3T3 cells were cotransfected with Gli-luc reporter, β-galactosidase transfection control, and a control vector or an expression vector encoding the indicated Smo-*Renilla* luciferase fusion protein. In the representative experiment shown, Shh pathway activity and Smo protein levels were measured as firefly and *Renilla* luciferase activities relative to β-galactosidase, respectively. Epitope-tagged Smo and activated Smo proteins also displayed similar levels of expression in these cells (not shown).

The steroidal nature of these plant teratogens and their ability to disrupt cholesterol synthesis and/or transport (P. A. Beachy et al., *Cold Spring Harb Symp Quant Biol* 62, 191 (1997); Y. Lange, J. Ye, M. Rigney, T. L. Steck, *J Lipid Res* 40, 2264 (1999)) suggested the possibility that they may affect the action of Ptc1, which contains an apparent sterol sensing domain (S. K. Loftus et al., *Science* 277, 232 (1997)). Having established the characteristics of Shh response and cyclopamine inhibition in mouse embryonic fibroblasts, we assayed fibroblasts derived from Ptc1−/− mouse embryos for sensitivity to cyclopamine. Mice lacking function of Ptc1 display widespread activation of targets of Shh signaling, including of the Ptc1 gene itself (L. V. Goodrich, L. Milenkovic, K. M. Higgins, M. P. Scott, *Science* 277, 1109 (1997)). As β-galactosidase is expressed under the control of the Ptc1 promoter in these cells, β-galactosidase expression can be used to assay the state of Shh pathway activity (FIG. 3A). Surprisingly, addition of cyclopamine to Ptc1$^{-/-}$ cells significantly suppressed β-galactosidase expression (FIG. 3A) and similarly suppressed activity of the Gli-Luc reporter (not shown), indicating that cyclopamine is able to suppress Shh pathway activity in the absence of Ptc1 function. In contrast, cyclopamine failed to prevent pathway activation induced by Gli2 overexpression (Table 1). These results suggest that the target of cyclopamine action is not Ptc1 (Ptc2 is not a likely target of cyclopamine in Ptc1−/− cells, as expression of the Ptc2 protein suppresses pathway activation and the pathway is maximally activated in Ptc1−/− fibroblasts (data not shown)), but likely another pathway component that functions somewhere between Ptc1 and the Gli proteins.

Figure 3B:
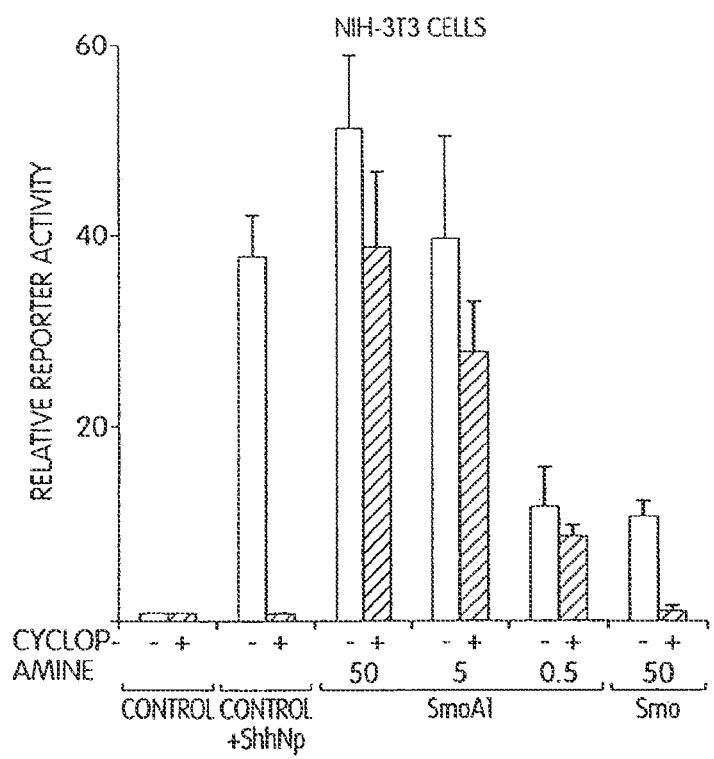
Figure 3C:
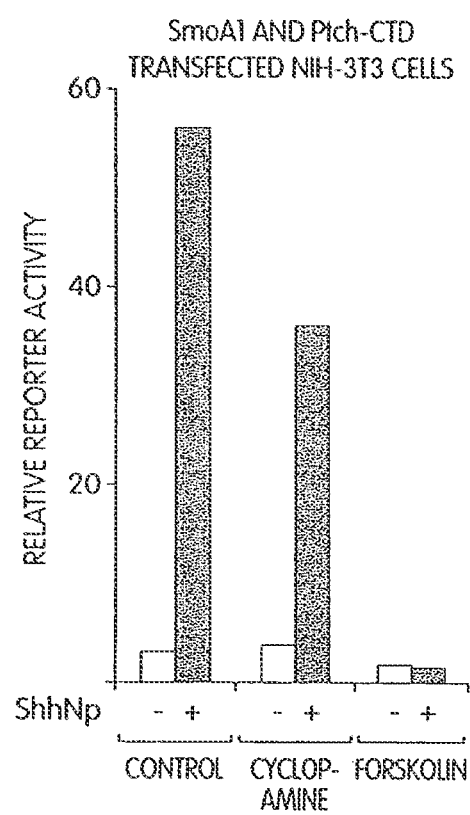

To further investigate the site of cyclopamine action we transfected NIH-3T3 cells with Smo cDNA (a mouse Smo cDNA probe was generated using RT-PCR with degenerate oligonucleotide primers based on rat and human Smo sequences; this probe was subsequently used to isolate a cDNA clone containing the complete coding sequence of mouse Smo), and found that overexpression of Smo in the absence of Shh induces reporter expression ~10-fold. As this activation of the pathway occurs in the absence of Shh and can be suppressed by 5 µM cyclopamine (FIG. 3B), we infer that the mechanism of cyclopamine action is not direct interference with Shh binding (i.e., as a neutral antagonist of Shh). Interestingly, cyclopamine at this concentration showed little effect on reporter expression induced by the tumor-derived activated Smo mutants (FIG. 21B), suggesting the possibility that cyclopamine acts directly or indirectly upon Smo and that activating mutations render Smo proteins resistant. Cyclopamine resistance of SmoA1 also was observed at sub-maximal levels of pathway activation associated with reduced SmoA1 expression (FIG. 3B). In addition, we tested whether Shh signaling through activated Smo is affected by cyclopamine. Although activated Smo proteins previously have been reported to resist suppression by Ptc1 (M. Murone, A. Rosenthal, F. J. de Sauvage, Current Biol. 9, 76 (1999)) we found that this resistance is partial, as transfection of a 9 to 1 ratio of a Ptc1 construct (not shown) or of Ptc1-CTD, a C-terminally deleted construct (Ptc1-CTD previously was shown to be expressed at higher levels than Ptc1; N. Fuse et al., Proc Natl Acad Sci USA 96, 10992 (1999)), can completely inhibit the activating effects of SmoA1 or SmoA2 (FIG. 3C). In cells thus transfected, the Gli-responsive reporter can be induced upon treatment with ShhN$_p$; induction under these circumstances is resistant to 5 µM cyclopamine (FIG. 3C), which normally would abolish Shh signaling. These results indicate that activated Smo molecules in the presence of sufficiently high levels of Ptc1 can contribute to an essentially normal, albeit cyclopamine resistant, response to the Shh signal. The requirement for higher levels of Ptc1 is not due simply to a higher level of the Smo protein variant, as we found that the levels of wild type and activated Smo proteins produced in transfected cells were similar, despite dramatically elevated levels of reporter activity associated with activated Smo (FIG. 3D).

Figure 4A:
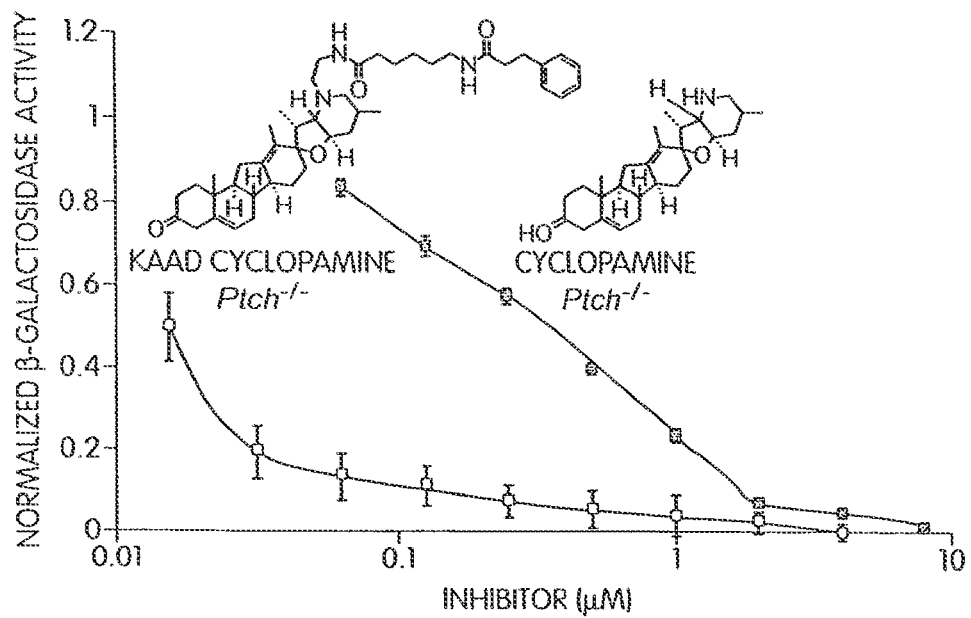
FIG. 4 depicts a cyclopamine derivative of increased potency. (A) 3-Keto, N-aminoethyl aminocaproyl dihydrocinnamoyl cyclopamine (KAAD cyclopamine) was synthesized from cyclopamine. Structure of KAAD cyclopamine was verified by NMR and mass spectrometry analyses. KAAD cyclopamine can block pathway activation by tumor-derived Smo. Shh-LIGHT2 (diamonds) and SmoA1-LIGHT (circles) cells were treated with 4 nM ShhN$_p$ (Shh-LIGHT2) and increasing concentrations of KAAD cyclopamine (both lines) for 2 d. Relative reporter activity is normalized to maximum. Note the increased inhibitory potency of KAAD cyclopamine as compared to cyclopamine in FIG. 3 A-C. (B) KAAD cyclopamine can block pathway activation in Ptc1-/- cells. p2$^{PTC-/-}$ cells (these cells are a cloned line derived from Ptc-/- mouse embryonic fibroblasts) were treated with increasing concentrations of cyclopamine (open boxes) or KAAD cyclopamine (filled boxes) for 2 d. The suppression of pathway activity induced by SmoA1-*Renilla* by high concentrations of cyclopamine derivatives did not involve a decrease in the level of expression of the Smo construct (not shown). Cells were seeded into duplicate 96-well plates, allowed to grow to saturation density, and incubated with cyclopamine and KAAD cyclopamine for 2 d. β-galactosidase activity was determined using Galacto-Light kit (no inactivation of endogenous β-gal activity, Tropix). β-galactosidase activities were normalized to cell mass as determined from a treated duplicate plate using the Cell Titer 96AQ assay (Promega). Maximum normalized β-galactosidase activities (1103 for KAAD-cyclopamine and 916 for cyclopamine) were set to 1 and minimum activities (191 and 144, respectively) were set to 0, Significant toxicity (microscopically visible cell death, or decrease in Cell Titer reading) was not observed, even at the highest doses of compounds used. β-galactosidase activity is normalized to the maximum. Error bars in A and B indicate one standard deviation.
Figure 4B:
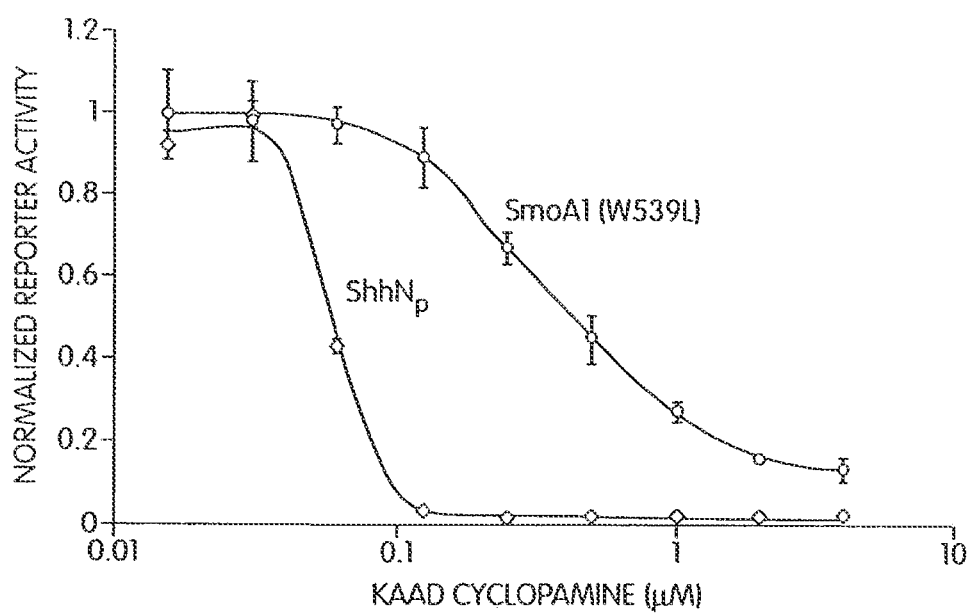
Figure 5A:
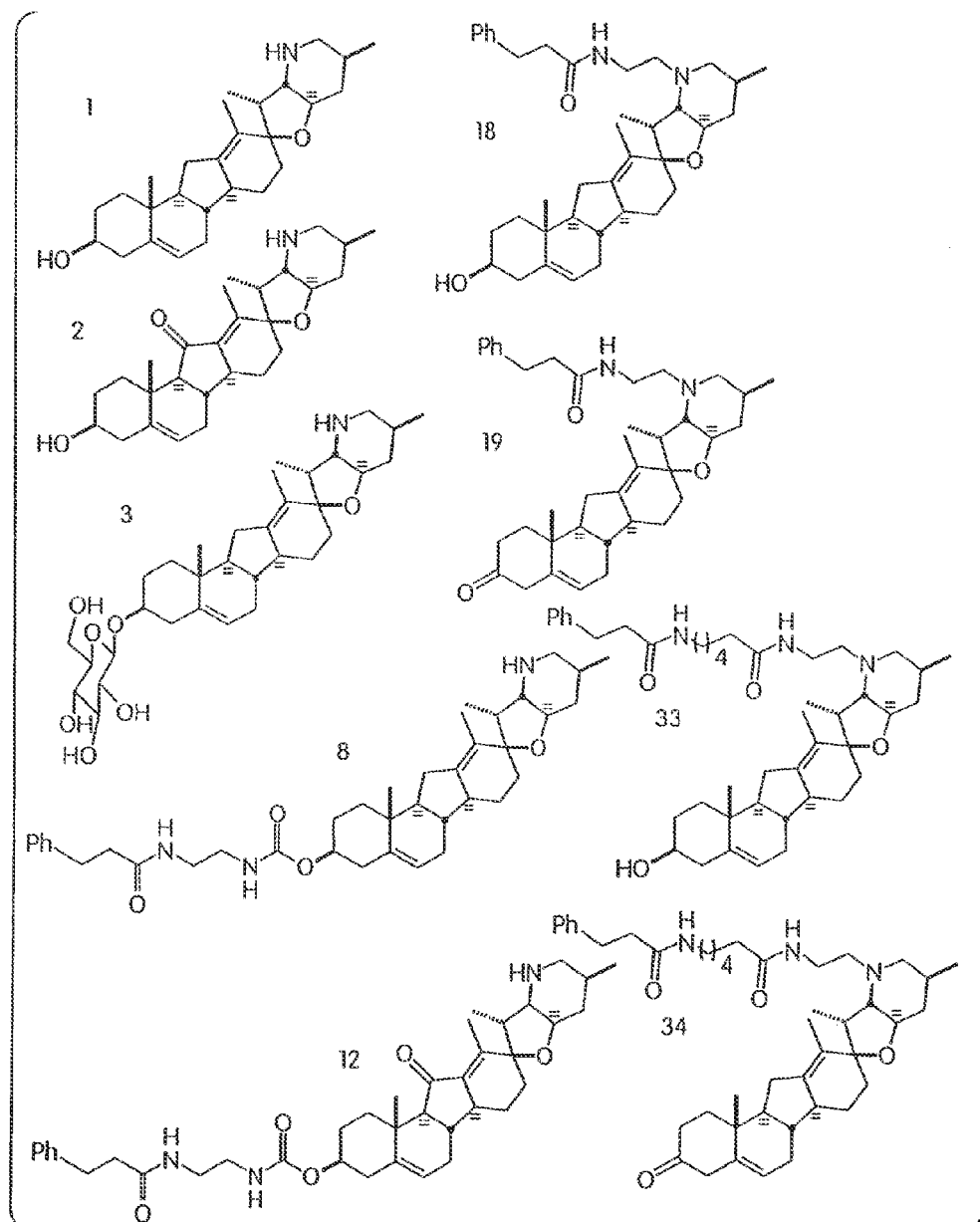
FIGS. 5A-5D present inhibitors of the Hedgehog pathway according to the present invention.
Figure 5B:
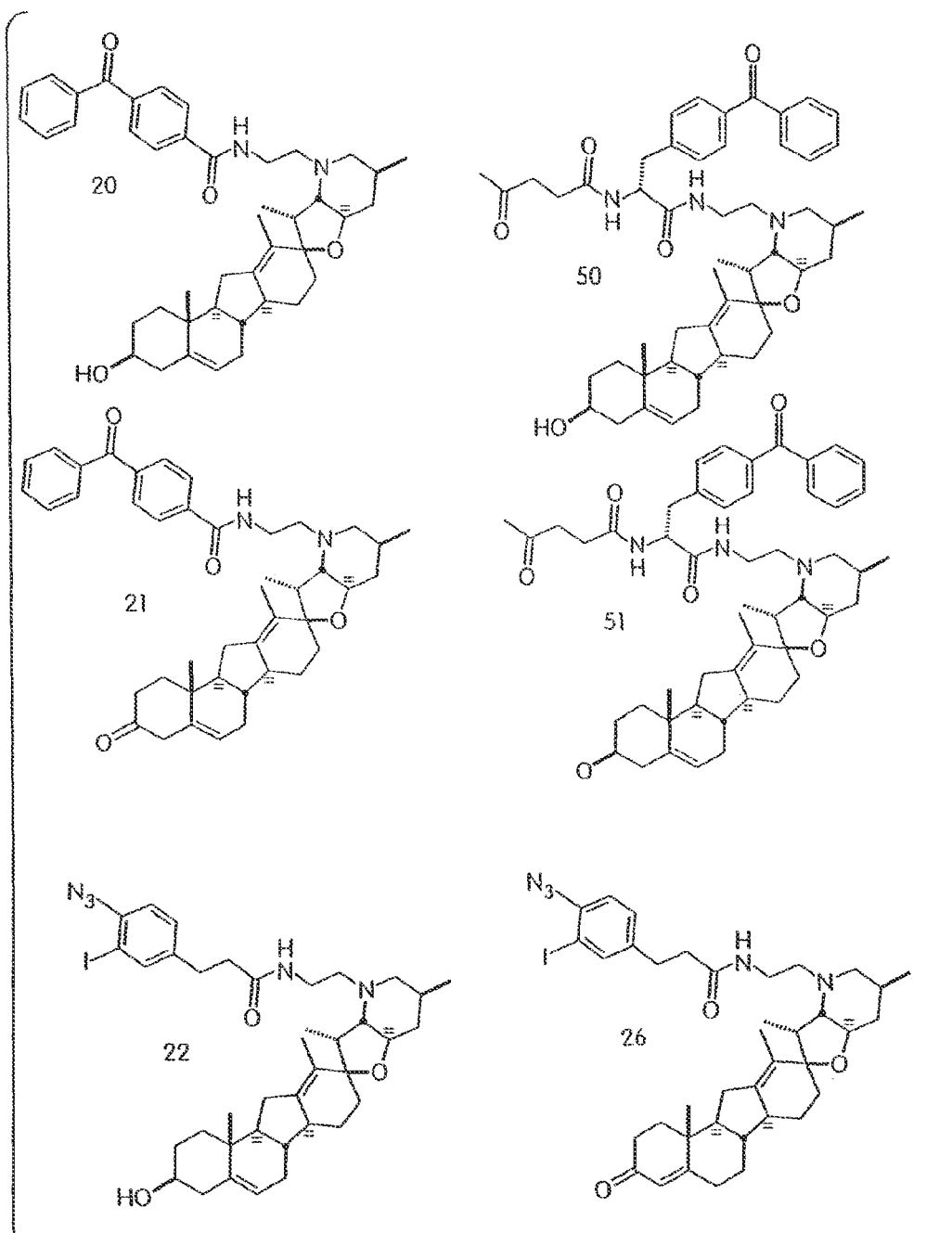
Figure 5C:
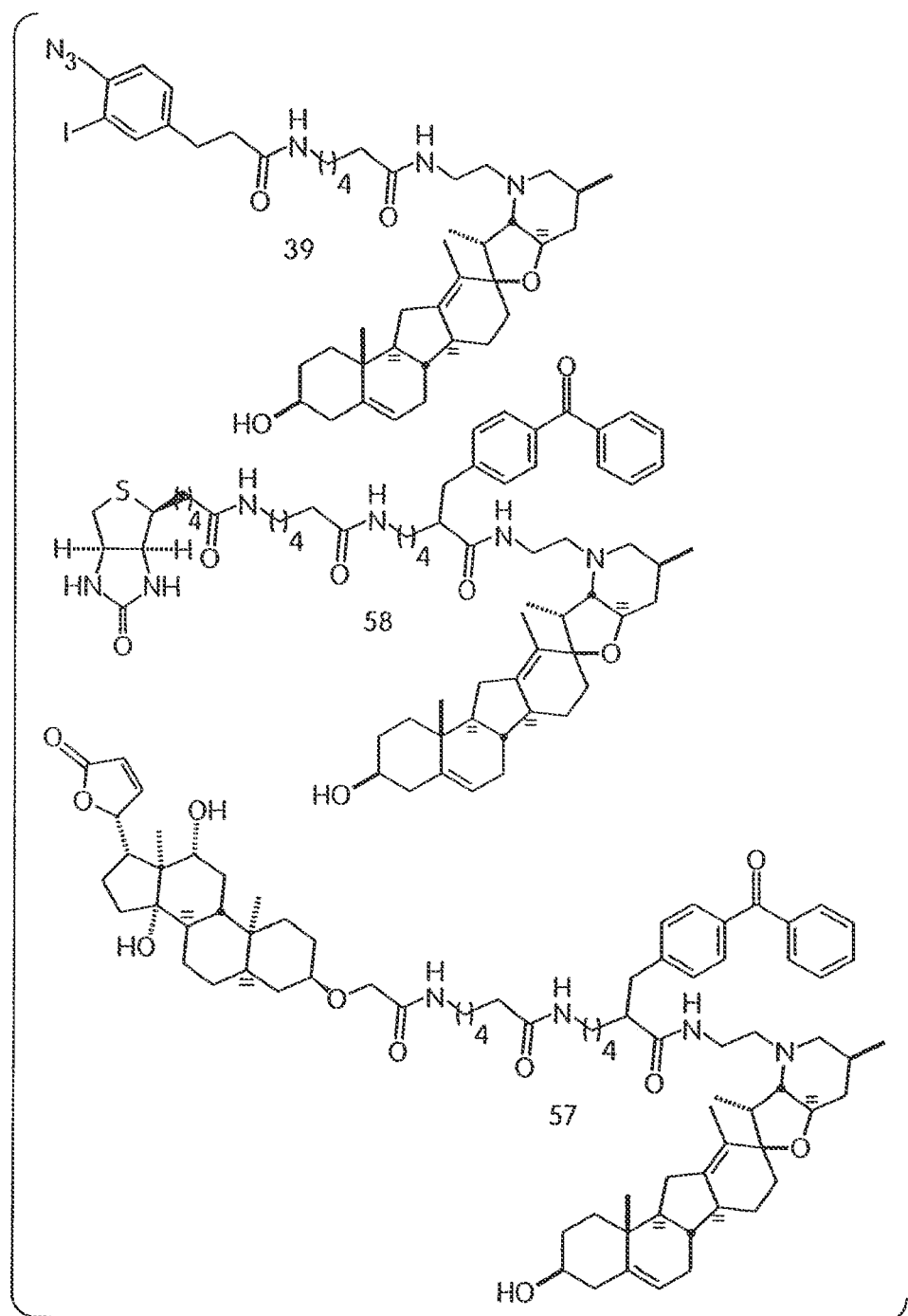
Figure 5D:
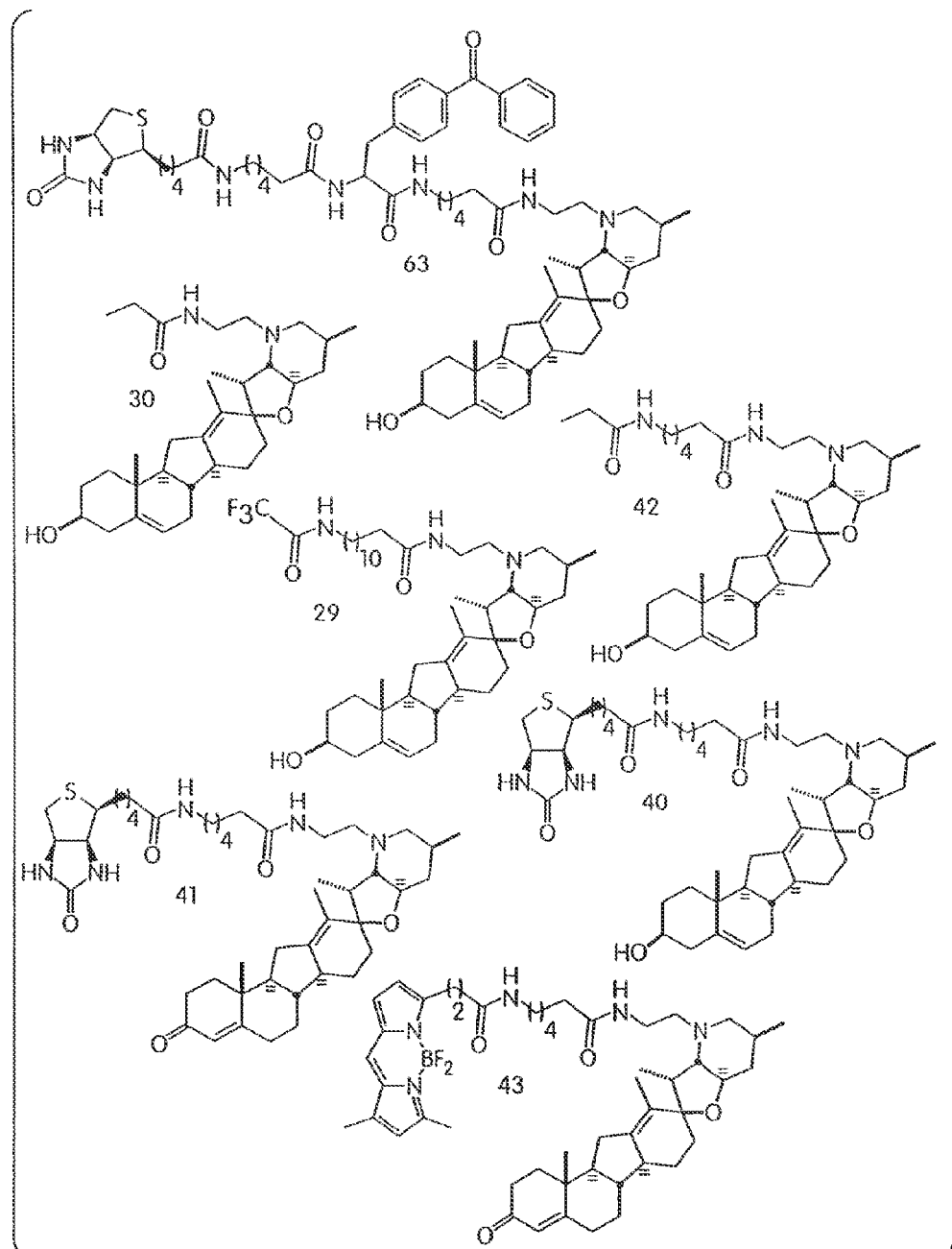
Figure 6:
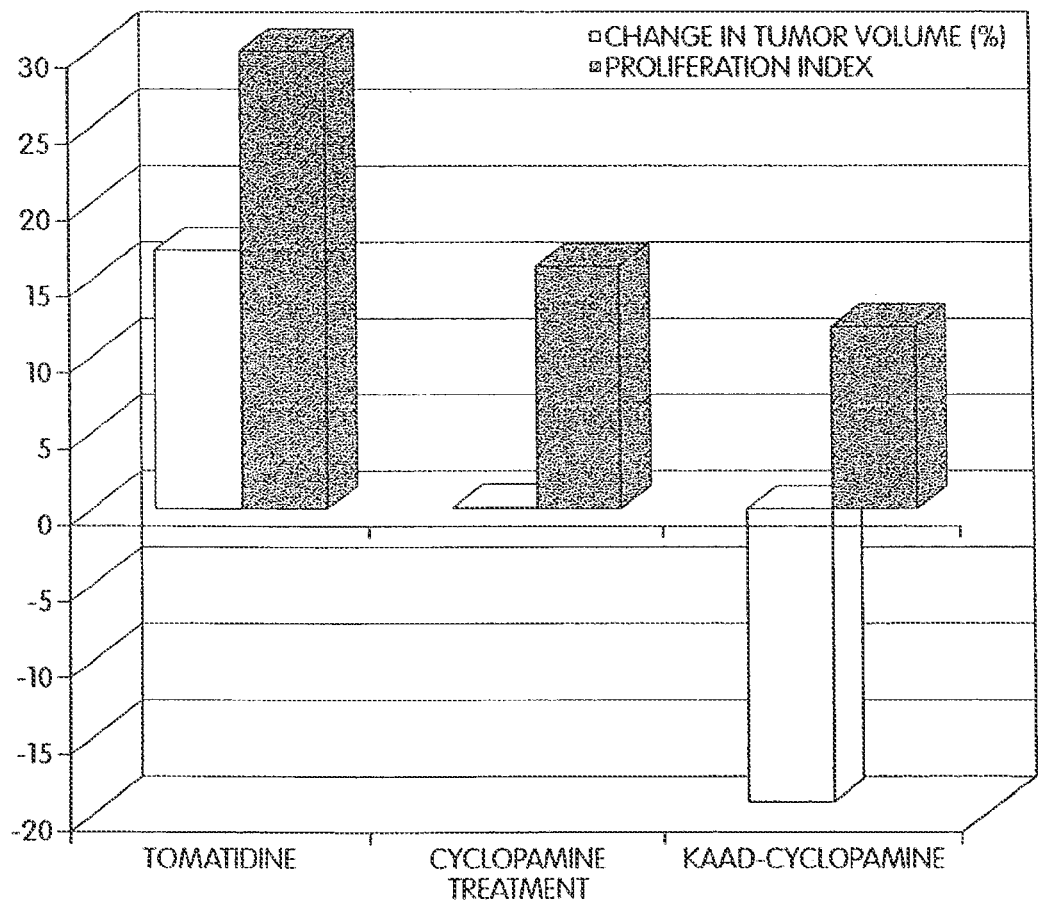
FIG. 6 depicts response of fibrosarcoma tumors to treatment with a subject compound.

Although increasing levels of cyclopamine produce some inhibition of activated Smo (although little if any inhibitory effect on activated Smo is observed at 3 µM cyclopamine (not shown), a concentration sufficient to completely inhibit normal Shh signaling, some inhibitory effect of 5 µM cyclopamine is demonstrated in FIG. 4B), complete inhibition was precluded by the toxic effects of cyclopamine that emerge in the 10-40 µM range (data not shown). However, a chemically synthesized cyclopamine derivative, 3-keto, N-aminoethyl aminocaproyl dihydrocinnamoyl cyclopamine (KAAD cyclopamine, compound 33), displayed 10-20 fold greater potency in suppression of ShhN$_p$-induced pathway activity while maintaining similar or lower toxicity (FIG. 4A). This compound suppressed SmoA1-induced reporter activity at a concentration approximately 10-fold higher than that required for suppression of ShhN$_p$ signaling (FIG. 4A) and also displayed higher potency than cyclopamine in p2$^{PTC-/-}$ cells (FIG. 4B). This more potent cyclopamine derivative thus suppresses activated Smo as effectively as high levels of Ptc1.

The simplest explanation of cyclopamine resistance as conferred by activated Smo proteins is that cyclopamine affects Smo activity and that activating mutations render Smo proteins resistant. An alternative interpretation would be that activated Smo proteins produce a high abundance of a downstream component and that a high cyclopamine level is required to suppress the increased concentration of this downstream component. This alternative model, however, can not account for the sustained cyclopamine resistance of activated Smo proteins observed at intermediate or low levels of pathway activation (FIG. 3B) (production by activated Smo of high levels of a downstream component that is the cyclopamine target can not explain the sustained cyclopamine resistance observed at intermediate levels of pathway activation (FIG. 3B), as the hypothetical cyclopamine target in this circumstance would be present at the same moderate levels as those produced by ShhN$_P$ signaling via unaltered Smo. We also find that high levels of Smo in maximally-stimulated cells do not confer cyclopamine resistance (not shown), again inconsistent with the notion that extensive production or activation by Smo of a downstream component can confer cyclopamine resistance). As activated Smo is not expressed at higher levels than unaltered Smo (FIG. 3D), it would appear that activating mutations may confer a higher intrinsic ability to activate the pathway. This suggests that, like other seven transmembrane receptors (R. A. Bond et al., Nature 374, 272 (1995); H. R. Bourne, Curr Opin Cell Biol 9, 134 (1997)), Smo may exist in a balance between active and inactive forms. Cyclopamine and Ptc activities might shift this balance toward the inactive state and tumor-associated mutations toward the active state, thus accounting for the higher levels of Ptc and cyclopamine activity required to suppress activated Smo proteins.

Cyclopamine appears to impact the Shh pathway at the level of Smo activity (see above), but this action need not be direct and could operate through an effect on molecules involved in intracellular transport, on molecules that affect posttranslational modification of Smo, or on other molecules that impact Smo activity. Such indirect action of cyclopamine would not necessarily be inconsistent with a conformational transition between active and inactive Smo, as conformational state could be coupled by a variety of mechanisms to subcellular localization or state of covalent modification. Whatever the mechanism, such inhibitors may have utility in treatment of disorders caused by inappropriate Shh pathway activation. Patients with Basal Cell Nevus Syndrome (also termed Gorlin's syndrome), an autosomal dominant disorder associated with heterozygous loss-of-function mutations in the human Ptc1 gene, display increased incidence of numerous tumors, most notably basal cell carcinoma (BCC), medulloblastoma, rhabdomyosarcoma and fibrosarcoma. Loss-of-function mutations in Ptc1 or activating mutations in Smo in addition are found in ~40% of sporadic BCC and ~25% of primitive neuroectodermal tumors. The ability of cyclopamine and its derivatives to block pathway activation by both of these types of mutations suggests that these plant-derived compounds or others that influence the activity of Smo may be valuable as therapeutic agents.

Example 2

Steroid Derivatives

New Derivatives Synthesized

Cyclopamine and jervine (structures 1 and 2 of FIG. 5, respectively) are closely related plant-derived steroidal alkaloids known to specifically inhibit the Sonic hedgehog signaling pathway (Cooper et al., Science 280, p. 1603-1607, 1998). We have synthesized chemically 23 new derivatives of these two compounds, by various modifications of its secondary amine, the C-3 oxygen, and/or the C5-C6 olefin. Some of these compounds can be readily synthesized in labelled form, thus making them useful for binding studies. Some of these compounds also contain functional groups useful for photo-activatable cross-linking and consequent radiolabelling or attachment of a biotin moiety to target proteins. One of the compounds is fluorescently labelled, and may be useful for direct observation of the cellular target of cyclopamine action. The potency of the various derivatives is set forth in Table II.

TABLE II

| Compound | $IC_{50}$ |
|---|---|
| 1 | >100 nM |
| 2 | >100 nM |
| 3 | >1 μM |
| 12 | >10 μM |
| 18 | >100 nM |
| 19 | >10 nM |
| 20 | >100 nM |
| 21 | >10 nM |
| 22 | >1 μM |
| 26 | >100 nM |
| 29 | >100 nM |
| 30 | >100 nM |
| 33 | >10 nM |
| 34 | >10 nM |
| 39 | >100 nM |
| 40 | >100 nM |
| 41 | >100 nM |
| 42 | >100 nM |
| 43 | >100 nM |
| 50 | >1 μM |
| 51 | >1 μM |
| 57 | >10 μM |
| 58 | >10 μM |

Realization of Improved Potencies Through SAR Studies

Using a clonal cell line derived from parental NIH-3T3 fibroblast cells that contains a stably integrated Shh-responsive luciferase reporter, we have determined the concentration of each compound required to achieve 50% inhibition of Sonic hedgehog induction (IC50). Through SAR studies we have found that adducts to the 3,β-hydroxyl dramatically reduce activity, whereas oxidation of the 3,β-hydroxyl to a keto group increases potency. We have also found that addition of bulky groups to the secondary amine reduces potency, but that longer aliphatic linkers not only permit addition of such bulky groups but also enhance potency. The most active compound thus far identified (structure 34 in FIG. 5; IC50=30 nM) displays a potency ten-fold greater than that of cyclopamine (structure 1; IC50=300 nM). It should be straighforward to achieve even greater potencies by systematically testing various adducts to the secondary amine and combining these in combination with a 3-keto functionality. The more potent derivatives we have already synthesized display the desirable property of achieving inhibition of Shh signaling with much reduced toxicity as compared to the parent compounds.

Broad Utility of Compounds

We have determined that these compounds are capable of blocking pathway activity in cells with elevated levels of pathway activity due to lack of function of the Patched1 (Ptc1) protein, or to constitutively activated function of the Smo protein. The ability of these compounds to block pathway activity in cells with both of these types of defects suggests that they may be broadly useful in the treatment of certain sporadic tumors or in prophylactic treatment of patients with an inherited disposition to high frequency formation of these tumors. Such tumors include but are not limited to basal cell carcinoma, medulloblastoma, fibrosarcoma, and rhabdomyosarcoma. Additional applications for these compounds include but are not limited to induction of pancreatic tissue, elimination of excessive hair growth, and treatment of other skin disorders.

Response to the Hh signal is controlled by two transmembrane proteins, Patched (Ptc) and Smoothened (Smo). Ptc is a twelve-span transmembrane protein that binds directly to Hh. Smo contains seven transmembrane spans, is related to the Frizzled family of Wnt receptors, and is related more distantly to members of the G-protein coupled receptor family. Genetic evidence indicates that Ptc suppresses the activity of Smo; Hh relieves this suppression and allows activation of downstream targets, including the Ci/GLI family of transcriptional effectors.

The Ptc1 protein is involved in suppressing pathway activity, and cells lacking it display constitutively high levels of pathway activation. A lack of Ptc1 function is causally associated with a high percentage of sporadic basal cell carcinoma, medulloblastoma, fibrosarcoma, rhabdomyosarcoma, as well as other tumors. In addition familial heterozygosity at the Ptc1 locus is associated with a predisposition to high frequency formation of these tumors. We have shown that cyclopamine, jervine, and related compounds are capable of fully suppressing pathway activity in cells lacking Ptc function.

The Smo protein is required for pathway activation, and certain mutations of the Smo locus result in constitutive pathway activity, even in the absence of Shh stimulation. We have found that cells expressing such activated Smo proteins are somewhat resistant to these compounds, but can still be suppressed at levels between one and two orders of magnitude higher than those required for suppression of normal cells stimulated with Shh protein. Thus, tumors associated with sporadic activating mutations at the Smo locus may also be responsive to treatment with these compounds.

Summary of Structure-Activity-Relationship (SAR) Data.

Modifications to cyclopamine (1) and jervine (2) are most efficiently accomplished at heteroatom positions, namely the secondary amine and the secondary alcohol. Our initial investigations of alkaloid derivatives therefore focused upon the chemical synthesis of such heteroatom modifications and the biological evaluation of these novel compounds. Using standard synthetic procedures and a cell-based Shh signaling assay, it was determined that the conjugation of chemical groups to the steroid alcohol through a carbamate linkage effectively diminishes Shh inhibitory activity; C3-OH modified compounds 8 and 12 exhibit IC50s in the cell-based assay that are nearly 100 times higher than those of cyclopamine. These carbamate-containing compounds are also 10 times weaker than cycloposine (3), which has a more labile modification of the C3-OH group, suggesting that the observed inhibitory activity of cycloposine is actually due to partial hydrolysis of the glycosidic linkage.

In contrast, certain modifications of the secondary amine that preserve the basicity of this moiety are accommodated by the cyclopamine target. All N-alkyl derivatives in this study were synthetically obtained through the diamine intermediate 17, which allows for the efficient preparation of numerous cyclopamine analogs. Even medium-sized structural elements such as those found in compounds 29, 33, 39, 40, and 43 do not significantly diminish the abilities of these alkaloids to block Shh signaling, and most additions even appear to accentuate inhibitory activity (29, 33, 39, and 43). These observations are somewhat different from those reported by Keeler and co-workers, in which small N-alkyl derivatives of cyclopamine demonstrated diminished teratogenic potential in live animals. The reasons for these differences are unclear, although they could reflect metabolic and/or pharmacologic influences in the animal-based studies. There are still limitations, however, on the type of N-alkyl structures that are accepted by the cyclopamine target, according to our cell-based assays. Compounds with large steric bulk are unable to block Shh signaling at concentrations up to 15 μM (derivatives 57, 58, and 63), either due to cell membrane impermeability or steric exclusion from the cyclopamine-interacting site. Even relatively small, branched elements close to the cyclopamine skeleton significantly abrogate biological activity (compound 50).

These compounds illustrate the variety of N-modifications that are accepted by the cyclopamine target. It should be noted, however, that oxidation of the hydroxyl group to a ketone consistently improves the inhibitory activities of the cyclopamine derivatives by approximately two-fold (see compound 18 vs. 19; 20 vs. 21; 22 vs. 26; 33 vs. 34; 40 vs. 41; and 50 vs. 51). Formation of the enone by migration of the C5-C6 olefin to the C4-C5 position (see compounds 26 and 41) does not appear to affect compound potency, suggesting that the importance of unsaturation at the $C_5$-$C_6$ position reported by Keeler and co-workers is primarily due to $sp^2$-hybridization at the C5 carbon. Collectively, these SAR data have facilitated the synthesis of potent Shh signaling inhibitors (for example, compound 34 is the most potent Shh inhibitor known to date), radiolabeled-probes (30 and 39), photoaffinity reagents (39 and 41), and fluorophores (43).

Most significantly, the compounds described in this study exemplify the facility by which derivatives of cyclopamine can be synthesized and evaluated. The versatile intermediate 17 should promote the development of further cyclopamine-based molecules, expediting the discovery of derivatives with desirable pharmacological properties. Such cyclopamine analogs could also be rapidly prepared through combinatorial synthetic approaches; the cyclopamine skeleton of 17 could be immobilized on a solid support via the C3-OH, and structurally diverse functionalities could be conjugated to the primary amine in a repetitive split-and-pool manner. In principle, this strategy would permit the simultaneous synthesis of millions of cyclopamine derivatives in a format amenable to high throughput screening.

Preparation of Compounds

General Synthetic Procedures.

All reactions were performed under a positive pressure of nitrogen. Air and moisture sensitive compounds were introduced via syringe or cannula through a rubber septum. All reagents and solvents were analytical grade and used as received with the following exceptions. DMF and DMSO were stored over 4 Å molecular sieves, and water was de-ionized and distilled. Flash chromatography purifications were performed with the indicated solvent system on Merck silica gel 60 (230-400 mesh). Low and high resolution mass spectra were obtained by the Mass Spectrometry Facility at the Harvard Department of Chemistry and Chemical Biology. Proton magnetic resonance spectra ($^1$H NMR) were recorded on a Varian 500 MHz spectrophotometer.

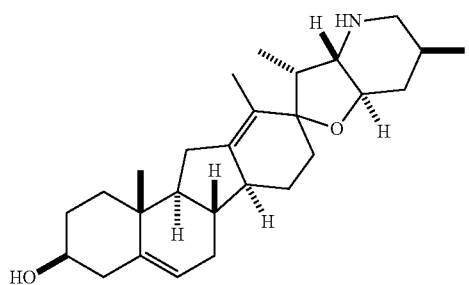

1

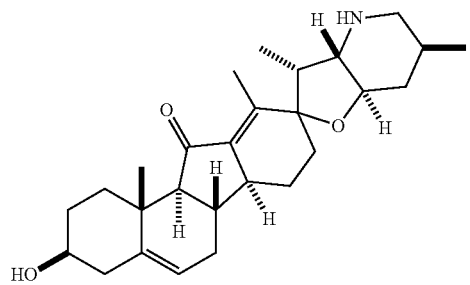

2

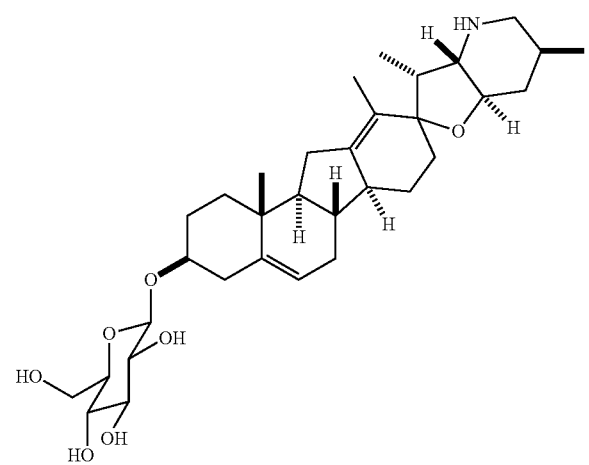

3

Isolation of Crude Cyclopamine (1)

A benzene extract of *Veratrum californicum* (6.06 g) obtained from the United States Department of Agriculture was purified by flash chromatography (SiO$_2$, step-wise gradient from 50:1 to 6.25:1 dichloromethane/ethanol to yield crude cyclopamine as a light brown solid (460 mg, approximately 1.12 mmoles). $^1$H NMR: spectrum confirms the isolation of cyclopamine along with some impurities.

Isolation of Crude Jervine (2).

A benzene extract of *Veratrum virides* (1.1 g) obtained from the United States Department of Agriculture was purified by flash chromatography (SiO$_2$, step-wise gradient from 50:1 to 6.25:1 dichloromethane/ethanol) to yield a brown oil (550 mg). The residue was then recrystallized in ethanol/water (35 mL; 1:1) to yield a slightly yellow solid (215 mg, approximately 505 μmoles). Concentration and recrystallization of the mother liquor yielded another batch of crude jervine (101 mg, approximately 237 μmoles) $^1$H NMR: spectrum confirms the isolation of jervine along with some impurities.

Cyloposine (3).

Cycloposine was obtained from the United States Department of Agriculture as a white solid.

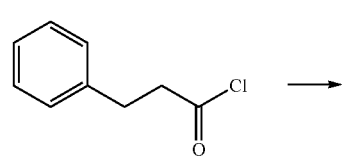

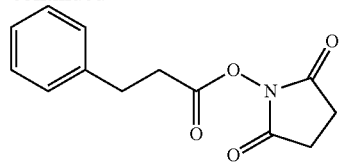

Dihydrocinnamic acid N-Hydroxysuccinimide ester (4)

Dihydrocinnnamoyl chloride (638 μL, 4.21 mmoles) was added dropwise to a solution of N-hydroxysuccinimide (500 mg, 4.21 mmoles) and triethylamine (704 μL, 5.05 mmoles) in dichloromethane (5 mL) at 0° C. The reaction was warmed to room temperature stirred for 1 h. The reaction mixture was then added to diethyl ether (50 mL), washed with 1 N HCl (1×20 mL) and saturated aqueous NaHCO$_3$ (1×20 mL), dried over MgSO$_4$, and concentrated in vacuo to yield a white solid (1.03 g, 4.17 mmoles, 99%). HRMS: (EI+) calcd for $C_{13}H_{13}NO_4$ (M+H): 247.0845. found: 247.0841. $^1$H NMR: spectrum is consistent with the predicted structure.

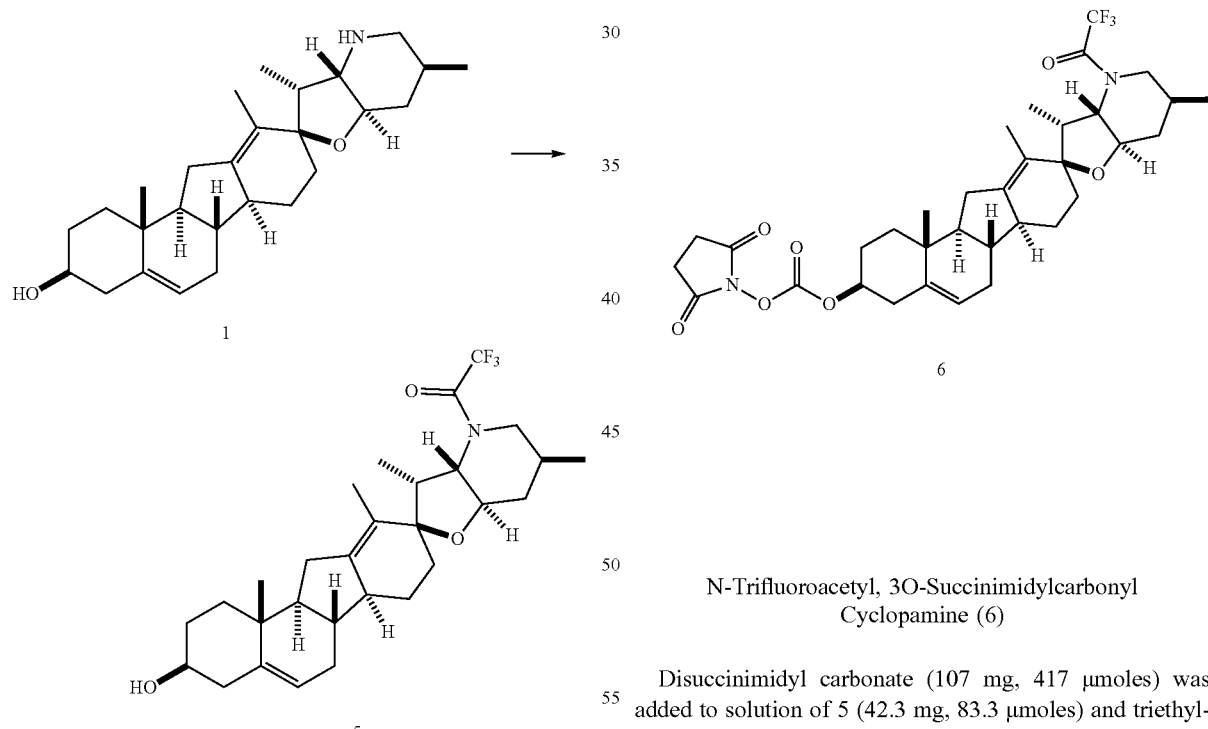

N-Trifluoroacetyl cyclopamine (5)

Trifluoroacetic anhydride (77.3 μL, 547 μmoles) was added to solution of crude cyclopamine (75.0 mg, 182 μmoles) and triethylamine (102 μL, 729 μmoles) in dichloromethane (0.5 mL), and the mixture was stirred for 10 min at room temperature. The reaction mixture was evaporated to dryness by a stream of nitrogen gas and resuspended in MeOH (2 mL). The methanol solution was refluxed for 45 min then evaporated to dryness in vacuo. Purification by flash chromatography (SiO$_2$, step-wise gradient from 8:1 to 2:1 hexane:acetone) yielded the amide as a white solid (47.3 mg, 93.2 μmoles, 51%). LRMS: (ES+) calcd for $C_{29}H_{40}NO_3F_3$ (M+H): 508. found: 508. $^1$H NMR: spectrum is consistent with the predicted structure.

N-Trifluoroacetyl, 3O-Succinimidylcarbonyl Cyclopamine (6)

Disuccinimidyl carbonate (107 mg, 417 μmoles) was added to solution of 5 (42.3 mg, 83.3 μmoles) and triethylamine (116 μL, 833 μmoles) in acetonitrile (1.0 mL), and the mixture was stirred for 5 h at room temperature. The reaction mixture was dissolved in diethyl ether (10 mL), washed with 5% citric acid (1×2 mL) and saturated aqueous NaHCO$_3$ (1×2 mL), dried over MgSO$_4$, and concentrated in vacuo. Purification by flash chromatography (SiO$_2$, step-wise gradient from 8:1 to 2:1 hexane/acetone) yielded the carbonate as a white solid (35.6 mg, 54.9 μmoles, 66%). LRMS: (ES+) calcd for $C_{34}H_{43}N_2O_7F_3$ (M+H): 649. found: 649. $^1$H NMR: spectrum is consistent with the predicted structure.

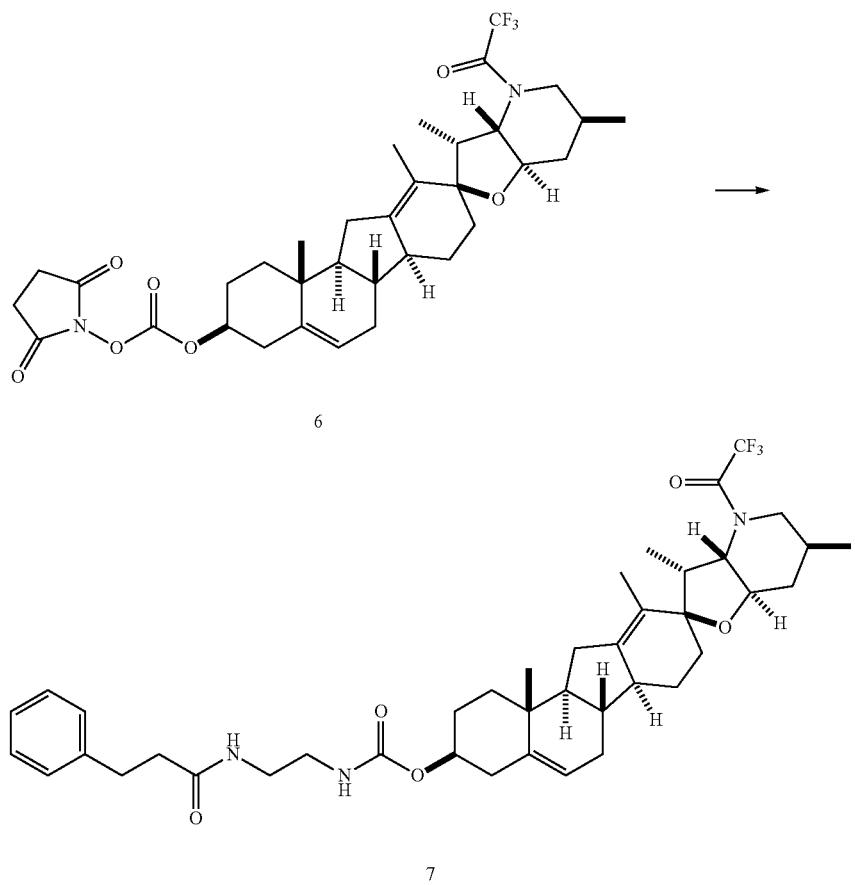

N-Trifluoroacetyl, 3O-dihydrocinnamoylethylenediaminecarbamoyl cyclopamine (7)

Ethylenediamine (22.9 µL, 342 µmoles) was added to solution of 6 (11.1 mg, 17.1 µmoles) in dichloromethane (0.5 mL), and the mixture was stirred for 15 min at room temperature. The reaction mixture was evaporated to dryness by a stream of nitrogen gas and excess ethylenediamine was removed in vacuo. The resultant residue was redissolved in dichloromethane (0.5 mL) and treated with 4 (10.6 mg, 4.28 µmoles) and triethylamine (5.97 µL, 42.8 µmoles). After stirring at room temperature for 30 min, the solution was filtered through a plug of glass wool. Purification by flash chromatography (SiO$_2$, step-wise gradient from 4:1 to 1:1 hexane/acetone) yielded the carbamate as a white solid (6.7 mg, 9.23 µmoles, 54%). LRMS: (ES+) calcd for $C_{41}H_{54}N_3O_5F_3$ (M+H): 726. found: 726. $^1$H NMR: spectrum is consistent with the predicted structure.

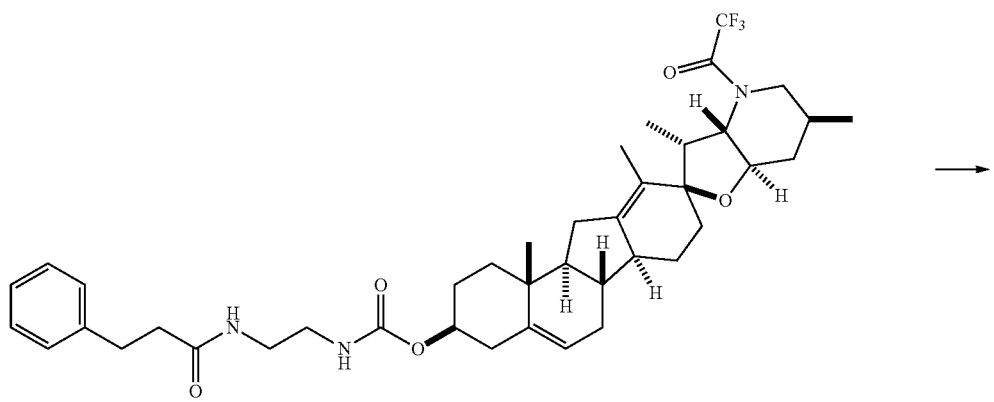

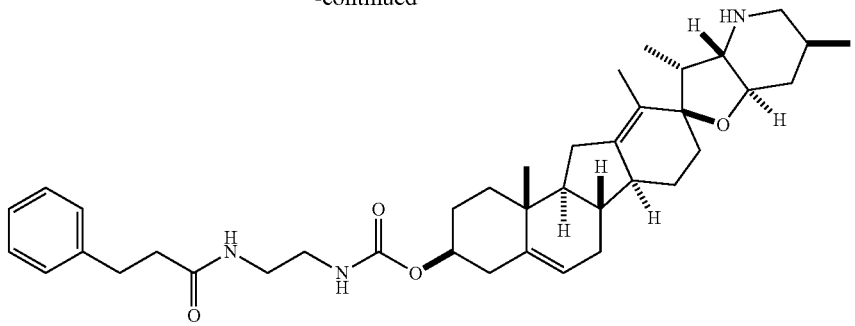

8

3O-dihydrocinnamoylethylenediaminecarbamoyl cyclopamine (8)

Compound 7 (3.0 mg, 4.13 µmoles) was dissolved in a 2 M solution of ammonia in methanol (0.5 mL, 1.00 mmoles). The reaction was stirred at room temperature for 2 h and then evaporated to dryness by a stream of nitrogen gas. Purification by flash chromatography (SiO$_2$, step-wise gradient from 20:1:0.1 to 20:2:0.1 chloroform/methanol/triethylamine) yielded the amine as a colorless oil (2.1 mg, 3.33 µmoles, 81%). LRMS: (ES+) calcd for C$_{39}$H$_{55}$N$_3$O$_4$ (M+H): 630. found: 630. $^1$H NMR: spectrum is consistent with the predicted structure.

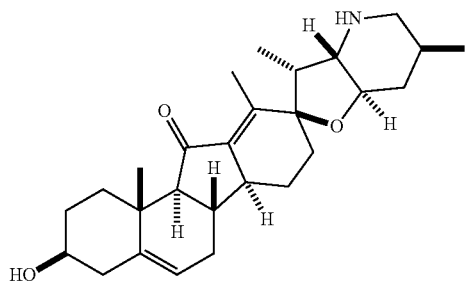

2

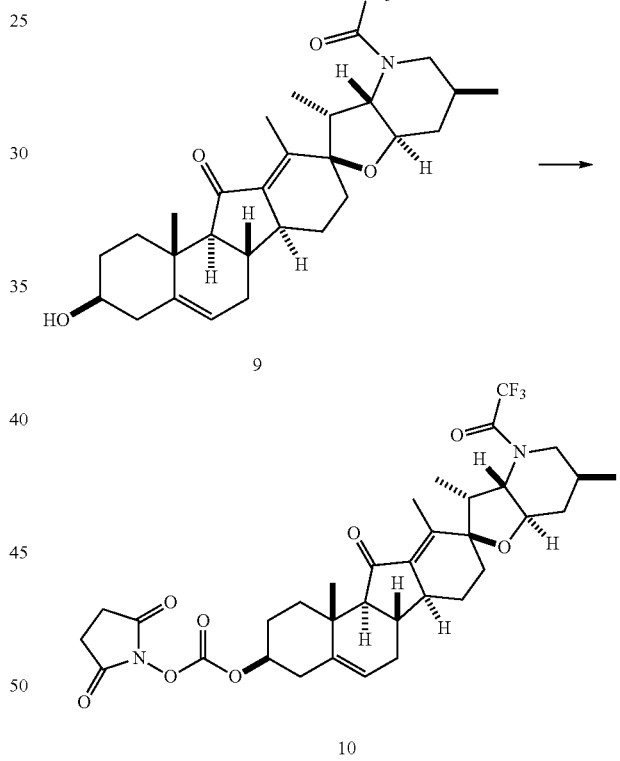

N-Trifluoroacetyl jervine (9)

Trifluoroacetic anhydride (84.4 µL, 299 µmoles) was added to solution of crude jervine (50.9 mg, 120 µmoles) and triethylamine (100 µL, 359 µmoles) in dichloromethane (0.5 mL), and the mixture was stirred for 15 min at room temperature. The reaction mixture was evaporated to dryness by a stream of nitrogen gas and resuspended in MeOH (0.5 mL). The methanol solution was stirred at room temperature for 10 min then evaporated to dryness in vacuo. Purification by flash chromatography (SiO$_2$, step-wise gradient from 16:1 to 2:1 hexane:acetone) yielded the amide as a white solid (37.8 mg, 72.5 µmoles, 60%). LRMS: (ES+) calcd for C$_{29}$H$_{38}$NO$_4$F$_3$ (M+H): 522. found: 522. $^1$H NMR: spectrum is consistent with the predicted structure.

N-Trifluoroacetyl, 3O-succinimidylcarbonyl jervine (10)

Disuccinimidyl carbonate (92.9 mg, 363 µmoles) was added to solution of 9 (37.8 mg, 72.5 µmoles) and triethylamine (101 µL, 725 µmoles) in acetonitrile (1.0 mL), and the mixture was stirred for 6 h at room temperature. The reaction mixture was dissolved in diethyl ether (10 mL), washed with 5% citric acid (1×2 mL) and saturated aqueous NaHCO$_3$ (1×2 mL), dried over MgSO$_4$, and concentrated in vacuo. Purification by flash chromatography (SiO$_2$, step-wise gradient from 8:1 to 2:1 hexane/acetone) yielded the carbonate as a white solid (38.4 mg, 57.9 µmoles, 80%). HRMS: (ES+) calcd for C$_{34}$H$_{41}$N$_2$O$_8$F$_3$ (M+Na): 685.2712. found: 685.2711. $^1$H NMR: spectrum is consistent with the predicted structure.

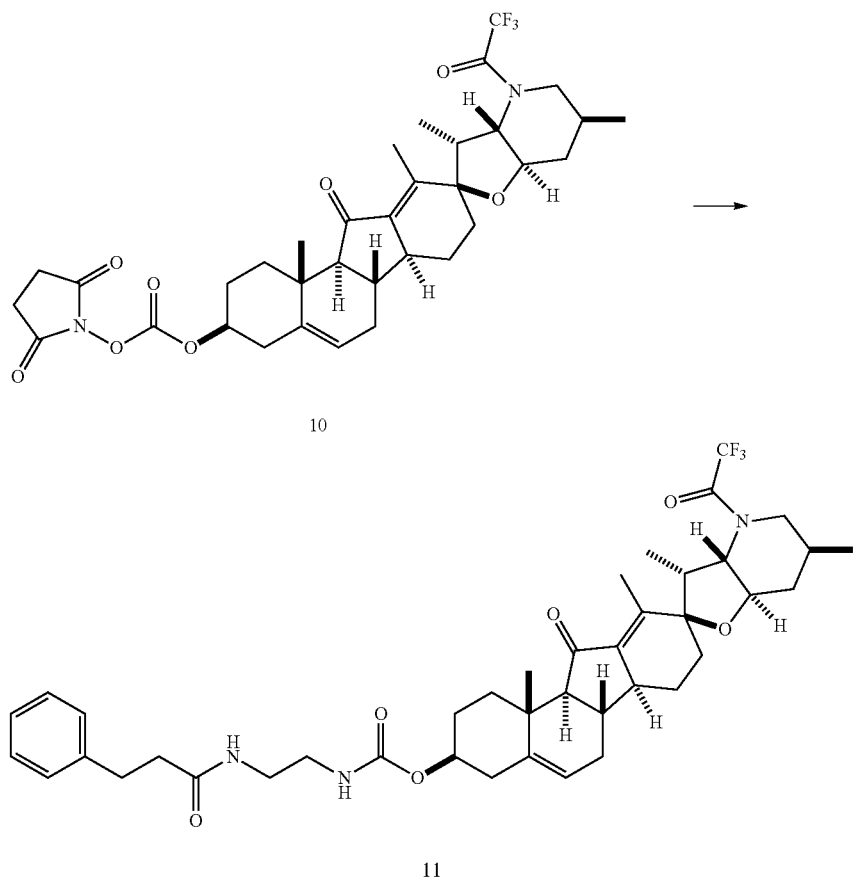

N-Trifluoroacetyl, 3O-dihydrocinnamoylethylenediaminecarbamoyl jervine (11)

Ethylenediamine (20.2 µL, 302 µmoles) was added to solution of 10 (10.0 mg, 15.1 µmoles) in dichloromethane (0.5 mL), and the mixture was stirred for 15 min at room temperature. The reaction mixture was evaporated to dryness by a stream of nitrogen gas and excess ethylenediamine was removed in vacuo. The resultant residue was redissolved in dichloromethane (0.5 mL) and treated with 4 (7.47 mg, 30.2 µmoles) and triethylamine (4.21 µL, 30.2 µmoles) at 0° C. After stirring at 0° C. for 30 min, the solution was filtered through a plug of glass wool. Purification by flash chromatography (SiO$_2$, step-wise gradient from 4:1 to 1:1 hexane/acetone) yielded the carbamate as a white solid (8.0 mg, 10.8 µmoles, 72%). LRMS: (ES+) calcd for C$_{41}$H$_{52}$N$_3$O$_6$F$_3$ (M+H): 740. found: 740. $^1$H NMR: spectrum is consistent with the predicted structure.

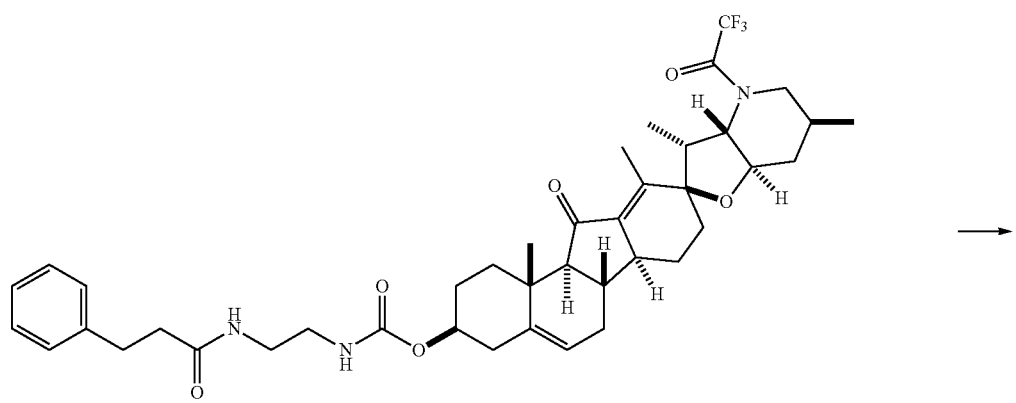

11

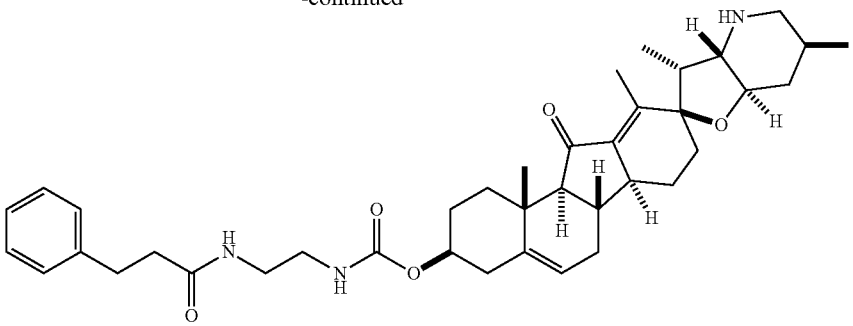

12

3O-dihydrocinnamoylethylenediaminecarbamoyl jervine (12)

Aqueous ammonia (200 µL of a 29% (w/w) solution in water, 3.04 mmoles) was added to a solution of 11 (1.0 mg, 1.35 µmoles) in methanol (200 µL). The reaction was stirred at room temperature for 30 min and then evaporated to dryness by a stream of nitrogen gas. Purification by flash chromatrography (SiO$_2$, step-wise gradient from 20:1:0.1 to 20:2:0.1 chloroform/methanol/triethylamine) yielded the amine as a colorless oil (0.8 mg, 1.24 µmoles, 92%). LRMS: (ES+) calcd for C$_{39}$H$_{53}$N$_3$O$_5$ (M+H): 644. found: 644. $^1$H NMR: spectrum is consistent with the predicted structure.

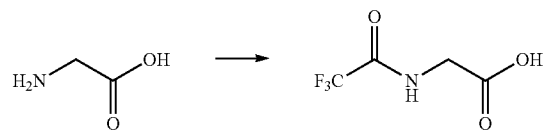

13

N-Trifluoroacetyl glycine (13)

Methyl trifluoroacetate (804 µL, 7.99 mmoles) and triethylamine (928 µL, 6.66 mmoles) were added to a suspension of glycine (500 mg, 6.66 mmoles) in methanol (2.5 mL). After the mixture was stirred vigorously for 18 h, 1 N HCl was added dropwise until the a pH of 2 was obtained. The reaction was added to ethyl acetate (30 mL) was washed with 1 N HCl (2×10 mL), dried over MgSO$_4$, and concentrated in vacuo to yield the amide as a white solid (991 mg, 5.79 mmoles, 87%). LRMS: (CI+) calcd for C$_4$H$_4$NO$_3$F$_3$ (M+NH$_4$): 189. found: 189. $^1$H NMR: spectrum is consistent with the predicted structure.

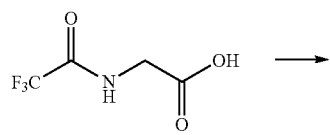

13

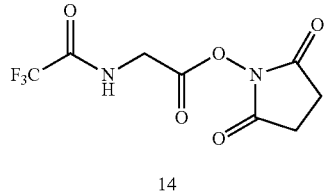

14

N-Trifluoroacetyl glycine N-hydrosuccinimide ester (14)

Disuccinimidyl carbonate (300 mg, 1.17 mmoles) was added to a solution of 13 (200 mg, 1.17 mmoles) and pyridine (94.6 µL, 1.17 mmoles) in acetonitrile (1.0 mL). The reaction mixture was stirred at room temperature for 3 h, during which the solution became clear and evolved gas. The solution was added to ethyl acetate (10 mL), washed with 1N HCl (2×5 mL) and saturated aqueous NaHCO$_3$ (2×5 mL), dried over MgSO$_4$, and concentrated in vacuo to yield a white solid (232 mg, 865 µmoles, 74%). LRMS: (ES+) calcd for C$_8$H$_7$N$_2$O$_5$F$_3$ (M+NH$_4$): 286. found: 286. $^1$H NMR: spectrum is consistent with the predicted structure.

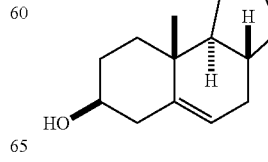

1

N-Glycyl cyclopamine (16)

Aqueous ammonia (3 mL of a 29% (w/w) solution in water, 45.6 mmoles) was added to a solution of 15 (162 mg, 296 μmoles) in methanol (4 mL). The reaction was stirred at room temperature for 5 h and then evaporated to dryness in vacuo. Purification by flash chromatrography (SiO$_2$; chloroform, then step-wise gradient from 20:1:0.1 to 20:2:0.1 chloroform/methanol/triethylamine) yielded the amine as a white solid (110 mg, 235 μmoles, 79%). LRMS: (ES+) calcd for C$_{29}$H$_{44}$N$_2$O$_3$ (M+H): 469. found: 469. $^1$H NMR: spectrum is consistent with the predicted structure.

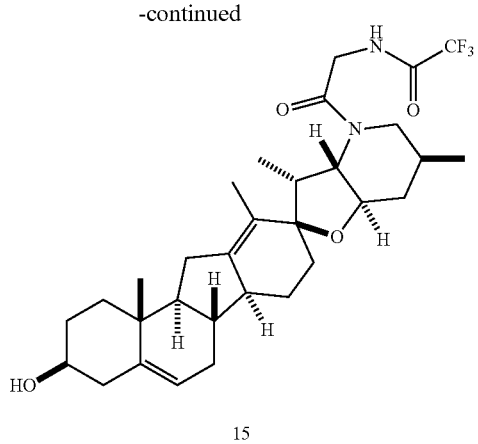

15

N—(N'-Trifluoroacetyl glycyl)cyclopamine (15)

Triethylamine (135 μL, 972 μmoles) and 14 (261 mg, 972 μmoles) were added to a solution of cyclopamine in dichloromethane (2.0 mL). The reaction was stirred at room temperature for 1 h and then subjected directly to purification by flash chromatrography (SiO$_2$, step-wise gradient from 8:1 to 2:1 hexane/acetone) yielded the amide as a white solid (166 mg, 294 μmoles, 60%). LRMS: (ES+) calcd for C$_{31}$H$_{43}$N$_2$O$_4$F$_3$ (M+H): 565. found: 565. $^1$H NMR: spectrum is consistent with the predicted structure.

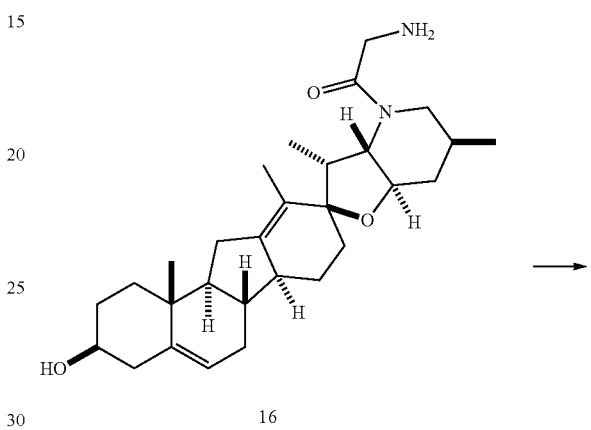

N-Aminoethyl cyclopamine (17)

Lithium aluminum hydride (939 μL of a 1 M solution in THF, 939 μmoles) was added to a suspension of 16 (110 mg, 235 μmoles) in THF (6 mL). The reaction was refluxed for 3 h and then quenched with water (5 mL) and aqueous KOH (10 mL of a 10% solution). After extracting the mixture with chloroform (2×20 mL), the organic layer was dried over Na$_2$SO$_4$, filtered, and concentrated in vacuo. Purification by flash chromatography (SiO$_2$, step-wise gradient from 20:1:0.1 to 20:2:0.1 chloroform/methanol/triethylamine) yielded the diamine as a colorless oil (94.4 mg, 208 μmoles, 88%). LRMS: (ES+) calcd for C$_{29}$H$_{46}$N$_2$O$_2$ (M+H): 455. found: 455. $^1$H NMR: spectrum is consistent with the predicted structure.

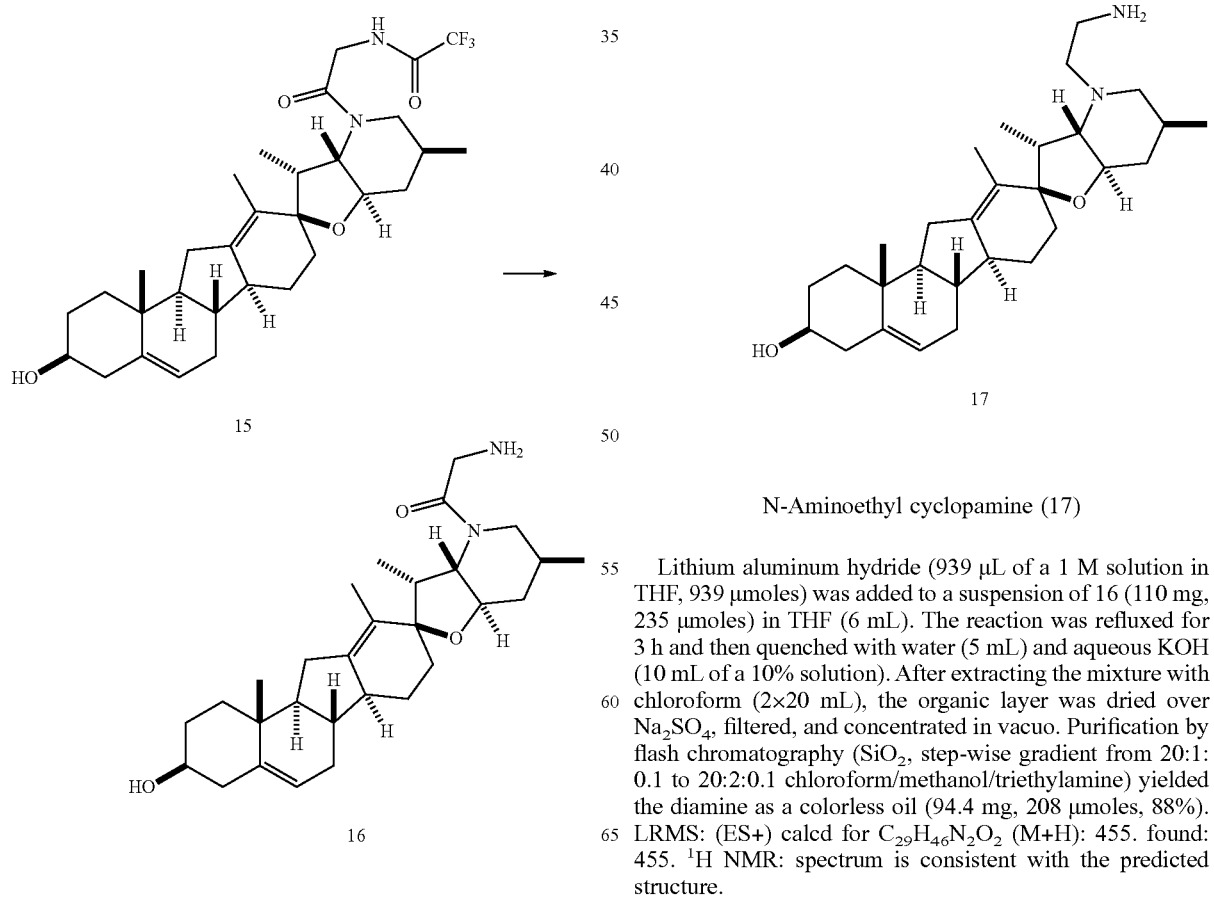

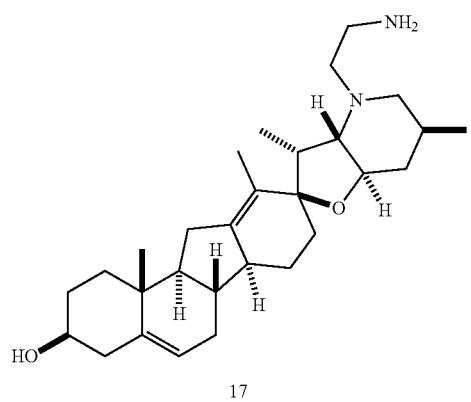

17

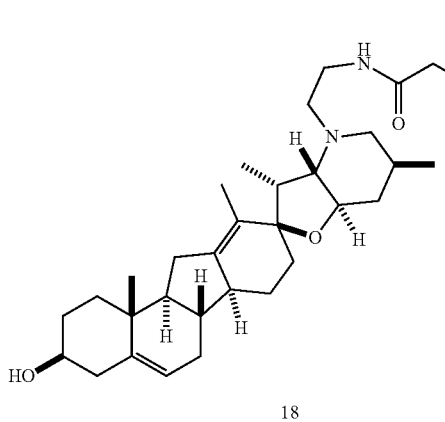

N—(N'-Dihydrocinnamoyl aminoethyl)cyclopamine (18)

Triethylamine (5.03 μL, 36.1 μmoles) and 4 (4.46 mg, 18.0 μmoles) were added to a solution of 17 (8.2 mg, 18.0 μmoles) in dichloromethane (500 μL). The reaction was stirred at room temperature for 3 h and then evaporated to dryness by a stream of nitrogen gas. Purification by flash chromatography (SiO$_2$, step-wise gradient from 4:1 to 1:1 hexane/acetone) yielded the amide as a white solid (5.7 mg, 9.71 μmoles, 54%). LRMS: (ES+) calcd for C$_{38}$H$_{54}$N$_2$O$_3$ (M+H): 587. found: 587. $^1$H NMR: spectrum is consistent with the predicted structure.

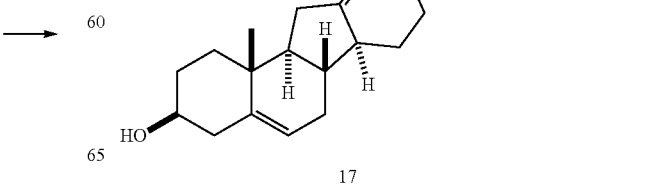

19

3-Keto, N—(N'-dihydrocinnamoyl aminoethyl)cyclopamine (19)

Dimethylsulfoxide (6.89 μL, 97.1 μmoles) was added to a solution of oxalyl chloride (4.24 μL, 48.6 μmoles) in dichloromethane (250 μL) at −78° C. After the mixture was stirred at −78° C. for 10 min, a solution of 18 (5.7 mg, 9.71 μmoles) in dichloromethane (250 μL) was added, and the reaction was stirred at −78° C. for another 30 min. The oxidation was completed by the addition of triethylamine (20.3 μL, 146 μmoles) to the solution, which was stirred at −78° C. for 10 min and then allowed to warm to room temperature. The reaction was quenched by the addition of water (1 mL) and chloroform (5 mL), and the organic layer was isolated, washed with brine (1×2 mL), dried over over Na$_2$SO$_4$, and concentrated in vacuo. Purification by flash chromatography (SiO$_2$, step-wise gradient from 8:1 to 4:1 hexane/acetone) to yielded the ketone as a white solid (2.0 mg, 3.42 μmoles, 35%). Recovered starting material (1.6 mg, 2.73 μmoles, 28%). LRMS: (ES+) calcd for C$_{38}$H$_{52}$N$_2$O$_3$ (M+H): 585. found: 585. $^1$H NMR: spectrum is consistent with the predicted structure.

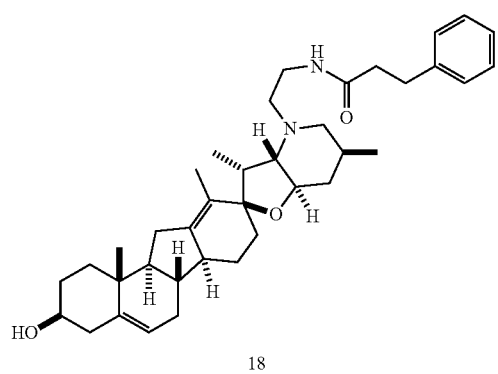

18
17

-continued

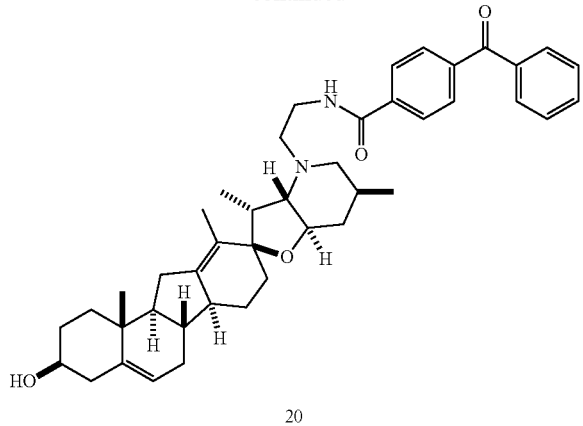

20

N—(N'-(4-Benzoylbenzoyl)aminoethyl)benzophenone (20)

4-Benzoylbenzoic acid N-hydroxysuccinimide ester (8.01 mg, 23.5 µmoles) and triethylamine (6.55 µL, 47.0 µmoles) were added to a solution of 17 (10.7 mg, 23.5 µmoles) in dichloromethane (500 µL). The reaction was stirred at room temperature for 2 h and then evaporated to dryness by a stream of nitrogen gas. Purification by flash chromatography ($SiO_2$, step-wise gradient from 100:1 to 50:1 chloroform/methanol) yielded the benzophenone as a colorless oil (10.8 mg, 16.3 µmoles, 69%). LRMS: (ES+) calcd for $C_{43}H_{54}N_2O_4$ (M+H): 663. found: 663. $^1H$ NMR: spectrum is consistent with the predicted structure.

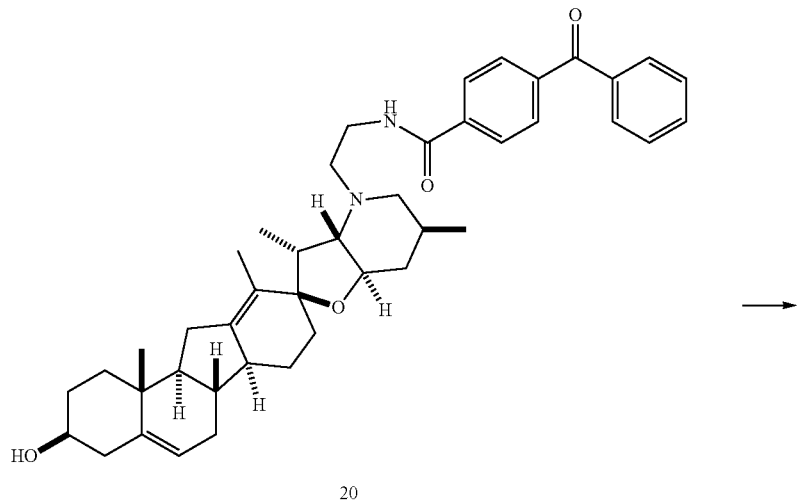

20

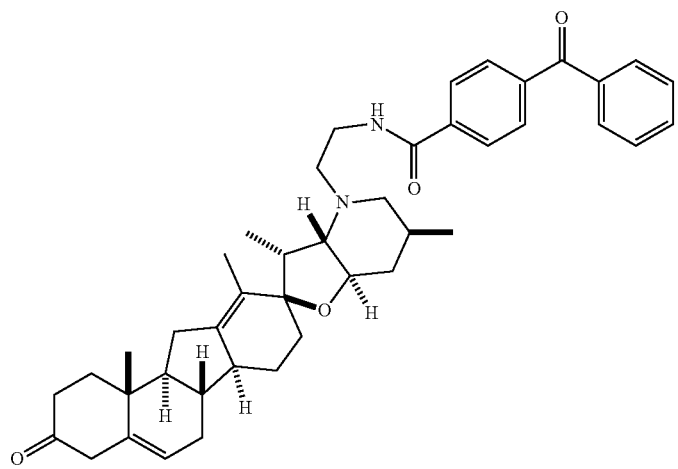

21

3-Keto, N—(N'-(4-benzoylbenzoyl) aminoethyl)cyclopamine (21)

Dimethylsulfoxide (11.6 µL, 163 µmoles) was added to a solution of oxalyl chloride (7.11 µL, 81.5 µmoles) in dichloromethane (250 µL) at −78° C. After the mixture was stirred at −78° C. for 10 min, a solution of 20 (10.8 mg, 16.3 µmoles) in dichloromethane (250 µL) was added, and the reaction was stirred at −78° C. for another 30 min. The oxidation was completed by the addition of triethylamine (34.1 µL, 245 µmoles) to the solution, which was stirred at −78° C. for 10 min and then allowed to warm to room temperature. The reaction was quenched by the addition of water (1 mL) and chloroform (5 mL). The resultant organic layer was then washed with brine (1×2 mL), dried over over $Na_2SO_4$, and concentrated in vacuo. Purification by flash chromatography ($SiO_2$, step-wise gradient from 8:1 to 2:1 hexane/acetone) yielded the ketone as a white solid (6.3 mg, 9.53 µmoles, 58%). LRMS: (ES+) calcd for $C_{43}H_{52}N_2O_4$ (M+H): 661. found: 661. $^1$H NMR: spectrum is consistent with the predicted structure.

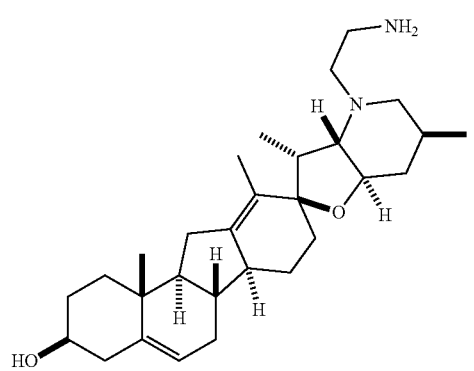

17

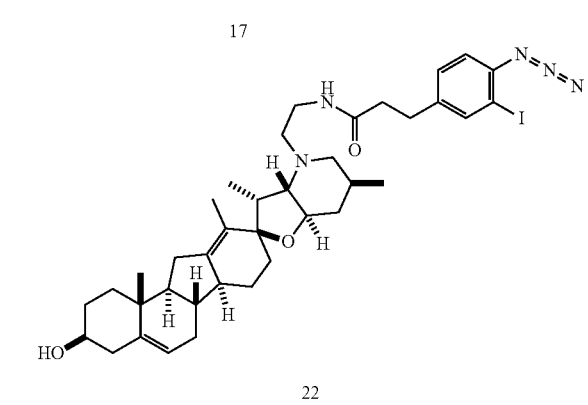

22

N—(N'-Azidoiodophenylpropionyl aminoethyl)cyclopamine (22)

Azidoiodophenylpropionyl N-hydroxysuccinimide ester (1.9 mg, 4.18 µmoles) and triethylamine (2.34 µL, 16.7 µmoles) were added to a solution of 17 (1.9 mg, 4.18 µmoles) in dichloromethane (500 µL). The reaction was stirred at room temperature for 3 h and then evaporated to dryness by a stream of nitrogen gas. Purification by flash chromatography ($SiO_2$, step-wise gradient from 4:1 to 1:1 hexane/acetone) yielded the benzophenone as a white solid (1.6 mg, 2.12 µmoles, 51%). LRMS: (ES+) calcd for $C_{38}H_{52}N_5O_3I$ (M+H): 754. found: 754. $^1$H NMR: spectrum is consistent with the predicted structure.

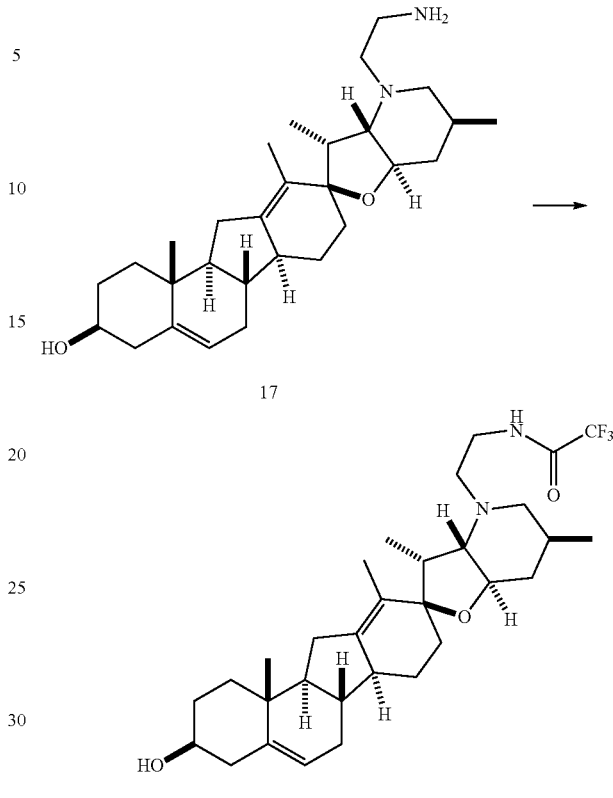

17

23

N—(N'-Trifluoroacetyl aminoethyl)cyclopamine (23)

Trifluoroacetic anhydride (20.6 µL, 146 µmoles) and triethylamine (24.5 µL, 176 µmoles) were added to a solution of 17 (13.3 mg, 29.3 µmoles) in dichloromethane (0.5 mL). The mixture was stirred for 30 min at room temperature and then evaporated to dryness by a stream of nitrogen gas. The resultant residue was redissolved in methanol (1 mL) and the solution was stirred at room temperature for 1 h. After removal of the solvent in vacuo, purification by flash chromatography ($SiO_2$, step-wise gradient from 4:1 to 2:1 hexane:acetone) yielded the amide as a white solid (9.2 mg, 16.7 µmoles, 57%). LRMS: not performed. $^1$H NMR: spectrum is consistent with the predicted structure.

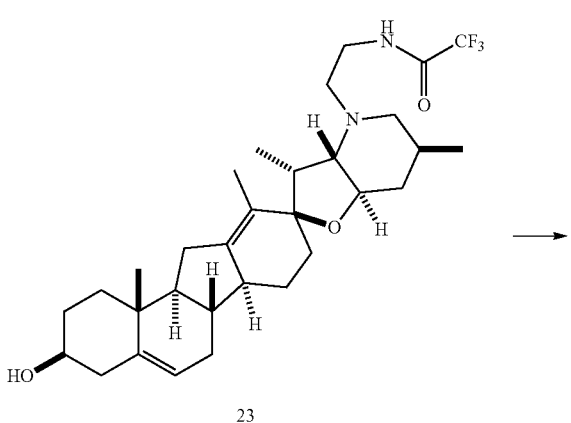

23

-continued

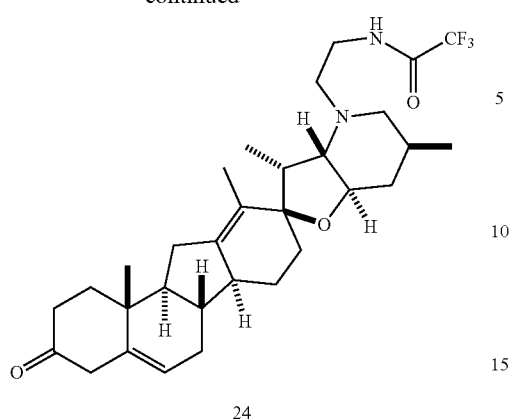

24

3-Keto, N—(N'-trifluoroacetyl aminoethyl)cyclopamine (24)

Dimethylsulfoxide (11.9 µL, 167 µmoles) was added to a solution of oxalyl chloride (7.28 µL, 83.5 µmoles) in dichloromethane (250 µL) at −78° C. After the mixture was stirred at −78° C. for 10 min, a solution of 23 (9.2 mg, 16.7 µmoles) in dichloromethane (250 µL) was added, and the reaction was stirred at −78° C. for another 30 min. The oxidation was completed by the addition of triethylamine (35.0 µL, 251 µmoles) to the solution, which was stirred at −78° C. for 10 min and then allowed to warm to room temperature. The reaction was quenched by the addition of saturated aqueous NaHCO$_3$ (2 mL) and chloroform (5 mL), and the organic layer was isolated, dried over Na$_2$SO$_4$, and concentrated in vacuo. Purification by flash chromatography (SiO$_2$, step-wise gradient from 8:1 to 4:1 hexane/acetone) yielded the ketone as a white solid (6.0 mg, 10.9 µmoles, 65%). LRMS: not performed. $^1$H NMR: spectrum is consistent with the predicted structure.

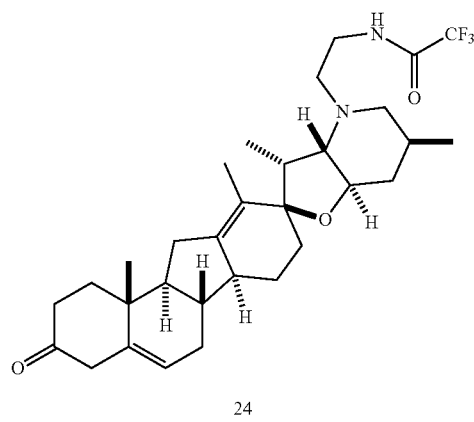

24

-continued

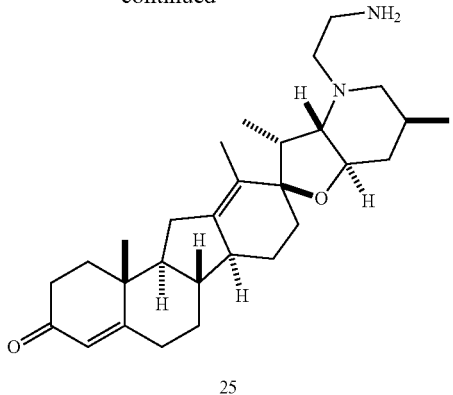

25

3-Enone, N-aminoethyl cyclopamine (25)

Aqueous ammonia (250 µL of a 29% (w/w) solution in water, 3.80 mmoles) was added to a solution of 24 (3.0 mg, 5.47 µmoles) in methanol (250 µL). The reaction was stirred at room temperature for 24 h and then evaporated to dryness by a stream of nitrogen gas. Purification by flash chromatography (SiO$_2$, step-wise gradient from 20:1:0.1 to 20:2:0.1 chloroform/methanol/triethylamine) yielded the amine as a colorless oil (3.0 mg, 6.63 µmoles, quant.). LRMS: not performed. $^1$H NMR: spectrum is consistent with the predicted structure.

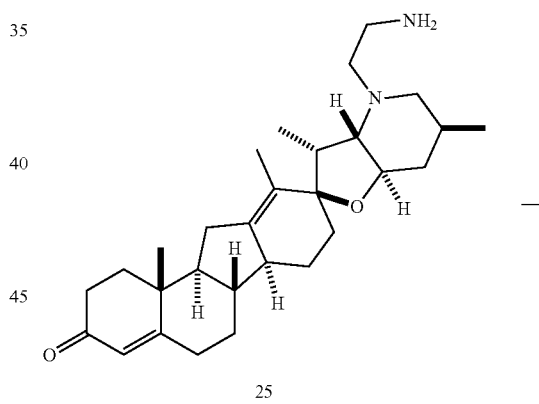

25

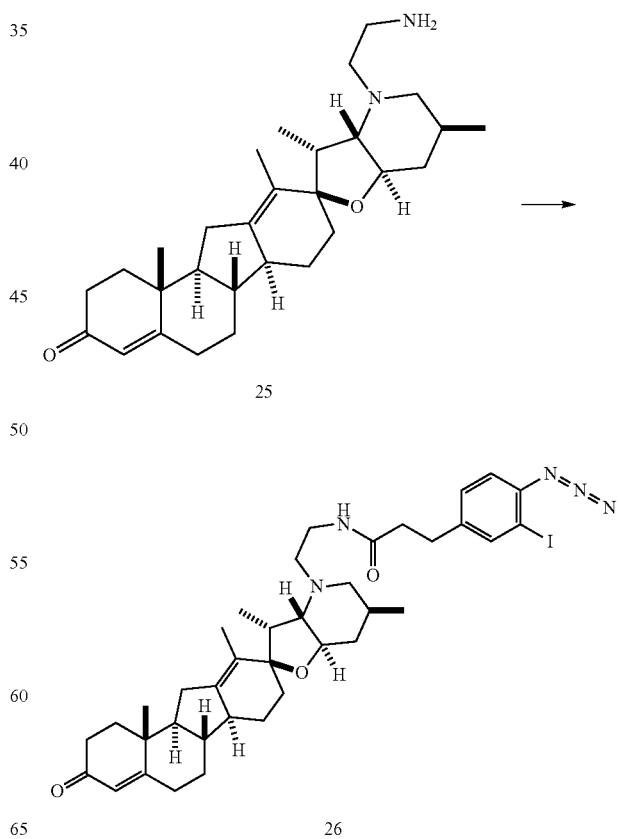

26

3-Enone, N—(N'-azidoiodophenylpropionyl aminoethyl)cyclopamine (26)

Azidoiodophenylpropionyl N-hydroxysuccinimide ester (1.4 mg, 3.31 µmoles) and triethylamine (1.8 µL, 13.2 µmoles) were added to a solution of 25 (1.5 mg, 3.31 µmoles) in dichloromethane (250 µL). The reaction was stirred at room temperature for 3 h and then quenched with dimethylaminopropylamine. Purification by flash chromatography (SiO$_2$, step-wise gradient from 8:1 to 2:1 hexane/acetone) to yield the aryl azide as a white solid (0.5 mg, 0.665 µmoles, 20%). LRMS: (ES+) calcd for C$_{38}$H$_{50}$N$_5$O$_3$I (M+H): 752. found: 752. $^1$H NMR: spectrum is consistent with the predicted structure.

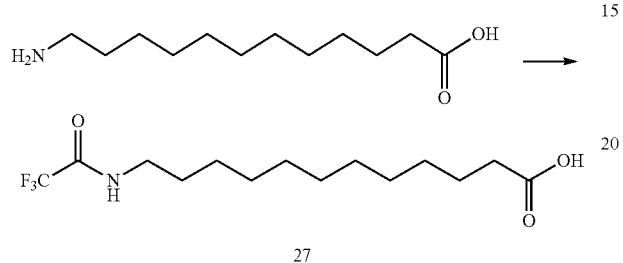

N-Trifluoroacetyl 12-aminododecanoic acid (27)

Methyl trifluoroacetate (200 µL, 1.99 mmoles) and triethylamine (184 µL, 1.32 mmoles) were added to a suspension of 12-aminododecanoic acid (300 mg, 1.32 mmoles) in methanol (2 mL). After the mixture was stirred vigorously for 18 h, 1 N HCl was added dropwise until the a pH of 2 was obtained. The reaction was added to ethyl acetate (20 mL) was washed with 1 N HCl (2×5 mL), dried over MgSO$_4$, and concentrated in vacuo to yield the amide as a white solid (398 mg, 1.28 mmoles, 97%). LRMS: not performed. $^1$H NMR: spectrum is consistent with the predicted structure.

N-Trifluoroacetyl 12-aminododecanoic acid N-hydroxysuccinimide ester (28)

Disuccinimidyl carbonate (247 mg, 964 µmoles) was added to a solution of 27 (200 mg, 642 µmoles) and pyridine (104 µL, 1.28 mmoles) in acetonitrile (2.0 mL). The reaction mixture was stirred at room temperature for 4.5 h, during which the solution became clear and evolved gas. The solution was added to ethyl acetate (10 mL), washed with 1 N HCl (2×1 mL) and saturated aqueous NaHCO$_3$ (2×1 mL), dried over MgSO$_4$, and concentrated in vacuo to yield a white solid (257 mg, 629 µmoles, 98%). LRMS: not performed. $^1$H NMR: spectrum is consistent with the predicted structure.

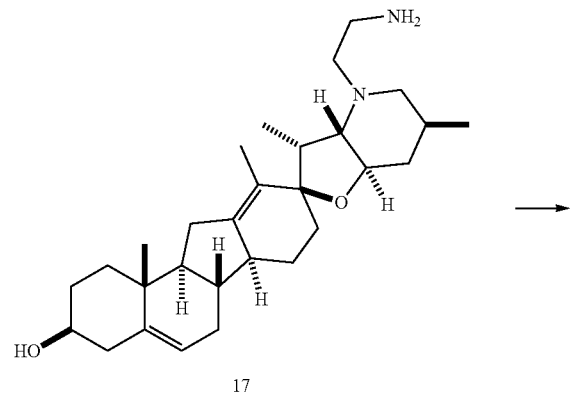

N—(N'—(N"-Trifluoroacetyl aminododecanoyl) aminoethyl)cyclopamine (29)

Triethylamine (4.78 μL, 34.3 μmoles) and 28 (8.4 mg, 20.6 μmoles) were added to a solution of 17 (7.8 mg, 17.2 μmoles) in dichloromethane (250 μL). The reaction was stirred at room temperature for 12 h and then evaporated to dryness by a stream of nitrogen gas. Purification by flash chromatography (SiO$_2$, step-wise gradient from 100:1 to 25:1 chloroform/methanol) yielded the amide as a white solid (8.0 mg, 10.7 μmoles, 62%). LRMS: (ES+) calcd for C$_{43}$H$_{68}$N$_3$O$_4$ (M+H): 748. found: 748. $^1$H NMR: spectrum is consistent with the predicted structure.

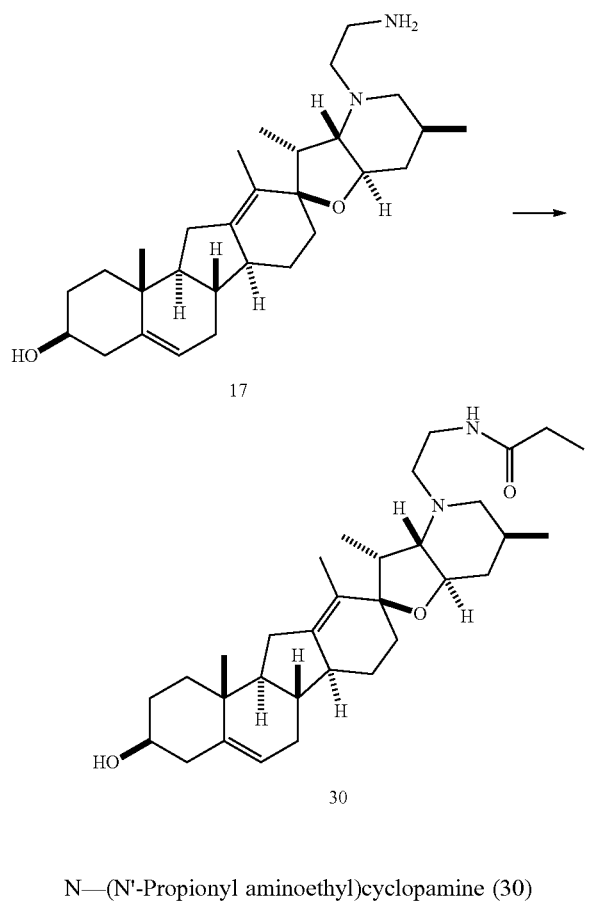

N—(N'-Propionyl aminoethyl)cyclopamine (30)

Propionyl N-hydroxysuccinimide ester (1.08 mg, 6.33 μmoles) and triethylamine (1.48 μL, 10.6 μmoles) were added to a solution of 17 (2.4 mg, 5.28 μmoles) in dichloromethane (250 μL). The reaction was stirred at room temperature for 12 h and then quenched with dimethylaminopropylamine. Purification by flash chromatography (SiO$_2$, step-wise gradient from 100:1 to 25:1 chloroform/methanol) yielded the amide as a colorless oil (1.8 mg, 3.52 μmoles, 67%). LRMS: (ES+) calcd for C$_{32}$H$_{50}$N$_2$O$_3$ (M+H): 511. found: 511. $^1$H NMR: spectrum is consistent with the predicted structure.

Preparation of $^3$H-labeled 30.

Propionyl N-hydroxysuccinimide ester (1 mCi, specific activity=100 Ci/mmol, 10 nmoles) in ethyl acetate (1.0 mL) was mixed with 17 (1.1 mg, 2.5 μmoles) in chloroform (100 μL). The reaction mixture was incubated without stirring for 20 h at room temperature. Purification by flash chromatography (SiO$_2$, step-wise gradient from 100:1 to 25:1 chloroform/methanol) yielded the tritium-labeled cyclopamine derivative. Fractions containing the desired product were pooled and concentrated with a stream of nitrogen gas. The concentration solution was resuspended in methanol (200 μL) and stored at –20° C. Beta/scintillation counter analysis determined the reaction yield to be approximately 81%, and thin layer chromatography analysis (Rf=0.80; 10:2:0.1 dichloromethane/methanol/triethylamine) is consistent with known properties of cold 30.

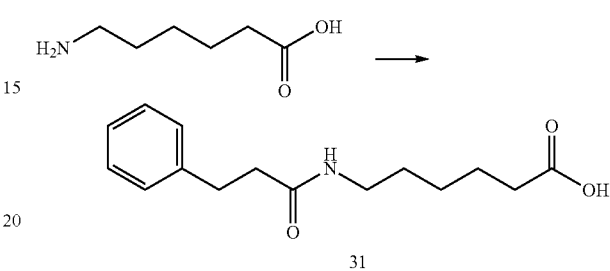

N-Dihydrocinnamoyl aminocaproic acid (31)

Aminocaproic acid (100 mg, 747 μmoles) and 4 (185 mg, 747 μmoles) were dissolved in DMF/water (1 mL; 1:1). The reaction was stirred at room temperature for 1 h, and then acidified with 1 N HCl until a pH of 2 was obtained. The mixture was added to ethyl acetate (10 mL), washed with 1 N HCl (2×5 mL), dried over MgSO4, and concentrated in vacuo to yield a white waxy solid (175 mg, 665 μmoles, 89%). LRMS: not performed. $^1$H NMR: spectrum is consistent with the predicted structure.

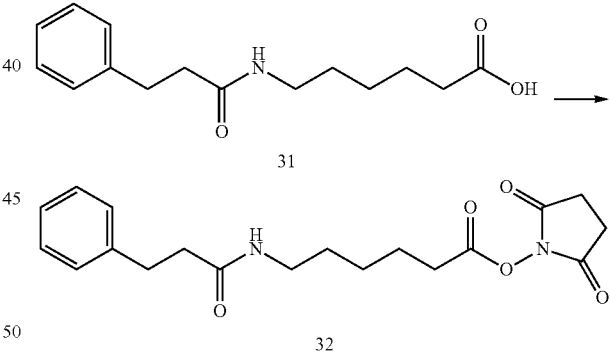

N-Dihydrocinnamoyl aminocaproic acid N-hydroxysuccinimide ester (32)

Disuccinimidyl carbonate (155 mg, 604 μmoles) was added to a solution of 31 (159 mg, 604 μmoles) and pyridine (97.7 μL, 1.21 mmoles) in acetonitrile (1 mL). The reaction mixture was stirred at room temperature for 2.5 h, during which the solution became clear and evolved gas. The solution was added to ethyl acetate (5 mL), washed with 1 N HCl (2×1 mL) and saturated aqueous NaHCO$_3$ (2×1 mL), dried over MgSO$_4$, and concentrated in vacuo to yield a colorless oil (156 mg, 433 μmoles, 72%). LRMS: not performed. $^1$H NMR: spectrum is consistent with the predicted structure.

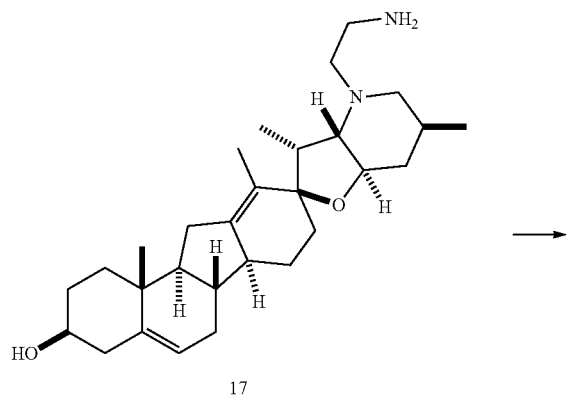

17

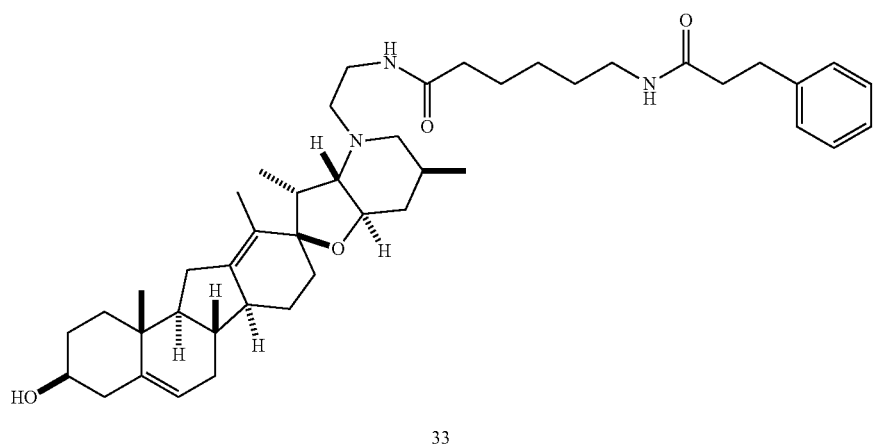

33

N—(N′—(N″-Dihydrocinnamoyl aminocaproyl)aminoethyl)cyclopamine (33)

Triethylamine (4.43 μL, 31.8 μmoles) and 32 (5.75 mg, 15.9 μmoles) were added a solution of 17 (7.25 mg, 15.9 μmoles) in dichloromethane (250 μL). The reaction was stirred at room temperature for 1 h and evaporated to dryness by a stream of nitrogen gas. Purification by flash chromatography (SiO$_2$, step-wise gradient from 100:1 to 25:1 chloroform/methanol) yielded the amide as a colorless oil (5.8 mg, 8.29 μmoles, 52%). LRMS: (ES+) calcd for C$_{44}$H$_{65}$N$_3$O$_4$ (M+H): 700. found: 700. $^1$H NMR: spectrum is consistent with the predicted structure.

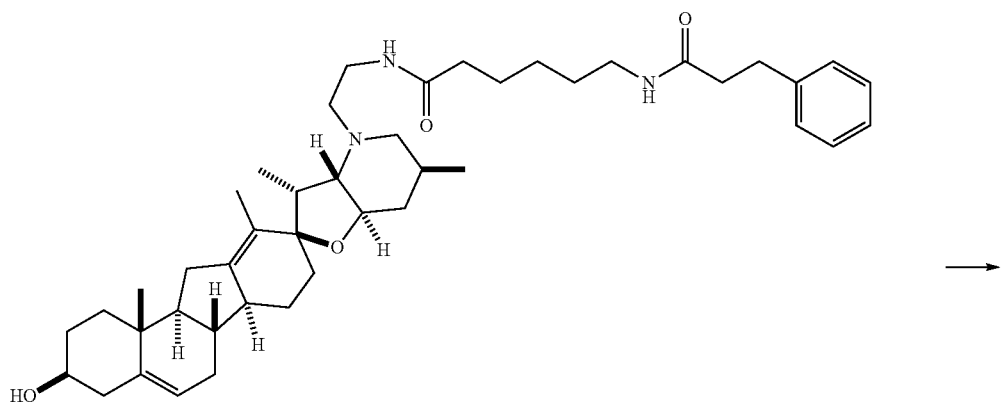

33

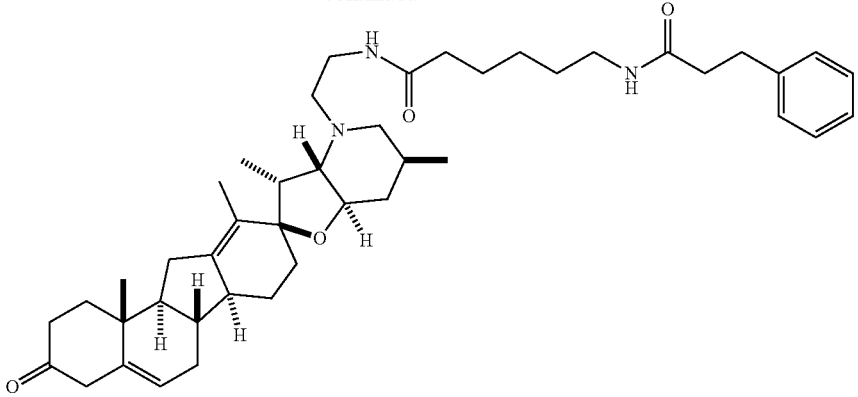

34

3-Keto, N—(N'—(N''-dihydrocinnamoyl aminocaproyl)aminoethyl)cyclopamine (34)

Dimethylsulfoxide (12.7 µL, 177 µmoles) was added to a solution of oxalyl chloride (7.73 µL, 88.6 µmoles) in dichloromethane (250 µL) at −78° C. After the mixture was stirred at −78° C. for 10 min, a solution of 33 (6.2 mg, 8.86 µmoles) in dichloromethane (250 µL) was added, and the reaction was stirred at −78° C. for another 30 min. The oxidation was completed by the addition of triethylamine (37.1 µL, 266 µmoles) to the solution, which was stirred at −78° C. for 10 min and then allowed to warm to room temperature. The reaction was quenched by the addition of saturated aqueous $NaHCO_3$ (2 mL) and extracted with chloroform (2×2 mL). The resultant organic layer was then isolated, dried over over $Na_2SO_4$, and concentrated in vacuo. Purification by flash chromatography ($SiO_2$, step-wise gradient from 100:1 to 25:1 chloroform/methanol) to yielded the ketone as a slightly yellow oil (5.4 mg, 7.74 µmoles, 87%). LRMS: (ES+) calcd for $C_{44}H_{63}N_3O_4$ (M+H): 698. found: 698. $^1$H NMR: spectrum is consistent with the predicted structure.

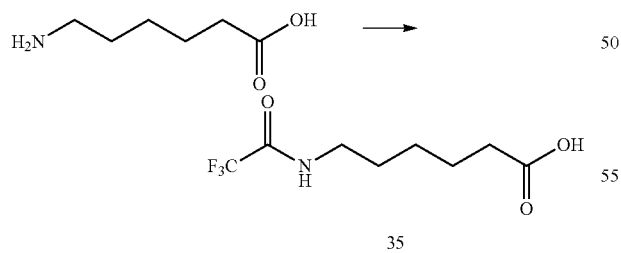

35

N-Trifluoroacetyl aminocaproic acid (35)

Methyl trifluoroacetate (513 µL, 5.10 mmoles) and triethylamine (474 µL, 3.40 mmoles) were added to a suspension of aminocaproic acid (455 mg, 3.40 mmoles) in methanol (2 mL). After the mixture was stirred vigorously for 8 h, 1 N HCl was added dropwise until the a pH of 2 was obtained. The reaction was added to ethyl acetate (10 mL) was washed with 1 N HCl (2×2 mL), dried over $MgSO_4$, and concentrated in vacuo to yield the amide as a white solid (745 mg, 3.49 mmoles, quant.). LRMS: not performed. $^1$H NMR: spectrum is consistent with the predicted structure.

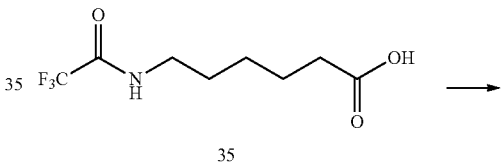

35

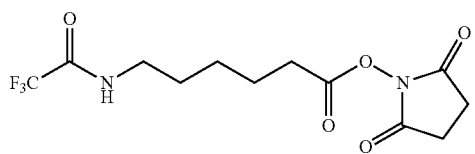

36

N-Trifluoroacetyl aminocaproic acid N-hydroxysuccinimide ester (36)

Disuccinimidyl carbonate (541 mg, 2.11 mmoles) was added to a solution of 35 (300 mg, 1.41 mmoles) and pyridine (227 µL, 2.81 mmoles) in acetonitrile (2.0 mL). The reaction mixture was stirred at room temperature for 13 h, during which the solution became clear and evolved gas. The solution was added to ethyl acetate (10 mL), washed with 1 N HCl (2×1 mL) and saturated aqueous $NaHCO_3$ (2×1 mL), dried over $MgSO_4$, and concentrated in vacuo to yield a white solid (471 mg, 1.45 mmoles, quant.). LRMS: not performed. $^1$H NMR: spectrum is consistent with the predicted structure.

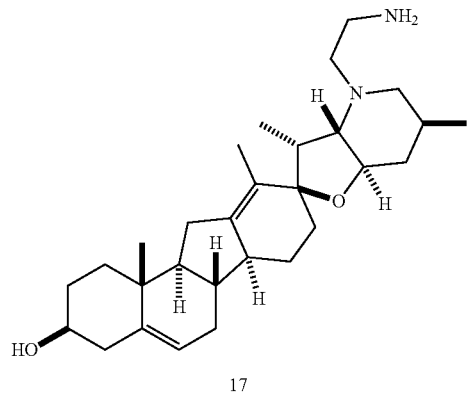

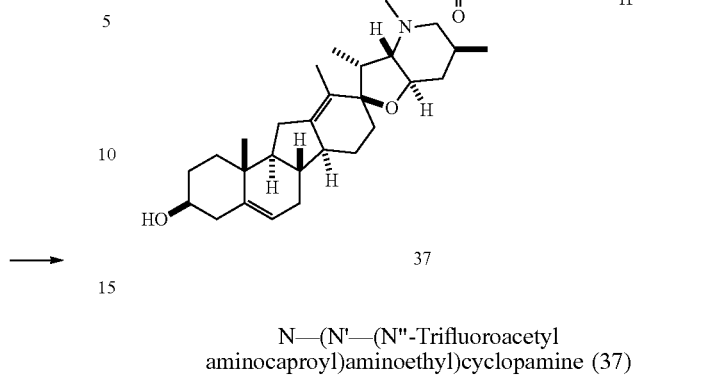

N—(N'—(N''-Trifluoroacetyl aminocaproyl)aminoethyl)cyclopamine (37)

Triethylamine (12.3 µL, 88.0 µmoles) and 36 (17.1 mg, 52.8 µmoles) were added to a solution of 17 (20.0 mg, 44.0 µmoles) in dichloromethane (200 µL). The reaction mixture was stirred at room temperature for 13 h, quenched with dimethylaminopropylamine (11.2 µL, 88.0 µmoles), and evaporated to dryness with a stream of nitrogen gas. Purification by flash chromatography (SiO$_2$, step-wise gradient from 50:1 to 25:1 chloroform/methanol) yielded the amide as a colorless oil (26.9 mg, 40.5 µmoles, 92%). LRMS: not performed. $^1$H NMR: spectrum is consistent with the predicted structure.

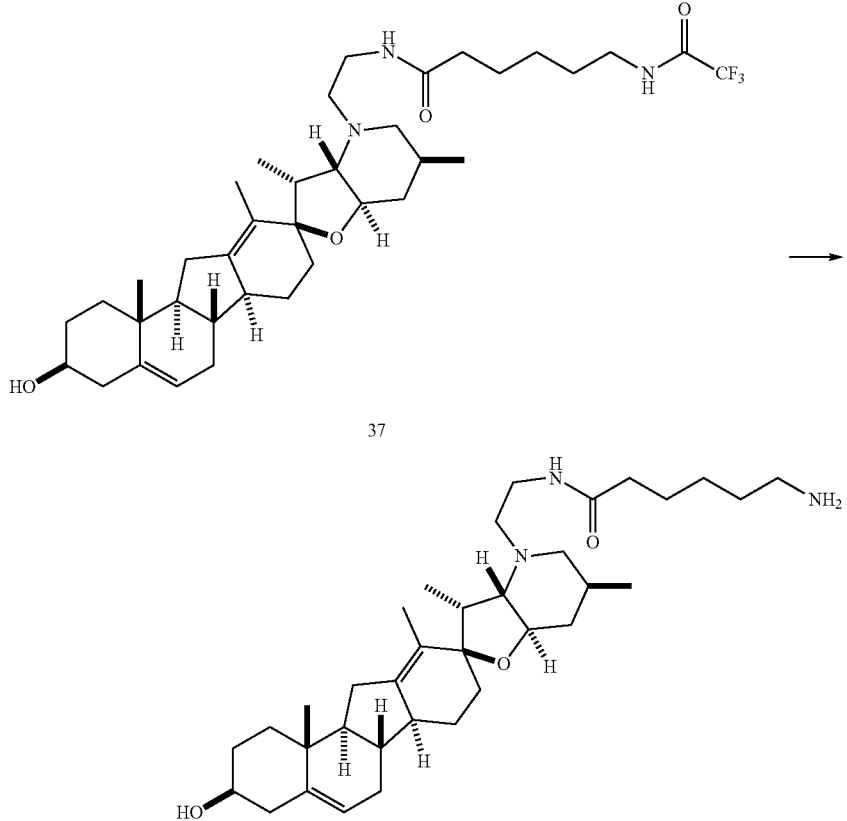

N—(N'-Aminocaproyl aminoethyl)cyclopamine (38)

Aqueous ammonia (200 µL of a 29% (w/w) solution in water, 3.04 mmoles) was added to a solution of 37 (26.9 mg, 40.5 µmoles) in methanol (400 µL). The reaction was stirred at room temperature for 20 h and then evaporated to dryness by a stream of nitrogen gas. Purification by flash chromatography (SiO$_2$, step-wise gradient from 20:1:0.1 to 20:4:0.1 chloroform/methanol/triethylamine) yielded the amine as a white waxy solid (19.3 mg, 34.0 µmoles, 84%.). LRMS: not performed. $^1$H NMR: spectrum is consistent with the predicted structure.

calcd for $C_{44}H_{63}N_6O_4I$ (M+H): 867. found: 867. $^1$H NMR: spectrum is consistent with the predicted structure.

Preparation of $^{125}$I-labeled 39.

$^{125}$I-labeled azidoiodophenylpropionyl N-hydroxysuccinimide ester (0.250 mCi, specific activity=2200 Ci/mmol, 0.114 nmoles) in ethyl acetate (2.1 mL) was concentrated to a volume of approximately 10 µL by a stream of nitrogen gas. The concentrated solution was diluted with ethyl acetate (100 µL) and was mixed with 38 (1.0 mg, 1.76 µmoles) in chloroform (100 µL). The reaction was mixture was incubated without stirring for 43 h at room temperature and then concentrated to approximately 10 µL by a stream of nitrogen gas. The residue was resuspended in chloroform (200 µL)

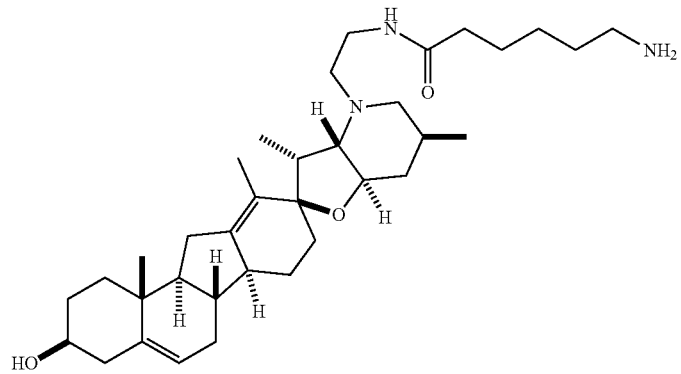

38

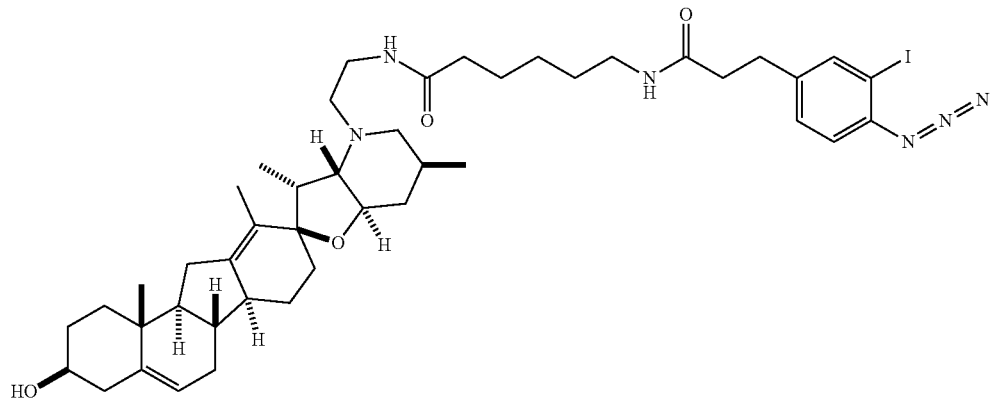

39

N—(N'—(N''-Azidoiodophenylpropionyl aminocaproyl)aminoethyl)cyclopamine (39)

Azidoiodophenylpropionyl N-hydroxysuccinimide ester (1.4 mg, 3.38 µmoles) and triethylamine (0.94 µL, 6.76 µmoles) were added to a solution of 38 (1.92 mg, 3.38 µmoles) in dichloromethane (250 µL). The reaction was stirred at room temperature for 2.5 h and evaporated to dryness by a stream of nitrogen gas. Purification by flash chromatography (SiO$_2$, step-wise gradient from 4:1:0.025 to 1:2:0.015 hexane/acetone/triethylamine) yielded the azide as a colorless oil (2.2 mg, 2.54 µmoles, 75%). LRMS: (ES+)

and purified by flash chromatography (SiO$_2$, step-wise gradient from 100:1 to 12.5:1 chloroform/methanol) to yield the radiolabeled azide. Fractions containing the desired product were pooled, concentrated by a stream of nitrogen gas, resuspended in methanol (1 mL), and a small aliquot removed for quantitation. Gamma counter analysis determined the reaction yield to be essentially quantitative, and the solution was reconcentrated by a stream of nitrogen gas, resuspended in methanol (250 µL), and stored at −20° C. Thin layer chromatography analysis (Rf=0.62; 10:2:0.1 dichloromethane/methanol/triethylamine) is consistent with known properties of cold 39.

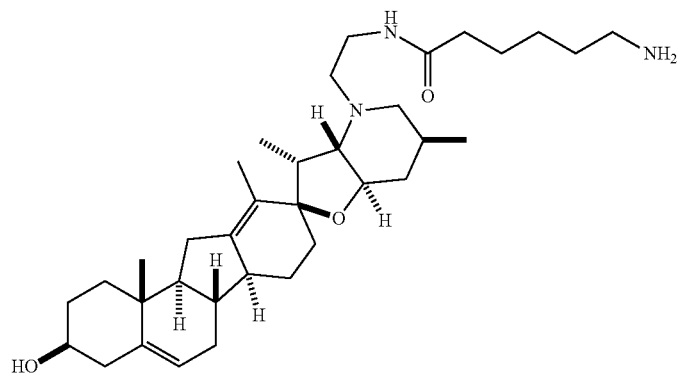

38

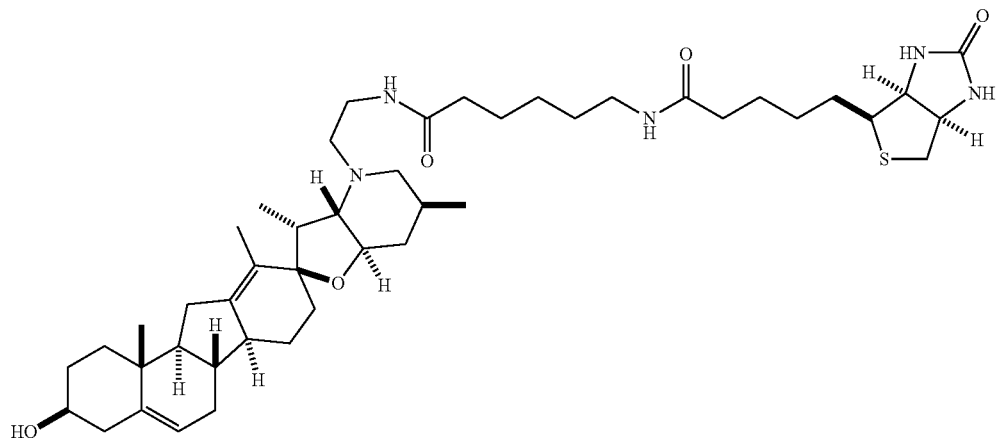

40

N—(N'—(N''-Biotinoyl aminocaproyl)aminoethyl)cyclopamine (40)

Biotinoyl N-hydroxysuccinimide ester (6.72 mg, 14.8 µmoles) and triethylamine (3.43 µL, 24.6 µmoles) were added to a solution of 38 (5.6 mg, 12.3 µmoles) in DMF (250 µL). The reaction was stirred at room temperature for 14 h and then added to chloroform (2 mL). The organic mixture was washed with saturated aqueous $NaHCO_3$ (3×1 mL), dried over $Na_2SO_4$, and concentrated in vacuo. Purification by flash chromatography ($SiO_2$, step-wise gradient from 20:1:0.05 to 20:5:0.05 chloroform/methanol/triethylamine) yielded the ketone as a white solid (9.4 mg, 12.5 µmoles, quant.). LRMS: (ES+) calcd for $C_{45}H_{71}N_5O_5S$ (M+H): 794. found: 794. $^1H$ NMR: spectrum is consistent with the predicted structure.

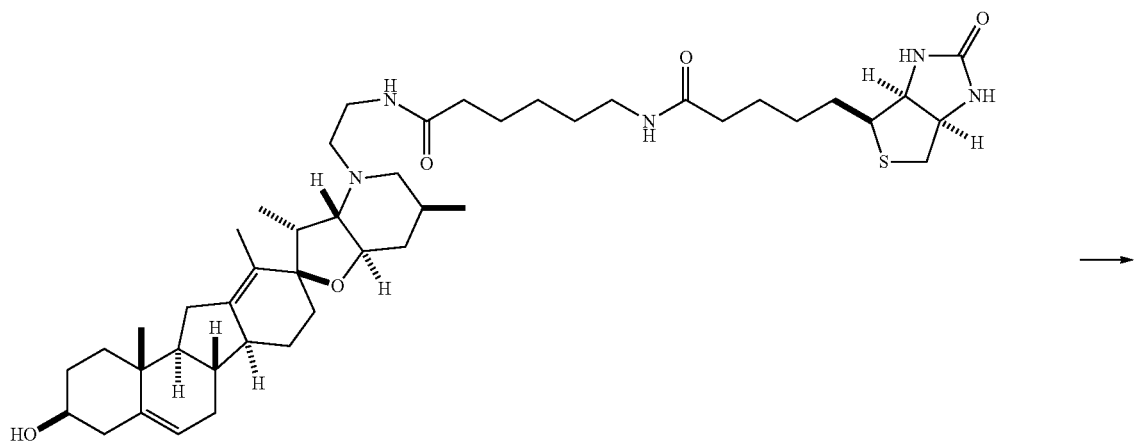

40

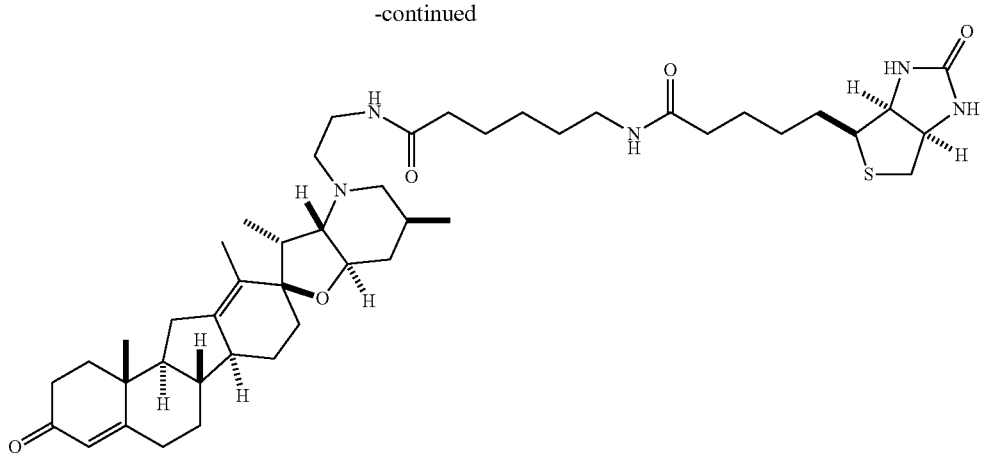

41

3-Enone, N—(N'—(N''-Biotinoyl aminocaproyl)aminoethyl)cyclopamine (41)

Dimethylsulfoxide (3.66 μL, 51.6 μmoles) was added to a solution of oxalyl chloride (2.25 μL, 25.8 μmoles) in dichloromethane (250 μL) at −78° C. After the mixture was stirred at −78° C. for 10 min, a solution of 40 (4.1 mg, 5.16 μmoles) in dichloromethane (200 μL) was added, and the reaction was stirred at −78° C. for another 30 min. The oxidation was completed by the addition of triethylamine (10.8 μL, 77.4 μmoles) to the solution, which was stirred at −78° C. for 10 min and then allowed to warm to room temperature. The reaction was quenched by the addition of saturated aqueous NaHCO$_3$ (2 mL) and extracted with chloroform (2×2 mL). The resultant organic layer was then dried over over Na$_2$SO$_4$, and concentrated in vacuo. The residue was redissolved in MeOH (0.5 mL) and treated with aqueous ammonia (250 μL of a 29% (w/w) solution in water, 3.80 mmoles) for 20 h at room temperature. The reaction was added to chloroform (2 mL), washed with saturated aqueous NaHCO$_3$ (2×2 mL), dried over Na$_2$SO$_4$, and concentrated in vacuo. Purification by flash chromatography (SiO$_2$, stepwise gradient from 20:1:0.1 to 20:5:0.1 chloroform/methanol/triethylamine) to yielded the enone as a yellowish solid (1.4 mg, 1.77 μmoles, 34%). LRMS: (ES+) calcd for C$_{45}$H$_{69}$N$_5$O$_5$S (M+H): 792. found: 792. $^1$H NMR: spectrum is consistent with the predicted structure.

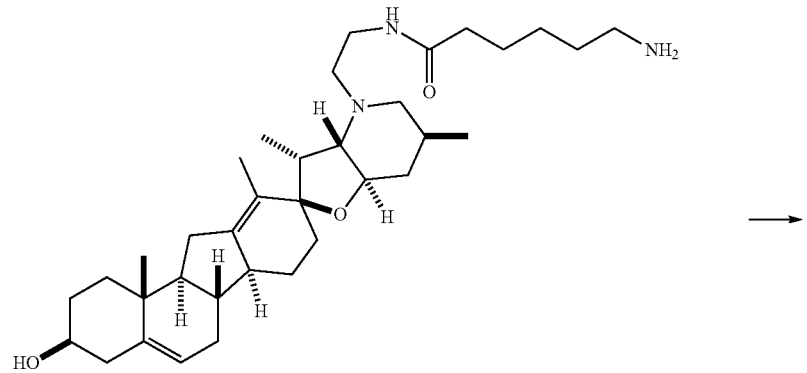

38

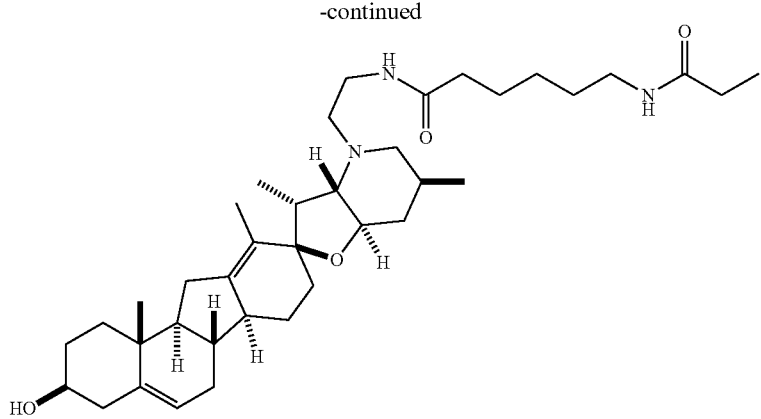

42

N—(N'—(N''-Propionyl aminocaproyl)aminoethyl)cyclopamine (42)

Propionyl N-hydroxysuccinimide ester (1.00 mg, 5.87 μmoles) and triethylamine (1.37 μL, 9.80 μmoles) were added to a solution of 38 (2.78 mg, 4.90 μmoles) in dichloromethane (250 μL). The reaction was stirred at room temperature for 12 h and then quenched with dimethylaminopropylamine. Purification by flash chromatography (SiO$_2$, step-wise gradient from 100:1 to 10:1 chloroform/methanol) yielded the amide as a colorless oil (2.5 mg, 4.01 μmoles, 82%). LRMS: (ES+) calcd for C$_{38}$H$_{61}$N$_3$O$_4$ (M+H): 624. found: 624. $^1$H NMR: spectrum is consistent with the predicted structure.

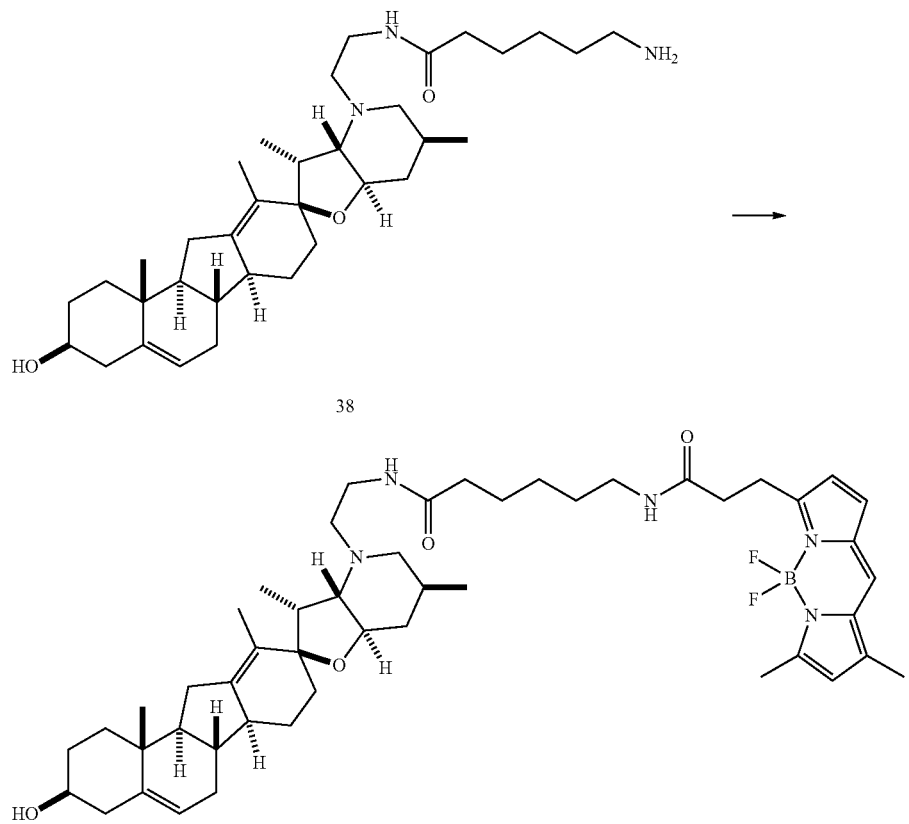

38

43

N—(N'—(N"-BODIPY FL aminocaproyl)aminoethyl)cyclopamine (43)

BODIPY FL N-hydroxysuccinimide ester (2.0 mg, 5.28 μmoles) and triethylamine (0.98 μL, 7.04 μmoles) were added to a solution of 38 (2.0 mg, 3.52 μmoles) in dichloromethane (500 μL). The reaction was stirred at room temperature for 20 h and then evaporated to dryness with a stream of nitrogen gas. Purification by flash chromatography (SiO$_2$, step-wise gradient from 50:1 to 12.5:1 chloroform/methanol) yielded the fluorophore as a colorless oil (2.6 mg, 3.09 μmoles, 88%). LRMS: (ES+) calcd for C$_{49}$H$_{70}$N$_5$O$_4$BF$_2$ (M+H): 842. found: 842. $^1$H NMR: spectrum is consistent with the predicted structure.

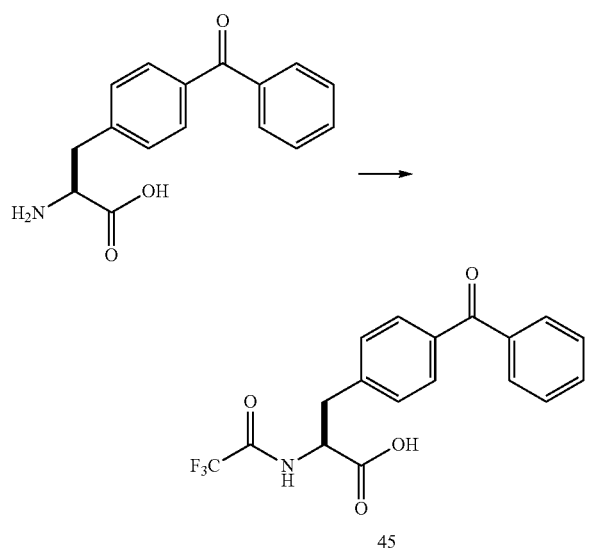

N-Trifluoroacetyl 4-benzoylphenylalanine (45)

Methyl trifluoroacetate (89.6 μL, 891 μmoles) and triethylamine (104 μL, 743 μmoles) were added to a suspension of 4-benzoylphenylalanine (200 mg, 743 μmoles) in methanol (0.5 mL). The reaction was stirred vigorously for 24 h and then acidified with 1 N HCl until a pH of 2 was obtained. The mixture was added to ethyl acetate (10 mL), washed with 1 N HCl (2×10 mL), dried over MgSO$_4$, and concentrated in vacuo to yield a white solid (49.7 mg, 136 μmoles, 18%). LRMS: not performed. $^1$H NMR: spectrum is consistent with the predicted structure.

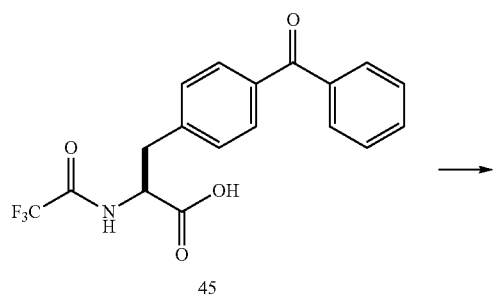

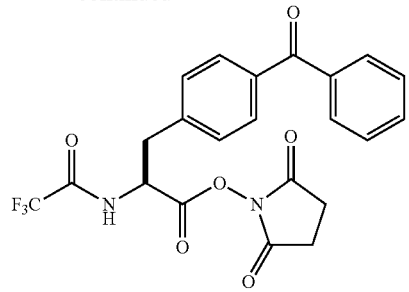

N-Trifluoroacetyl 4-benzoylphenylalanine N-hydroxysuccinimide ester (46)

Disuccinimidyl carbonate (33.0 mg, 129 μmoles) was added to a solution of 45 (47.1 mg, 129 μmoles) and pyridine (20.9 μL, 258 μmoles) in acetonitrile (0.5 mL). The reaction mixture was stirred at room temperature for 3 h, during which the solution became clear and evolved gas. The solution was added to ethyl acetate (5 mL), washed with 1 N HCl (2×1 mL) and saturated aqueous NaHCO$_3$ (2×1 mL), dried over MgSO$_4$, and concentrated in vacuo to yield a white solid (48.8 mg, 106 μmoles, 82%). LRMS: not performed. $^1$H NMR: spectrum is consistent with the predicted structure.

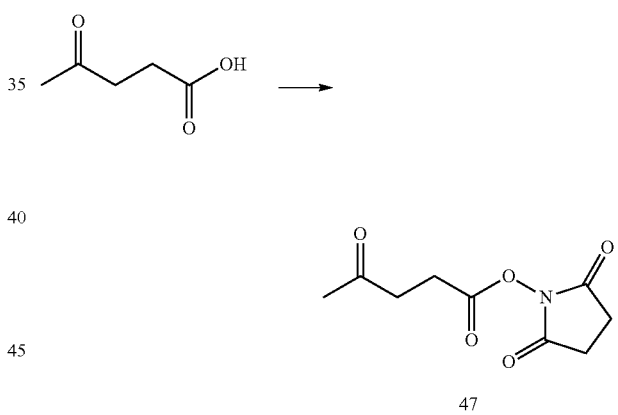

Levulinic Acid N-Hydroxysuccinimide Ester (47)

Disuccinimidyl carbonate (692 mg, 2.70 mmoles) and pyridine (437 μL, 2.70 mmoles) was added to a solution of levulinic acid (320 mg, 2.70 mmoles) in acetonitrile (2.0 mL). The reaction mixture was stirred at room temperature for 4.5 h, during which the solution became clear and evolved gas. The solution was added to ethyl acetate (10 mL), washed with 1N HCl (2×5 mL) and saturated aqueous NaHCO$_3$ (2×5 mL), dried over MgSO$_4$, and concentrated in vacuo to yield a white solid (333 mg, 1.56 mmoles, 58%). LRMS: not performed. $^1$H NMR: spectrum is consistent with the predicted structure.

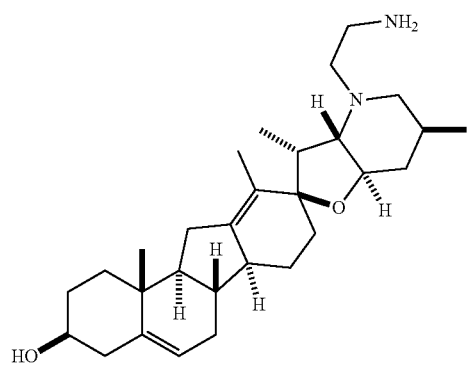

17

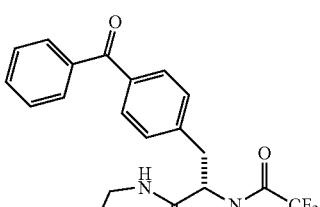

48

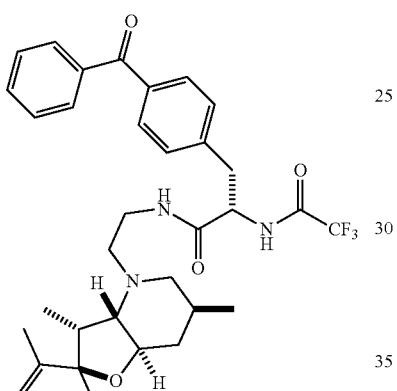

48

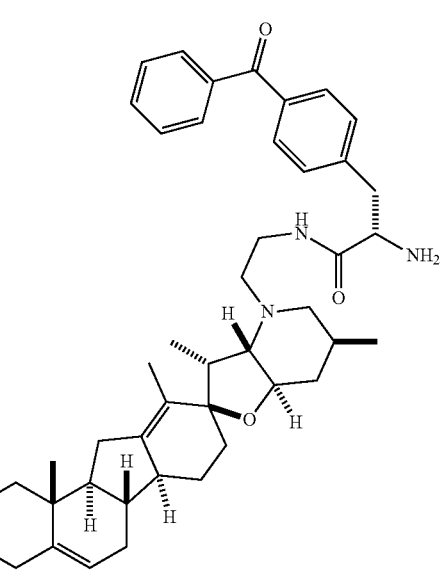

49

N—(N'—(N''-Trifluoroacetyl 4-benzoylphenylalanine) aminoethyl)cyclopamine (48)

Triethylamine (12.6 µL, 90.6 µmoles) and 46 (20.9 mg, 45.3 µmoles) were added to a solution of 17 (20.6 mg, 45.3 µmoles) in dichloromethane (0.5 mL). The reaction was stirred at room temperature for 1 h and then evaporated to dryness by a stream of nitrogen gas. Purification by flash chromatography (SiO$_2$, step-wise gradient from 8:1 to 1:1 hexane/acetone) yielded the benzephenone as a white solid (22.7 mg, 28.3 µmoles, 62%). LRMS: not performed. $^1$H NMR: spectrum is consistent with the predicted structure.

N—(N'-(4-benzoylphenylalanine) aminoethyl)cyclopamine (49)

Aqueous ammonia (0.5 mL of a 29% (w/w) solution in water, 7.6 mmoles) was added to a solution of 48 (20.4 mg, 25.4 µmoles) in methanol (1 mL). The reaction was stirred at room temperature for 19 h and then evaporated to dryness by a stream of nitrogen gas. Purification by flash chromatography (SiO$_2$, step-wise gradient from 40:1:0.1 to 40:2:0.1 chloroform/methanol/triethylamine) yielded the amine as a colorless oil (17.9 mg, 25.4 µmoles, quant.). LRMS: not performed. $^1$H NMR: spectrum is consistent with the predicted structure.

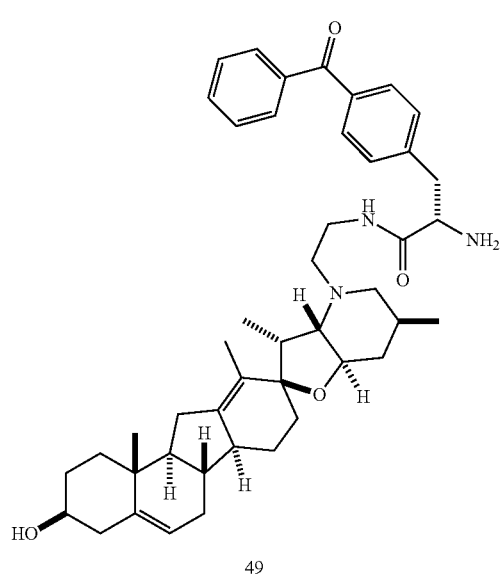

49

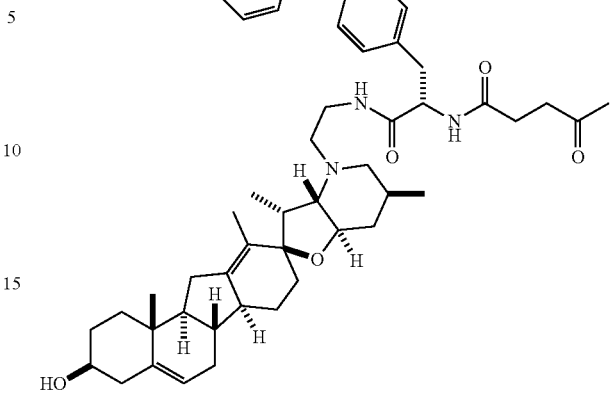

50

N—(N'—(N''-Levulinoyl(4-benzoylphenylalaminoyl))aminoethyl)cyclopamine (50)

Triethylamine (5.30 μL, 38.0 μmoles) and 47 (8.10 mg, 38.0 μmoles) were added to a solution of 49 (13.4 mg, 19.0 μmoles) in dichloromethane (0.5 mL). The reaction was stirred at room temperature for 4 h and then evaporated to dryness by a stream of nitrogen gas. Purification by flash chromatography (SiO$_2$, step-wise gradient from 40:1:0 to 40:2:0.1 chloroform/methanol/triethylamine) yielded the diketone as a colorless oil (11.3 mg, 14.1 μmoles, quant.). LRMS: (ES+) calcd for $C_{50}H_{65}N_3O_6$ (M+H): 804. found: 804. $^1$H NMR: spectrum is consistent with the predicted structure.

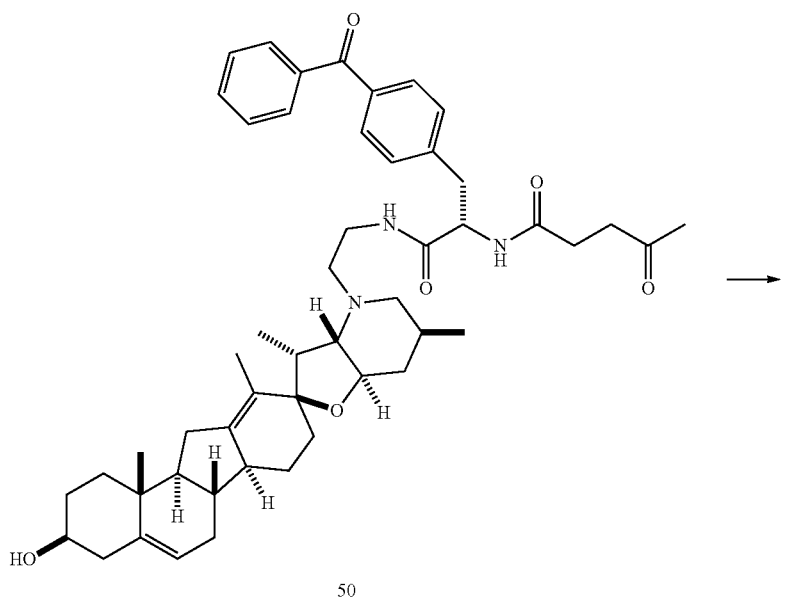

50

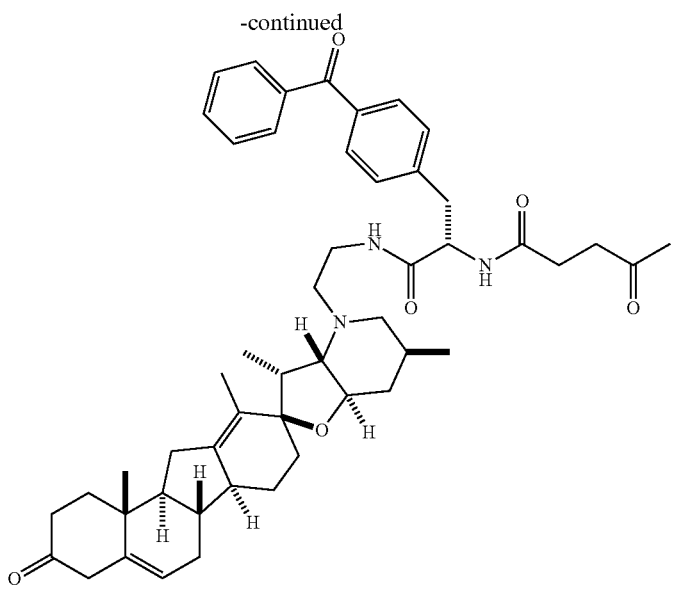

51

3-Keto N—(N'—(N''-Levulinoyl(4-benzoylphenyl-alaminoyl))aminoethyl) cyclopamine (51)

Dimethylsulfoxide (12.9 µL, 182 µmoles) was added to a solution of oxalyl chloride (7.96 µL, 91.2 µmoles) in dichloromethane (250 µL) at −78° C. After the mixture was stirred at −78° C. for 10 min, a solution of 50 (5.65 mg, 7.03 µmoles) in dichloromethane (250 µL) was added, and the reaction was stirred at −78° C. for another 30 min. The oxidation was completed by the addition of triethylamine (38.1 µL, 273 µmoles) to the solution, which was stirred at −78° C. for 10 min and then allowed to warm to room temperature. The reaction was quenched by the addition of saturated aqueous NaHCO$_3$ (2 mL) was extracted with chloroform (2×5 mL). The resultant organic layer was then dried over Na$_2$SO$_4$, and concentrated in vacuo. Purification by flash chromatography (SiO$_2$, step-wise gradient from 4:1 to 1:1 hexane/acetone) yielded the ketone as a white solid (1.4 mg, 1.75 µmoles, 25%). LRMS: (ES+) calcd for C$_{50}$H$_{63}$N$_3$O$_6$ (M+H): 802. found: 802. $^1$H NMR: spectrum is consistent with the predicted structure.

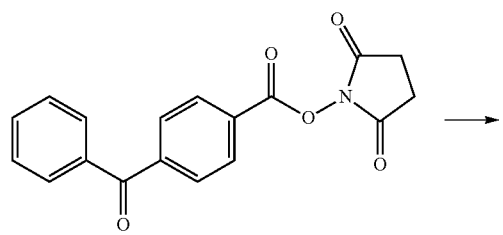

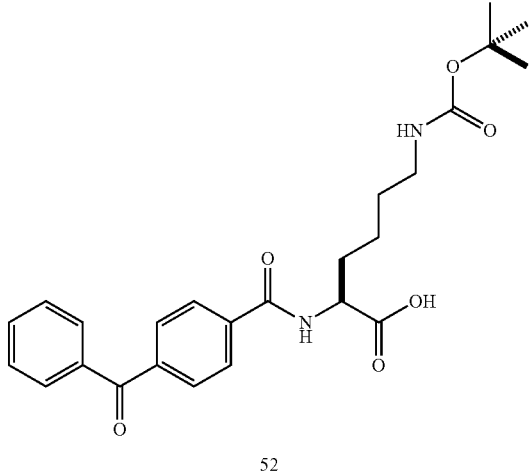

52

N,N'-(4-Benzoylbenzoyl)(tert-butoxycarbonyl)lysine (52)

4-Benzoylbenzoic acid N-hydroxysuccinimide ester (50.0 mg, 147 µmoles) was added to a solution of tert-butoxycarbonyl lysine (43.4 mg, 176 µmoles) in DMF (0.5 mL). 1 N NaOH (176 µL, 176 µmoles) and water (74 µL) was added to the reaction, and the mixture was stirred for 4 h at room temperature. 1 N NaOH was added again (352 µL, 352 µmoles) and the solution was stirred overnight. The reaction mixture was then mixed with water (2 mL) and washed with diethyl ether (2×2 mL). The aqueous layer was acidified with 1 N HCl until a pH of 2 was obtained, and the solution was extracted with ethyl acetate (2×2 mL). The resultant organic layer was dried over MgSO$_4$ and concentrated in vacuo. Purification by flash chromatography (SiO$_2$, step-wise gradient from 20:1:0.2 to 20:2:0.2 chloroform/methanol/acetic acid) yielded the benzophenone as colorless oil (40.0 mg, 88.0 μmoles, 60%). LRMS: (ES+) calcd for C$_{25}$H$_{30}$N$_2$O$_6$ (M+H): 455. found: 455. $^1$H NMR: spectrum is consistent with the predicted structure.

in vacuo and purification by flash chromatography (SiO$_2$, step-wise gradient from 20:1:0.1 to 20:2:0.1 chloroform/methanol/acetic acid) yielded the trifluoroacetamide as a colorless oil (31.3 mg, 69.5 μmoles, 89%). LRMS: (ES+) calcd for C$_{22}$H$_{21}$N$_2$O$_5$F$_3$ (M+H): 451. found: 451. $^1$H NMR: spectrum is consistent with the predicted structure.

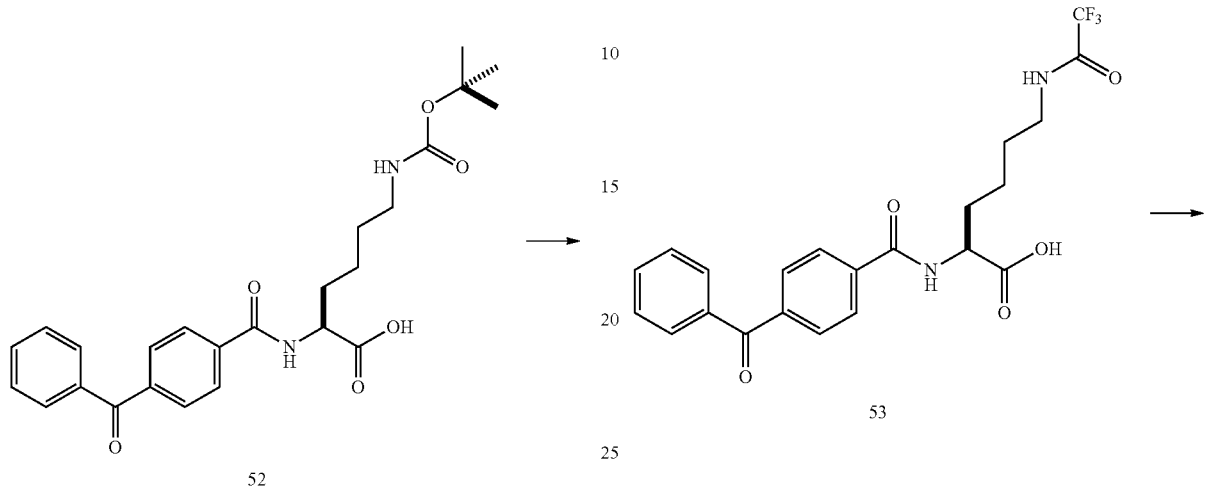

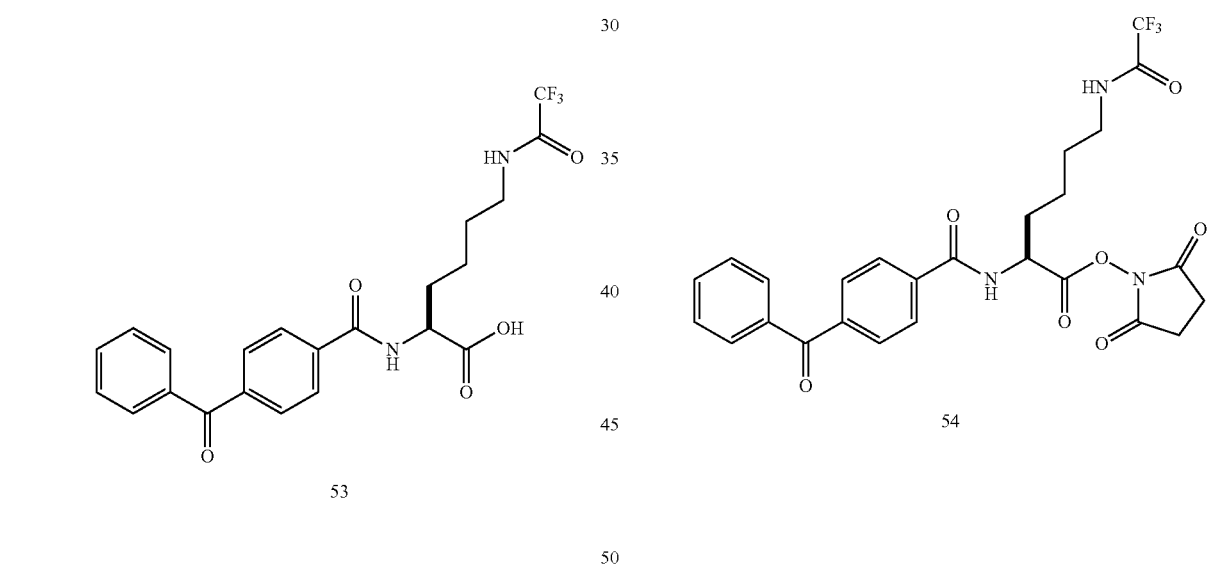

N,N'-(4-Benzoylbenzoyl)(trifluoroacetyl)lysine (53)

Benzophenone 52 (3.55 mg, 78.1 μmoles) was dissolved in trifluoroacetic acid (0.5 mL, 6.49 mmoles), and the solution was stirred at room temperature for 1 h. The trifluoroacetic acid was then removed with a stream of nitrogen gas, and the residue was resuspended in methanol (0.5 mL). After triethylamine (134.8 μL, 968 μmoles) and methyl trifluoroacetate (24.3 μL, 242 μmoles) were added to the methanol solution, the reaction was stirred for 26 h at room temperature. The reaction was evaporated to dryness N,N'-(4-Benzoylbenzoyl)(trifluoroacetyl)lysine N-hydroxysuccinimide ester (54)

Disuccinimidyl carbonate (16.0 mg, 62.6 μmoles) was added to a solution of 53 (28.2 mg, 62.6 μmoles) and pyridine (10.1 μL, 125 μmoles) in acetonitrile (1.0 mL). The reaction mixture was stirred at room temperature for 3 h, during which the solution became clear and evolved gas. The solution was added to ethyl acetate (10 mL), washed with 1 N HCl (1×2 mL) and saturated aqueous NaHCO$_3$ (1×2 mL), dried over MgSO$_4$, and concentrated in vacuo to yield a colorless oil (32.8 mg, 59.9 μmoles, 96%). LRMS: (ES+) calcd for C$_{26}$H$_{24}$N$_3$O$_7$F$_3$ (M+H): 548. found: 548. $^1$H NMR: spectrum is consistent with the predicted structure

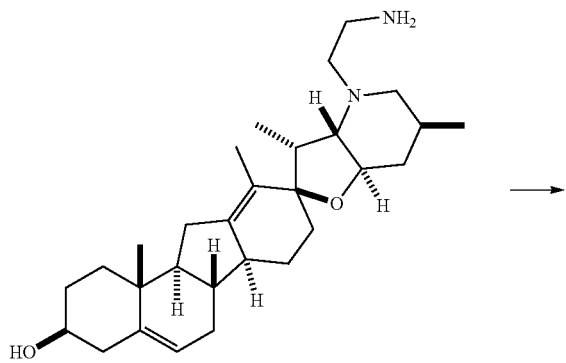

17

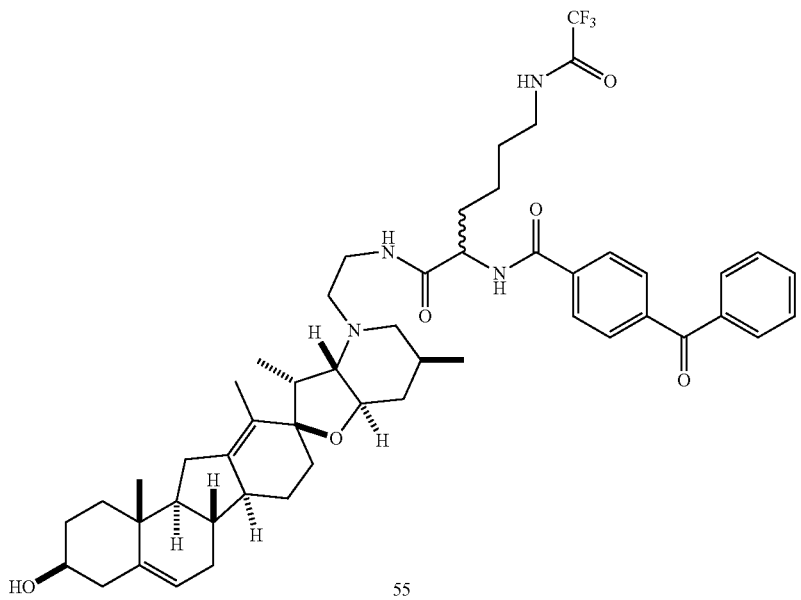

55

N—(N'—(N'',N'''-(4-Benzoylbenzoyl)(trifluoro-acetyl)lysine)aminoethyl) cyclopamine (55)

Triethylamine (8.36 μL, 60.0 μmoles) was added to a solution of 54 (16.4 mg, 30.0 μmoles) in dichloromethane (0.5 mL). The solution became bright yellow, indicating racemization of the amino acid α-carbon. A solution of 17 (13.6 mg, 30.0 μmoles) in dichloromethane (250 μL) was then added to the yellow solution. The reaction mixture was stirred for 1 h at room temperature, during which it became colorless, and purification by flash chromatography (SiO$_2$, step-wise gradient from 2:1 to 1:2 hexane/acaetone) yielded the cyclopamine derivative as a colorless oil (15.8 mg, 17.8 μmoles, 59%, mixture of diastereomers). LRMS: (ES+) calcd for C$_{51}$H$_{65}$N$_4$O$_6$F$_3$ (M+H): 887. found: 887. $^1$H NMR: spectrum is consistent with the predicted structure.

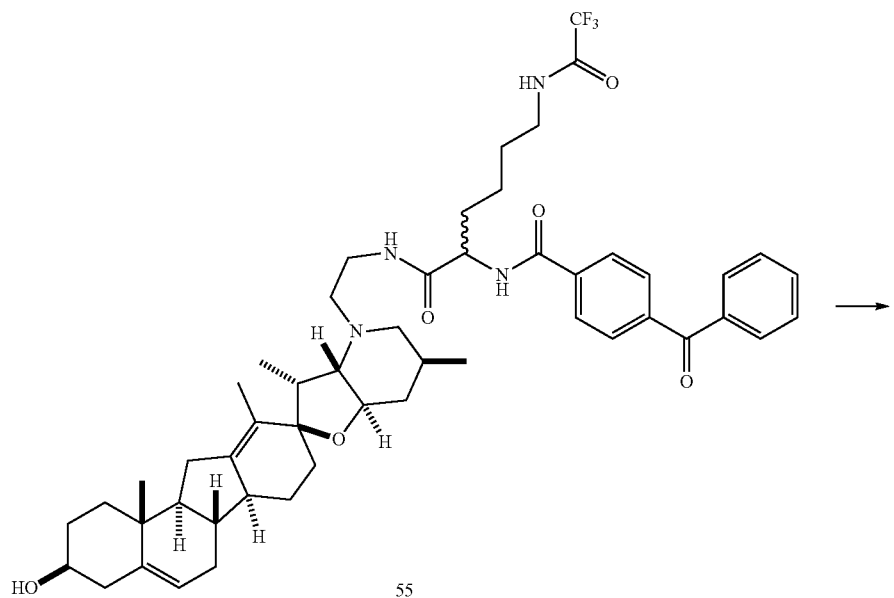

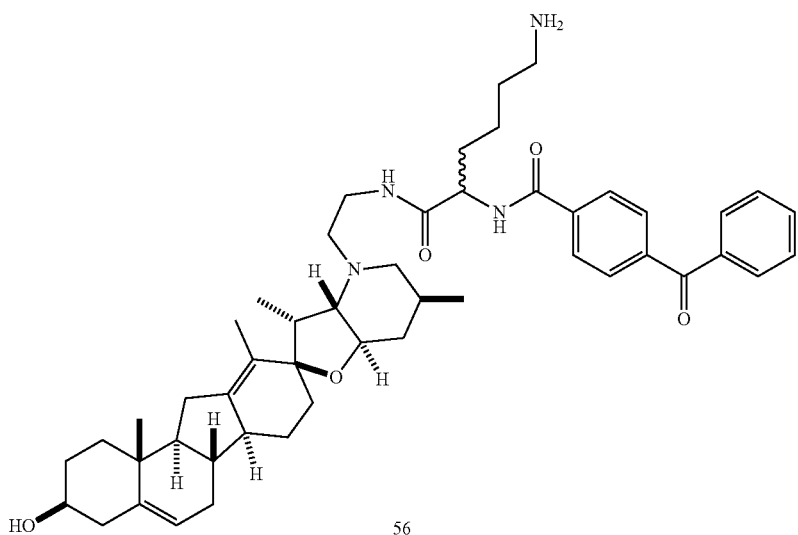

N—(N'-(4-Benzoylbenzoyl)lysine)aminoethyl)cyclopamine (56)

Compound 55 (13.0 mg, 14.7 μmoles) was dissolved in a 2 M solution of ammonia in methanol (1.0 mL, 2.00 mmoles). The reaction was stirred at room temperature for 23 h and then evaporated to dryness by a stream of nitrogen gas. Purification by flash chromatrography (SiO$_2$, step-wise gradient from 20:1:0.1 to 20:2:0.1 chloroform/methanol/triethylamine) yielded the amine as a white waxy solid (11.0 mg, 13.9 μmoles, mixture of diastereomers, 95%). LRMS: (ES+) calcd for C$_{49}$H$_{66}$N$_4$O$_5$ (M+H): 791. found: 791. $^1$H NMR: spectrum is consistent with the predicted structure.

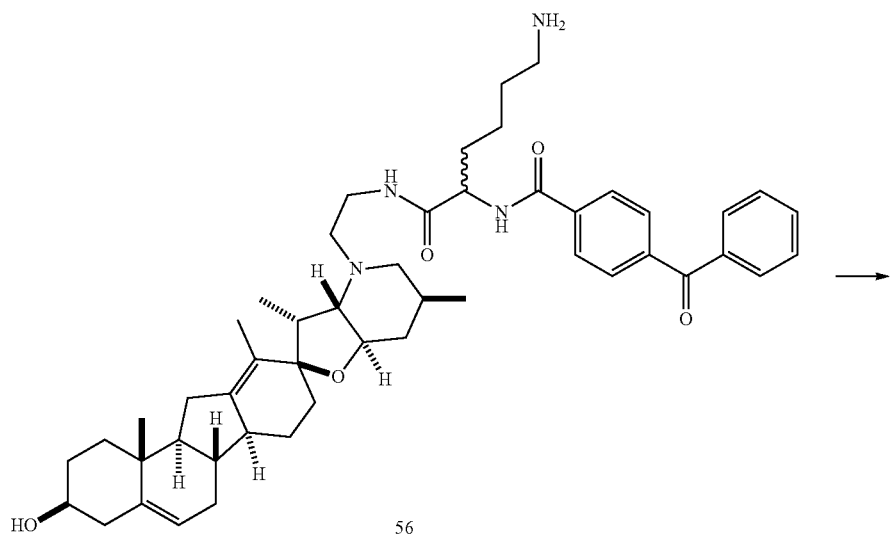

56

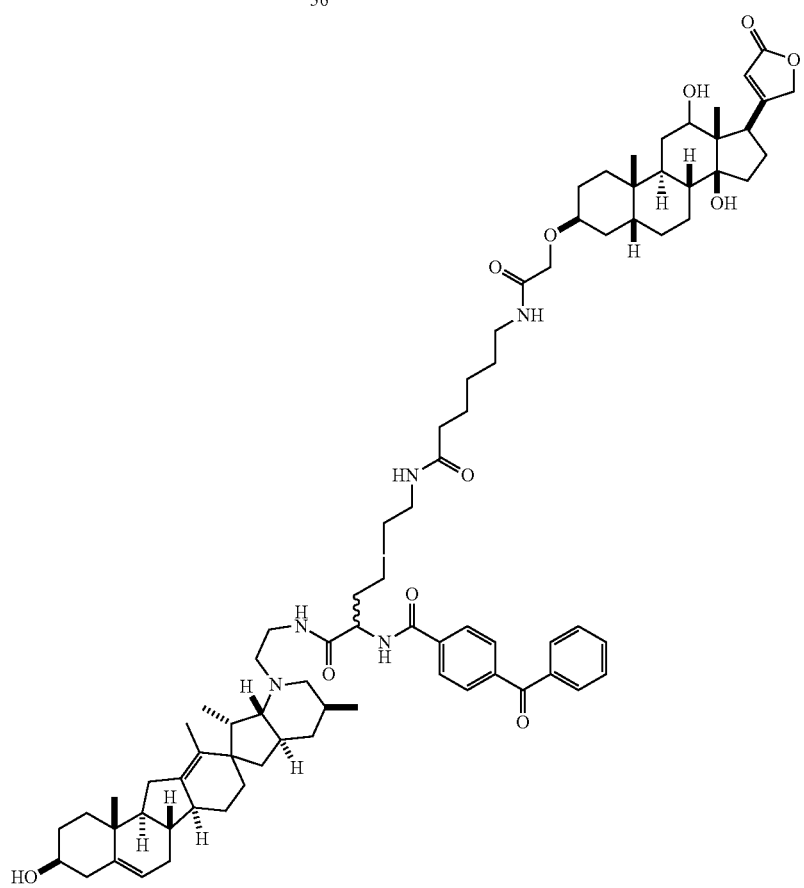

57

N—(N'—(N'',N'''-(4-Benzoylbenzoyl) (N''''-digoxigenin 3-O-methylcarbonyl aminocaproyl)lysine) aminoethyl)cyclopamine (57)

Digoxigenin 3-O-methylcarbonyl aminocaproic acid N-hydroxysuccinimide ester (5.0 mg, 7.59 µmoles) and triethylamine (1.59 µL, 11.4 µmoles) were added to a solution of 56 (4.5 mg, 5.69 µmoles) in dichloromethane (0.5 mL). After the solution was stirred for 2 h at room temperature, ethylenediamine (10 µL, 150 µmoles) was added and the reaction was stirred for an addition 15 min at room temperature. Saturated aqueous NaHCO₃ (2 mL) was added to the mixture, which was then extracted with chloroform (5 mL, then 2 mL). The organic layers were combined and dried over Na₂SO₄, and concentrated in vacuo. Purification by flash chromatography (SiO₂, step-wise gradient from 20:1 to 5:1 dichloromethane/methanol) yielded the digoxigenin derivative as white waxy solid (3.5 mg, 2.62 μmoles, 46%). LRMS: (ES+) calcd for $C_{80}H_{111}N_5O_{12}$ (M+H): 1337. found: 1337. $^1$H NMR: spectrum is consistent with the predicted structure.

μmoles) were added to a solution of 56 (4.5 mg, 5.69 μmoles) in DMF (250 μL). After the reaction was stirred for 2 h at room temperature, ethylenediamine (10 μL, 150 μmoles) was added to the solution, which was stirred for an addition 15 min at room temperature. Saturated aqueous

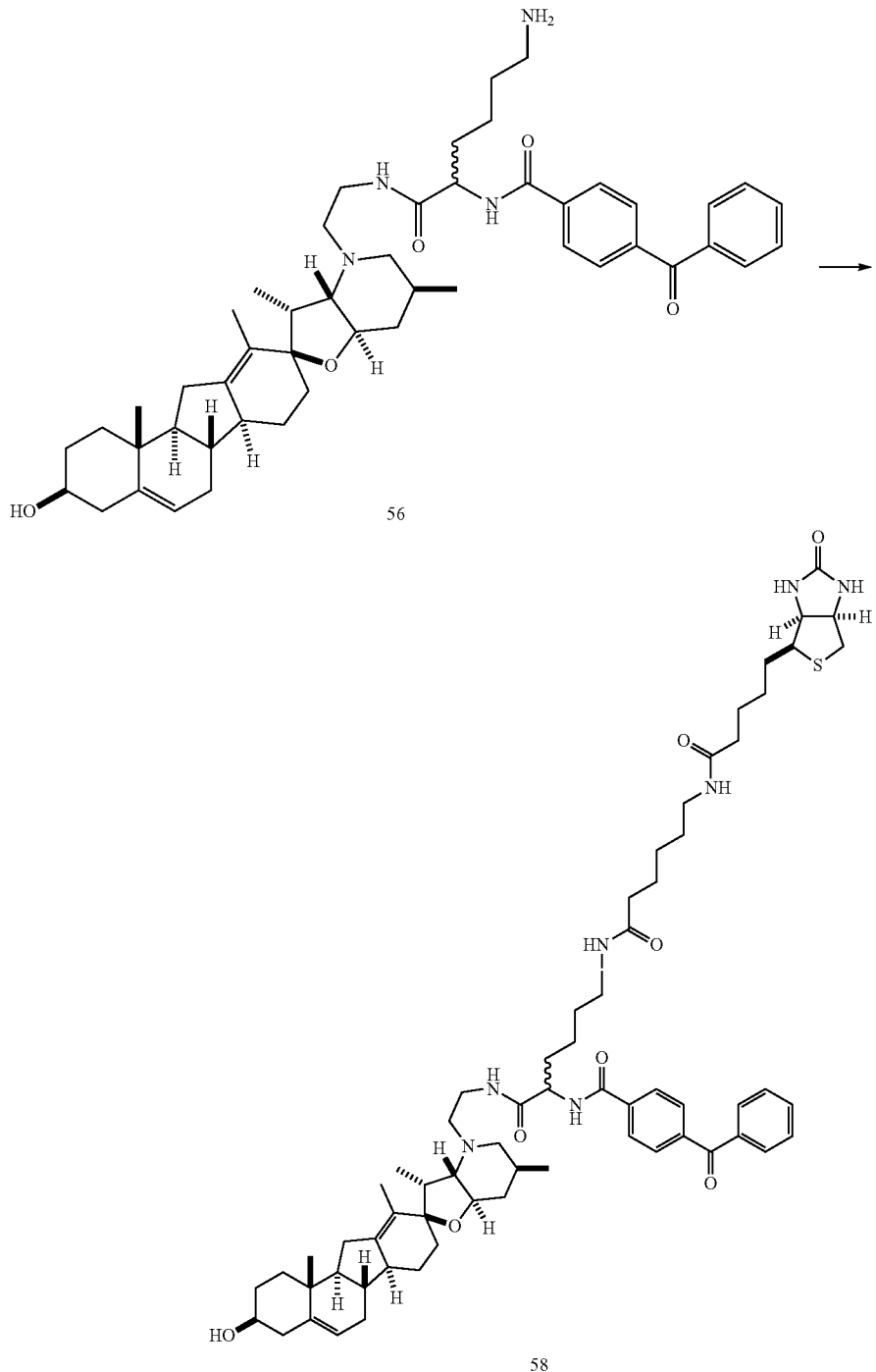

N—(N'—(N'',N'''-(4-Benzoylbenzoyl)(N''''-biotinoyl aminocaproyl)lysine)aminoethyl)cyclopamine (58)

N-Biotinoyl aminocaproic acid N-hydroxysuccinimide ester (2.6 mg, 5.69 μmoles) and triethylamine (1.59 μL, 11.4

NaHCO$_3$ (2 mL) was added to the mixture, which was then extracted with chloroform (1×2 mL). The organic layers were combined and dried over Na$_2$SO$_4$, and concentrated in vacuo. Purification by flash chromatography (SiO$_2$, stepwise gradient from 20:1 to 5:1 dichloromethane/methanol)

yielded the digoxigenin derivative as white waxy solid (3.4 mg, 3.01 µmoles, 53%). LRMS: (ES+) calcd for $C_{65}H_{91}N_7O_8S$ (M+H): 1130. found: 1130. $^1$H NMR: spectrum is consistent with the predicted structure.

gas yield a colorless oil (25.9 mg, 54.1 µmoles, quant.). LRMS: not performed. $^1$H NMR: spectrum is consistent with the predicted structure.

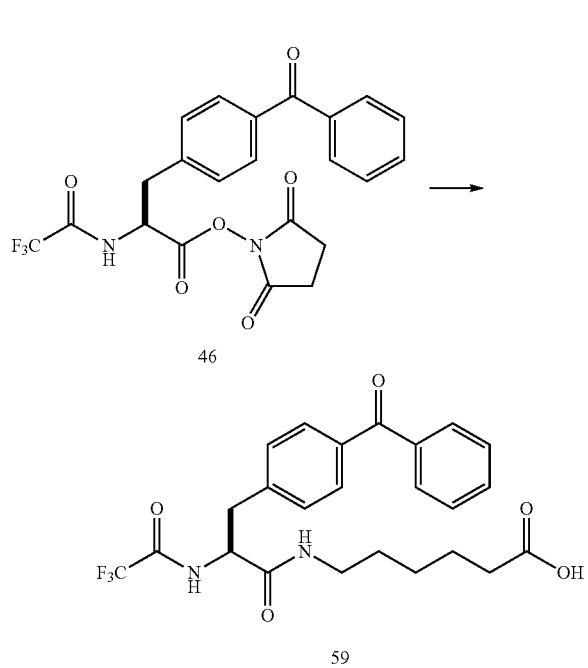

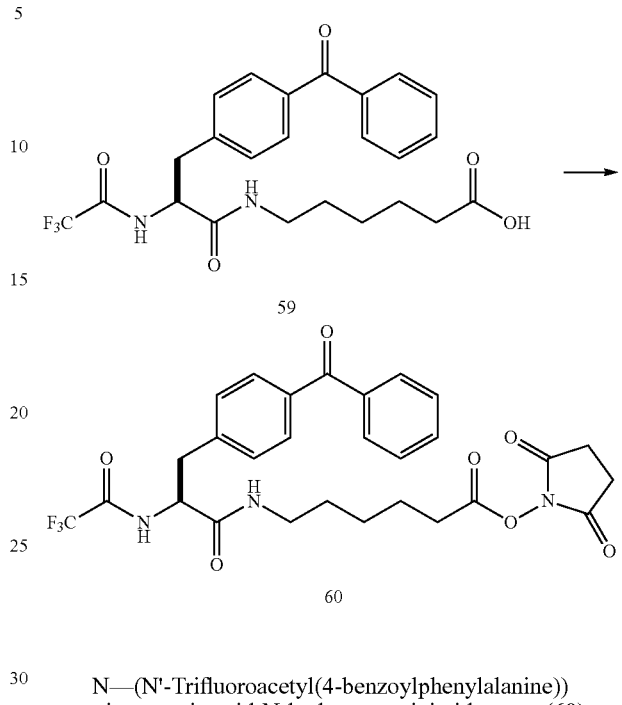

N—(N'-Trifluoroacetyl(4-benzoylphenylalanine)) aminocaproic acid N-hydroxysuccinimide ester (60)

N—(N'-Trifluoroacetyl(4-benzoylphenylalanine)) aminocaproic acid (59)

A solution of aminocaproic acid (10.8 mg, 80.5 µmoles) in water (100 µL) and a solution of 46 (24.4 mg, 53.7 µmoles) in DMF (100 µL) were combined and stirred for 45 min at room temperature. The reaction was then acidified with 1 N HCl until a pH of 2 was obtained, added to ethyl acetate (1 mL), washed with 1 N HCl (2×0.5 mL), dried over MgSO$_4$, and evaporated to dryness by a stream of nitrogen Disuccinimidyl carbonate (18.7 mg, 73.0 µmoles) was added to a solution of 59 (23.3 mg, 48.7 µmoles) and pyridine (7.88 µL, 97.4 µmoles) in acetonitrile (200 µL). The reaction mixture was stirred at room temperature for 12 h, during which the solution became clear and evolved gas. The solution was added to ethyl acetate (1 mL), washed with 1 N HCl (1×0.5 mL) and saturated aqueous NaHCO$_3$ (1×0.5 mL), dried over MgSO$_4$, and evaporated to dryness by a stream of nitrogen gas yield a colorless oil (26.4 mg, 45.9 µmoles, 94%.). LRMS: not performed. $^1$H NMR: spectrum is consistent with the predicted structure.

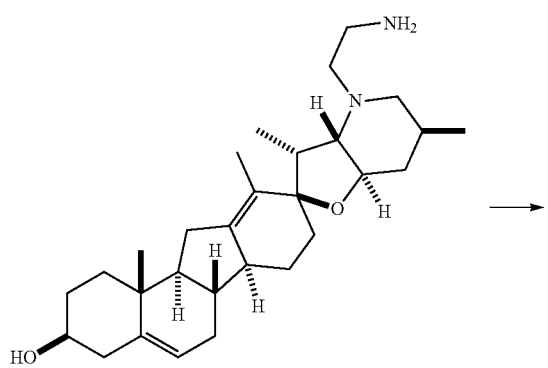

-continued

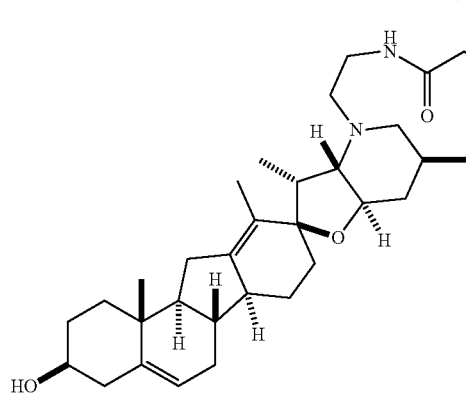

61

N—(N'—(N''—(N'''-Trifluoroacetyl(4-benzoylphenylalaminoyl))aminocaproyl)aminoethyl)cyclopamine (61)

Compound 60 (23.8 mg, 41.4 µmoles) and triethylamine (11.5 µL, 82.8 µmoles) were added a solution of 17 (15.7 mg, 34.5 µmoles) in dichloromethane (0.5 mL). The reaction was stirred for 1 h at room temperature and purification by flash chromatography (SiO$_2$, step-wise gradient from 2:1 to 1:2 hexane/acetone) yielded the benzophenone derivative as colorless oil (5.3 mg, 5.79 µmoles, 17%). LRMS: not performed. $^1$H NMR: spectrum is consistent with the predicted structure.

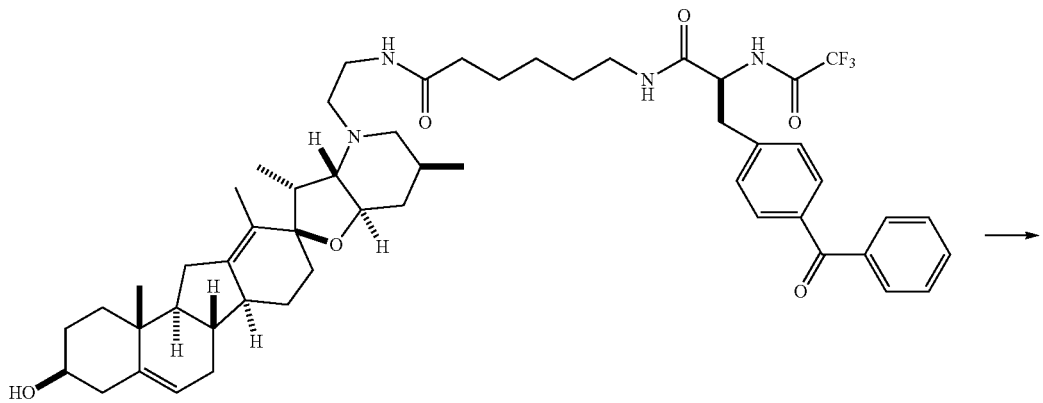

61

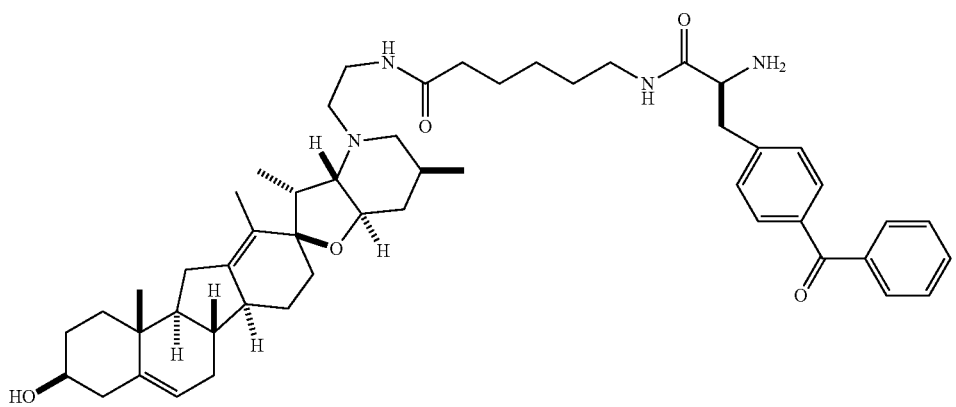

62

N—(N'—(N''-(4-Benzoylphenylalaminoyl) aminocaproyl)aminoethyl)cyclopamine (62)

Aqueous ammonia (250 µL of a 29% (w/w) solution in water, 3.80 mmoles) was added to a solution of 61 (5.3 mg, 5.79 µmoles) in methanol (200 µL). The reaction was stirred at room temperature for 18 h and then evaporated to dryness by a stream of nitrogen gas. Purification by flash chromatography (SiO$_2$, step-wise gradient from 20:1:0.05 to 20:2:0.05 chloroform/methanol/triethylamine) yielded the amine as a colorless oil (4.0 mg, 4.88 µmoles, 84%). LRMS: not performed $^1$H NMR: spectrum is consistent with the predicted structure.

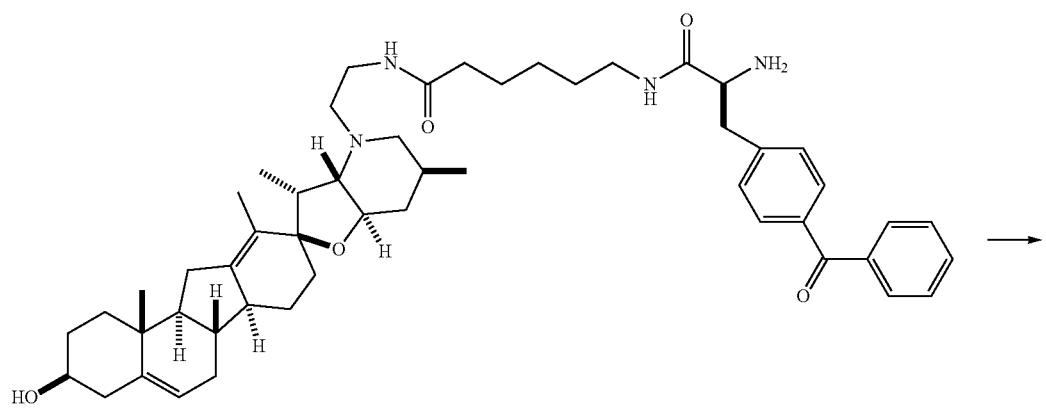

62

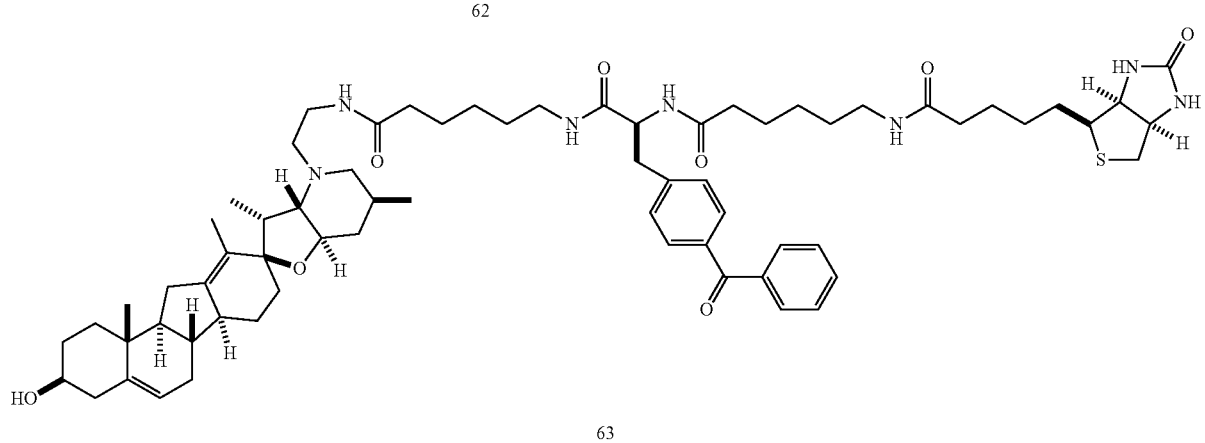

63

N—(N'—(N''—(N'''—(N''''-Biotinoyl aminocaproyl)(4-benzoylphenylalaminoyl))aminocaproyl)aminoethyl)cyclopamine (63)

N-Biotinoyl aminocaproic acid N-hydroxysuccinimide ester (2.7 mg, 5.86 µmoles) and triethylamine (1.4 µL, 9.76 µmoles) were added to a solution of 62 (4.0 mg, 4.88 µmoles) in DMF (250 µL). After the reaction was stirred for 15 min at room temperature, it was added to chloroform (2 mL), washed with saturated aqueous NaHCO$_3$, dried over Na$_2$SO$_4$, and concentrated in vacuo. Purification by flash chromatography (SiO$_2$, step-wise gradient from 20:1:0.05 to 20:4:0.05 chloroform/methanol/triethylamine) yielded the biotin derivative as white solid (4.5 mg, 3.88 µmoles, 80%). LRMS: (ES+) calcd for C$_{67}$H$_{95}$N$_7$O$_8$S (M+H): 1158. found: 1158. $^1$H NMR: spectrum is consistent with the predicted structure.

Example 3

In Vivo Testing

Methods:

Female nude mice were injected subcutaneously with 5 million P2A6 fibrosarcoma cells derived from Ptc−/− embryonic fibroblasts. Three weeks after injection, each mouse had developed a discrete subcutaneous tumor. Each tumor was measured and treatments were initiated on the same day. Mice were treated once daily with intraperitoneal injections of tomatidine, cyclopamine, or KAAD-cyclopamine 33 (one mouse per treatment) for four days. The mice were killed, and tumors were measured and dissected out for histopathologic analysis. Tumor volumes were calculated as the product of length x width. The samples were paraformaldehyde-fixed and paraffin-embedded, and slides were cut for hematoxylin and eosin staining and for immunohistochemistry with polyclonal antibodies against the proliferation marker Ki-67 (Novacastra NCL-Ki67p; assay performed according to manufacturer's directions).

Results:

As depicted in the graph, control treatment with tomatidine resulted in 17% tumor growth over the treatment period whereas treatment with cyclopamine decreased tumor size by 0.14% and treatment with KAAD-cyclopamine 33 decreased tumor size by 19%.

To confirm these results, Ki-67 proliferation rates were determined by a pathologist who was blinded to the treatment conditions. The magenta bars in the graph show proliferation rates for the three treatments. The proliferation rates for tomatidine, cyclopamine, and KAAD cyclopamine-treated tumors were 30%, 16%, and 12% respectively.

Figure 7:
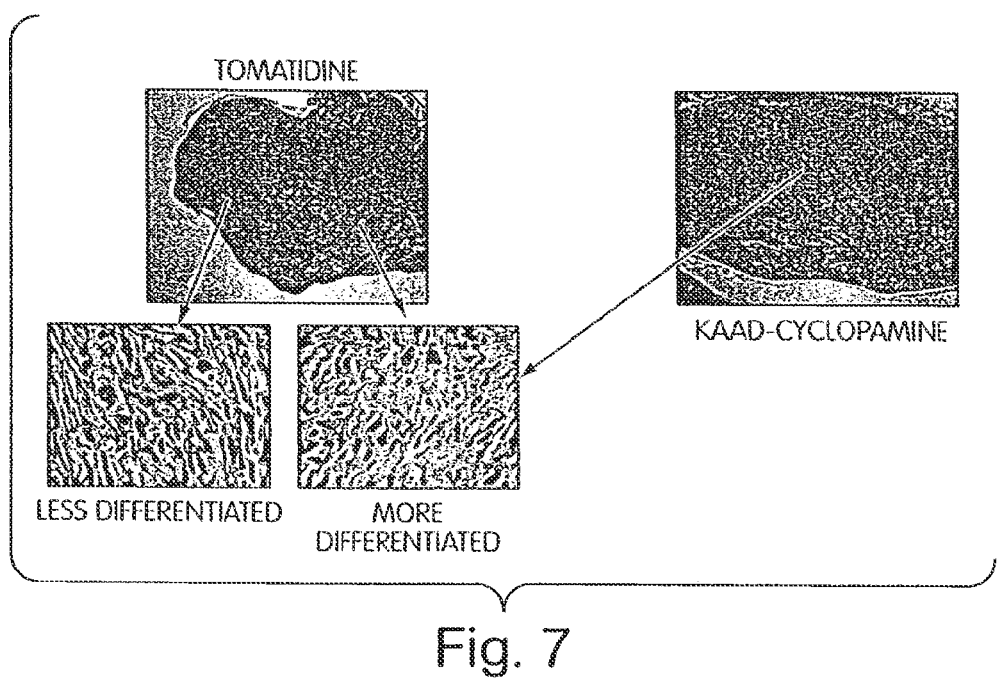
FIG. 7 compares tumor tissue following treatment with tomatidine with tissue treated with a subject compound.

Since the differentiation of many tumors correlates with prognosis, the differentiation status of the tumors was examined. All tumors showed zonal variation in differentiation as illustrated in the photomicrographs of FIG. 7. Compared to more poorly differentiated tumors, well differentiated fibrosarcomas have smaller, less crowded nuclei separated by relatively abundant pink collagen. As illustrated, KAAD-cyclopamine and cyclopamine (not shown) treated tumors showed a greater degree of differentiation than did the tomatidine-treated control.

EQUIVALENTS

Those skilled in the art will recognize, or be able to ascertain using no more than routine experimentation, many equivalents to the specific embodiments of the invention described herein. Such equivalents are intended to be encompassed by the following claims.

All patents and publications cited herein are hereby incorporated by reference in their entirety.

We claim:

1. A method for the treatment of a human subject having a basal cell carcinoma tumor, comprising
    administering to the subject an effective amount of a medicament comprising cyclopamine,
    wherein in said tumor smoothened-dependent hedgehog signaling is utilized for inhibition of apoptosis, and wherein said medicament is administered in a dose that induces apoptosis in said tumor, causes decrease of size of the tumor, and selectively inhibits smoothened-dependent hedgehog signaling in said tumor.

2. A method for the treatment of a human subject having a tumor in which smoothened-dependent hedgehog signaling is used, comprising
    administering to the subject an effective amount of a medicament comprising cyclopamine,
    wherein in said tumor smoothened-dependent hedgehog signaling is utilized for inhibition of apoptosis, and said medicament is administered in a dose that induces apoptosis in said tumor, causes decrease of size of the tumor and selectively inhibits smoothened-dependent hedgehog signaling in said tumor.

3. A method of claim 2 wherein smoothened-dependent hedgehog signaling is also used for inhibition of differentiation and said dose is sufficient to induce differentiation in said tumor.

4. A method of claim 2 wherein said amount of cyclopamine is not toxic to the subject.

5. A method of claim 3 wherein said amount of cyclopamine is not toxic to the subject.

6. A method of claim 3 wherein said medicament is a pharmaceutical composition for topical or systemic administration.

7. A method of claim 6 wherein the composition for systemic administration is in the form of an aqueous solution.

8. A method of claim 6 wherein the composition is systemically administered by injection.

9. A method of claim 6 wherein the pharmaceutical composition achieves controlled release.

10. A method of claim 6 wherein the pharmaceutical composition is in the form of a patch or a transdermal patch.

11. A method of claim 6 wherein the pharmaceutical composition is in the form of a cream or ointment or gel or hydrogel.

12. A method of claim 2 wherein the tumor is a skin tumor and the medicament is in the form of a pharmaceutical composition for injection or topical or oral or parenteral administration.

13. A method of claim 1 wherein said medicament is in the form of a pharmaceutical composition for topical administration and is applied 4 or more times a day.

14. A method of claim 13 wherein said medicament is in the form of a cream.

15. A method for treatment of a human subject having a tumor, comprising
    determining that smoothened-dependent hedgehog signaling is utilized for inhibition of apoptosis in said tumor, and
    administering to the subject a medicament comprising cyclopamine or a pharmaceutically acceptable salt thereof,
wherein said medicament is administered in a dose that is sufficient to induce apoptosis of said tumor cells and causes decrease of size of the tumor.

16. A method of claim 15 wherein said tumor is basal cell carcinoma.

17. A method for the treatment of a human subject having a tumor in which smoothened-dependent hedgehog signaling is used for inhibition of apoptosis and for selective inhibition of differentiation in said tumor, comprising administering to the subject an effective amount of a medicament comprising cyclopamine.

18. A method of claim 17 wherein said medicament is a pharmaceutical composition for topical or systemic administration.

19. A method of claim 18 wherein the composition for systemic administration is in the form of an aqueous solution.

20. A method of claim 18 wherein the composition is in the form of a liposome.

21. A method of claim 18 wherein the composition is administered by injection.

22. A method of claim 18 wherein the pharmaceutical composition achieves controlled release.

23. A method of claim 18 wherein the pharmaceutical composition is in the form of a patch or a transdermal patch.

24. A method of claim 18 wherein the pharmaceutical composition is in the form of a cream or ointment or gel or hydrogel.

25. A method of claim 17 wherein the tumor is a skin tumor and the medicament is in the form of a pharmaceutical composition for injection or topical or oral or parenteral administration.

26. A method of claim 6 wherein said medicament is in the form of a cream or a liposome.

* * * * *